(12) United States Patent
Veres et al.

(10) Patent No.: US 11,261,441 B2
(45) Date of Patent: Mar. 1, 2022

(54) VECTORS AND COMPOSITIONS FOR TREATING HEMOGLOBINOPATHIES

(71) Applicants: bluebird bio, Inc., Cambridge, MA (US); CHILDREN'S MEDICAL CENTER CORPORATION, Boston, MA (US)

(72) Inventors: Gabor Veres, Novato, CA (US); David A. Williams, Dover, MA (US)

(73) Assignees: bluebird bio, Inc., Cambridge, MA (US); Children's Medical Center Corporation, Boston, MA (US)

( * ) Notice: Subject to any disclaimer, the term of this patent is extended or adjusted under 35 U.S.C. 154(b) by 0 days.

(21) Appl. No.: 16/496,720

(22) PCT Filed: Mar. 29, 2018

(86) PCT No.: PCT/US2018/025165
§ 371 (c)(1),
(2) Date: Sep. 23, 2019

(87) PCT Pub. No.: WO2018/183692
PCT Pub. Date: Oct. 4, 2018

(65) Prior Publication Data
US 2020/0109399 A1  Apr. 9, 2020

Related U.S. Application Data

(60) Provisional application No. 62/489,149, filed on Apr. 24, 2017, provisional application No. 62/478,149, filed on Mar. 29, 2017.

(51) Int. Cl.
| | | |
|---|---|---|
| *C12N 15/113* | (2010.01) | |
| *A61K 9/00* | (2006.01) | |
| *A61K 31/7088* | (2006.01) | |
| *C12N 15/86* | (2006.01) | |

(52) U.S. Cl.
CPC .......... *C12N 15/113* (2013.01); *A61K 9/0019* (2013.01); *A61K 31/7088* (2013.01); *C12N 15/86* (2013.01); *C12N 2310/11* (2013.01); *C12N 2320/32* (2013.01); *C12N 2330/51* (2013.01); *C12N 2740/15043* (2013.01); *C12N 2740/15045* (2013.01); *C12N 2740/15071* (2013.01); *C12N 2830/008* (2013.01)

(58) Field of Classification Search
CPC .............. C12N 15/113; C12N 2330/51; C12N 2740/15043; C12N 2830/008; C12N 2310/14; C12N 2740/16043
See application file for complete search history.

(56) References Cited

U.S. PATENT DOCUMENTS

| | | |
|---|---|---|
| 5,460,964 A | 10/1995 | McGlave et al. |
| 5,635,387 A | 6/1997 | Fei et al. |
| 5,677,136 A | 10/1997 | Simmons et al. |
| 5,716,827 A | 2/1998 | Tsukamoto et al. |
| 5,750,397 A | 5/1998 | Tsukamoto et al. |
| 5,759,793 A | 6/1998 | Schwartz et al. |
| 5,928,638 A | 7/1999 | Uchida et al. |
| 6,682,907 B1 | 1/2004 | Charneau et al. |
| 9,228,185 B2 | 1/2016 | Orkin et al. |
| 9,885,041 B2 | 2/2018 | Orkin et al. |
| 10,287,588 B2 * | 5/2019 | Milsom .................. C12N 7/00 |
| 10,662,429 B2 * | 5/2020 | Milsom .............. C12N 15/1135 435/325 |
| 2004/0259247 A1 | 12/2004 | Tuschl et al. |
| 2005/0227917 A1 | 10/2005 | Williams et al. |
| 2008/0051431 A1 | 2/2008 | Verhelle et al. |
| 2010/0273213 A1 | 10/2010 | Mineno et al. |
| 2011/0182867 A1 | 7/2011 | Orkin et al. |
| 2011/0294114 A1 * | 12/2011 | Van Der Loo ......... C12N 15/86 435/6.1 |
| 2013/0004471 A1 * | 1/2013 | Denaro ................ C12N 5/0686 424/93.21 |
| 2014/0001841 A1 | 1/2014 | Novobrantseva et al. |
| 2015/0132269 A1 | 5/2015 | Orkin et al. |
| 2017/0173184 A1 * | 6/2017 | Gaspar ............. C12Y 302/0102 |

FOREIGN PATENT DOCUMENTS

| | | | |
|---|---|---|---|
| EP | 1752536 A1 | 2/2007 | |
| EP | 2334794 B1 | 11/2016 | |
| EP | 2334794 B8 | 4/2017 | |
| JP | 2006507841 A | 3/2006 | |
| WO | WO 2004/054512 A2 | 7/2004 | |
| WO | WO 2009/007685 A2 | 1/2009 | |
| WO | WO 2011/072086 A1 | 6/2011 | |
| WO | WO 2012/073047 A2 | 6/2012 | |
| WO | WO 2013/049615 A1 | 4/2013 | |
| WO | WO 2014/085593 A1 | 6/2014 | |
| WO | WO 2014/093965 A1 | 6/2014 | |
| WO | WO 2015/065964 A1 | 5/2015 | |
| WO | WO 2015/164759 A2 | 10/2015 | |
| WO | WO-2015164739 A1 * | 10/2015 | ....... C07K 14/70521 |
| WO | WO-2015164750 A2 * | 10/2015 | ........... C12N 15/113 |

(Continued)

OTHER PUBLICATIONS

Cante-Barret et al (BMC Res Notes (2016) 9:312) (Year: 2016).*
US 5,681,599, DiGuisto et al. (withdrawn)
Akinsheye et al., "Fetal hemoglobin in sickle cell anemia." Blood 118(1):19-27 (2011).
Amaya et al., "Mi2Jl-mediated silencing of the fetal y-globin gene in adult erythroid cells." Blood 121(17):3493-501 (2013).
Amendah et al., "Sickle cell disease-related pediatric medical expenditures in the U.S." American Journal of preventive Medicine 38(4 Suppl):S550-S556 (2010).
Atweh et al., "Pharmacological induction of fetal hemoglobin in sickle cell disease and beta-thalassemia." Seminars in Hematology 38(4):367-73 (2001).

(Continued)

*Primary Examiner* — Richard A Schnizer
(74) *Attorney, Agent, or Firm* — Morse, Barnes-Brown & Pendleton, P.C.; Lisa M. Warren, Esq.; Erin E. Bryan, Esq.

(57) ABSTRACT

The invention provides improved gene therapy vectors, compositions, and methods.

13 Claims, 14 Drawing Sheets

Specification includes a Sequence Listing.

(56) References Cited

FOREIGN PATENT DOCUMENTS

| WO | WO 2016/094304 A2 | 6/2016 |
|---|---|---|
| WO | WO 2016/182893 A1 | 11/2016 |
| WO | WO 2017/040529 A1 | 3/2017 |
| WO | WO 2017/139576 A1 | 8/2017 |

OTHER PUBLICATIONS

Bauer et al., "An erythroid enhancer of BCL11A subject to genetic variation determines fetal hemoglobin level," Science. Oct. 11, 2013;342(6155):253-7.

Bauer et al., "HbF-Associated Genetic Variation Marks an Erythroid Regulatory Element Essential for BCL11A transcription and Subsequent Stage-Specific Globin Expression." Blood 120:828 (2012).

Bauer et al., "Hemoglobin switching's surprise: the versatile transcription factor BCL11A is a master repressor of fetal hemoglobin" Current Opinion in Genetics & Development 33:62-70 (2015).

Bauer et al., "Reawakening fetal hemoglobin: prospects for new therapies for the B-globin disorders." Blood 120 [15]:2945-2953 (2012).

Bauer et al., "Supplementary Material: An Erythroid Enhancer of BCL11A Subject to Genetic Variation Determines Fetal Hemoglobin Level." Science 342(6155):253-257 (2013).

Bjurstrom et al. "Reactivating fetal hemoglobin expression in human adult erythroblasts through BCL11A knockdown using targeted endonucleases." Molecular Therapy—Nucleic Acids 5:e351 (2016).

Boettcher et al., "Choosing the right tool for the job: RNAi, TALEN, or CRISPR." Molecular Cell 58(4):575-585 (2015).

Bohmer et al., "Identification of fetal nucleated red cells in co-cultures from fetal and adult peripheral blood: differential effects of serum on fetal and adult erythropoiesis." Prenatal Diagnosis 19(7):628-636 (1999).

Bunn "Reversing ontogeny." New Engl. J_ Med. 328(2):129-131 (1993).

Canver et al., "BCL11A enhancer dissection by Cas9-mediated in situ saturating mutagenesis." Nature 527 (7577):192-197 (2015).

Cao et al., "Recent advances in B-thalassemias." Pediatric Reports 3(2):65-71 (2011).

Cavazzana-Calvo, M. et al., "Transfusion independence and HMGA2 activation after gene therapy of human β-thalassaemia", Nature (2010), 467(7313): 318-322.

Chabchoub et al., "The facial dysmorphy in the newly recognised microdeletion 2p15-p16.1 refined to a 570 kb region in 2p15." Journal of Medical Genetics 45(3):189-192 (2008).

Clever, J. et al., "RNA Secondary Structure and Binding Sites for gag Gene Products in the 59 Packaging Signal of Human Immunodeficiency Virus Type 1", J. of Virology (1995), 69(4): 2101-2109.

Coleman et al., "Sickle cell anemia: targeting the role of fetal hemoglobin in therapy." Clinical Pediatrics 46 (5):386-391 (2007).

Cox et al., "Therapeutic genome editing: prospects and challenges" Nature Medicine 21(2):121-131 (2015).

Cullen et al., "Regulatory Pathways Governing HIV-1 Replication", Cell (1989); 58: 423-426.

Cullen, B.R., "Human Immunodeficiency Virus as a Prototypic Complex Retrovirus", Journal of Virology (1991); 65(3): 1053-1056.

Dixit et al., "Hydroxyurea in thalassemia intermedia—a promising therapy." Annals of Hematology 84(7):441-446 [2005].

Doench et al., "Rational design of highly active sgRNAs for CRISPR-Cas9-mediated gene inactivation." Nature Biotechnology 32(12):1262-1267 (2014).

Doench et al., "Supplementary Material: Rational design of highly active sgRNAs for CRISPR-Cas9-mediated gene inactivation." Nature Biotechnology 32(12):1262-1267 (2014).

Examination Search Report, dated May 11, 2018 in corresponding Canadian No. 2737180.

Fenaux "Inhibitors of DNA methylation: beyond myelodysplastic syndromes." Nature Reviews Clinical Oncology 2 (S21):S36-S44 (2005).

Fischer et al., "Pulmonary Passage is a Major Obstacle for Intravenous Stem Cell Delivery: The Pulmonary First Pass Effect" Stem Cells and Development 18(5):683-91 (2009).

Flanagan et al., "Hydroxycarbamide alters erythroid gene expression in children with sickle cell anaemia." BritishJournal of Haematology 157(2):240-248 (2012).

GenBank Accession No. NM_022893.4. "*Homo sapiens* BAF chromatin remodeling complex subunit BCL11A (BCL11A), transcript variant 1, mRNA." https://www.ncbi.nlm.nil1.gov/nuccore/NM_022893.4 (2019).

GeneCard for BCL11A, retrieved from http://www.genecards.org/cgi-bin/carddisp.pl?gene=BCL11A on Jun. 22, 2012.

Ginn, et al., "Gene therapy clinical trials worldwide to 2012—an update." The Journal of Gene Medicine (2013); 15 (2): 65-77.

Goffin et al., "DNA methyltransferase inhibitors—state of the art." Annals of Oncology 13(11):1699-716 (2002).

Goldberg et al., "Treatment of sickle cell anemia with hydroxyurea and erythropoietin." New England Journal of Medicine 323(6):366-372 (1990).

Hackam "Translating animal research into clinical benefit" BMJ 334:163-68 (2007).

Hancarova et al. "A patient with de nova 0.45 Mb deletion of 2p16. 1: The role of BCL11A, PAPOLG, REL, and FLJ16341 in the 2p15-p16. 1 microdeletion syndrome." American Journal of Medical Genetics Part A 161(4):865-870 (2013).

Harding et al., "Large animal models for stem cell therapy", Stem Cell Research & Therapy 4(23):1-9 (2013).

Hebbel et al., "The HDAC inhibitors trichostatin A and suberoylanilide hydroxamic acid exhibit multiple modalities of benefit for the vascular pathobiology of sickle transgenic mice." Blood 115(12):2483-2490 (2010).

Hendel et al., "Chemically modified guide RNAs enhance CRISPR-Cas genome editing in human primary cells." Nature Biotechnology 33(9):985-989 (2015).

Higgs et al., "Genetic complexity in sickle cell disease." PNAS 105(33):11595-11596 (2008).

Ho et al., "In vitro induction of fetal hemoglobin in human erythroid progenitor cells." Experimental Hematology 31 (7):586-591 (2003).

Hsieh et al., "Allogeneic hematopoietic stem-cell transplantation for sickle cell disease." New England Journal of Medicine 361(24):2309-2317 (2009).

Huang et al., "Role of the hepatitis B virus posttranscriptional regulatory element in export of intronless transcripts," Molecular and Cellular Biology (1995); 15(7): 3864-3869.

Imren, S. et al., "Permanent and panerythroid correction of murine β thalassemia by multiple lentiviral integration in hematopoietic stem cells", Proc Natl Acad Sci U S A (2002), 99(22): 14380-14385.

International Search Report and Written Opinion dated Jun. 25, 2018, for International Application No. PCT/US2018/025165, 10 pages.

Jane et al., "Understanding fetal globin gene expression: a step towards effective HbF reactivation in haemoglobinopathies." British Journal of Haematology 102(2):415-423 (1998).

Kauf et al., "The cost of health care for children and adults with sickle cell disease." American Journal of Hematology 84(6):323-327 (2009).

Kirschner et al., "Genomic mapping of chromosomal region 2p15-p21 {D2S378-D2S391): integration of Genemap'98 within a framework of yeast and bacterial artificial chromosomes" Genomics 62(1):21-33 (1999).

Koshy et al., "2-deoxy 5-azacytidine and fetal hemoglobin induction in sickle cell anemia." Blood 96(7):2379-2384 (2000).

Kutner, et al., "Simplified production andconcentration of HIV-1-based lentiviral vectors using HYPERFlask vessels and anion exchange membrane chromatography", BMC Biotechnol. (2009); 9:10. p. 1-7.

Kutner et al., "Production, concentration and titration of pseudotyped HIV-1-based lentiviral vectors", Nature Protocols (2009); 4: 495-505.

(56) References Cited

OTHER PUBLICATIONS

Labie "Le controle en trans de la production d'hemoglobine fretale: une recherche qui dure depuis 20 ans." Hematologie 14(2):165-166 (2008).
Lettre et al., "DNA polymorphisms at the BCL11A, HBS1L-MYB, and beta-globin loci associate with fetal hemoglobin levels and pain crises in sickle cell disease." PNAS 105{33):11869-11874 (2008).
Landau et al., "Packaging system for rapid production of murine leukemia virus vectors with variable tropism." Journal of Virology (1992); 66.8: 5110-5113.
Liu et al., "HnRNP L binds a cis-acting RNA sequence element that enables intron-dependent gene expression," Genes & Dev. (1995); 9: 1766-1780.
Liu et al., "Bcl11a is essential for normal lymphoid development." Nature Immunology 4(6):525-532 (2003).
Liu et al., "Functional studies of BCL11A: characterization of the conserved BCL11A-XL splice variant and its interaction with BCL6 in nuclear paraspeckles of germinal center B cells." Molecular Cancer 5(18):1-6 (2006).
Luc et al., "Bcl11a-deficiency leads to hematopoietic stem cell defects with an aging-like phenotype," Cell Rep. Sep. 20, 2016; 16(12): 3181-3194.
Lulli et al., "MicroRNA-486-3p regulates y-globin expression in human erythroid cells by directly modulating BCL11A." PLoS One 8(4):e60436 (2013).
Makala et al., "Fetal Hemoglobin Induction to Treat b-Hemoglobinopathies: From Bench to Bedside" J Hematol Transfus 2(2):1-2 (2014).
Malik, P. et al., "Successful Correction of the Human Cooley's Anemia—Thalassemia Major Phenotype Using a Lentiviral Vector Flanked by the Chicken Hypersensitive Site 4 Chromatin Insulator", Annals of the New York Academy of Sciences (2005), Annals of the New York Academy of Sciences vol. 1054, Cooley's Anemia: Eighth Symposium pp. 238-249, Nov. 2005.
Martin-Subero et al., "Recurrent involvement of the REL and BCL11Aloci in classical Hodgkin lymphoma." Blood 99(4):1474-1477 (2002).
Matsuda et al., "Transcription factors LRF and BCL11A independently repress expression of fetal hemoglobin" Science 351(6270):285-289 (2016).
May, C. et al., "Therapeutic haemoglobin synthesis in β-thalassaemic mice expressing lentivirus-encoded human beta-globin", Nature (2000), 406(6791): 82-86.
Menzel et al., "A QTL influencing F cell production maps to a gene encoding a zinc-finger protein on chromosome p15." Nature Genetics 39(10):1197-1199 (2007).
Migliaccio et al., "Influence of recombinant hematopoietins and of fetal bovine serum on the globin synthetic pattern pf human BFUe." Blood 76(6):1150-1157 (1990).
Moffat et al., "A lentiviral RNAi library for human and mouse genes applied to an arrayed viral high-content screen." 124(6):1283-1298 (2006).
Naldini, L., "Gene therapy returns to centre stage." Nature (2015); 526(7573): 351-360.
Nemudryi et al., "TALEN and CRISPR/Cas Genome Editing Systems: Tools of Discovery" Acta Naturae, 6(3):19-40 (2014).
Neven et al., "A Mendelian predisposition to B-cell lymphoma caused by IL-10R deficiency," Blood 3713-3722 (2013).
Orkin et al., "Recent advances in globin research using genome-wide association studies and gene editing." Annals of the New York Academy of Sciences 1368 (1):5-10 (2016).
Papayannopoulou et al., "Erythroid progenitors circulating in the blood of adult individuals produce fetal hemoglobin in culture." Science 199{4335):1349-1350 (1978).
Pauling et al., "Sickle cell anemia a molecular disease." Science 110(2865):543-548 (1949).
Pawliuk, R. et al., "Correction of sickle cell disease in transgenic mouse models by gene therapy", Science (2001), 294(5550): 2368-2371 (and Supplementary Material).
Pembrey et al., "Fetal haemoglobin production and the sickle gene in the oases of Eastern Saudi Arabia." British Journal of haematology 40(3):415-429 (1978).
Perrine "Fetal globin induction—can it cure beta thalassemia?" American Society of Hematology Education Program Book pp. 38-44 (2005).
Platt et al., "Mortality in sickle cell disease. Life expectancy and risk factors for early death." New England Journal of Medicine 330(23):1639-1644 (1994).
Purton et al., "All-trans retinoic acid enhances the long-term repopulating activity of cultured hematopoietic stem cells." Blood 95(2):470-477 (2000).
Pusch et al., "Enhanced gene silencing of HIV-1 speci® c siRNA using microRNA designed hairpins," Nucleic Acids Research, 2004, vol. 32, No. 3, 1154-1158.
Renella et al. "Hematopoietic SIN lentiviral micro RNA-mediated silencing of BCL11A: pre-clinical evidence for a sickle cell disease gene-therapy trial." 120(21):Abstract 753 (2012).
Ridley et al., "Erythropoietin: A Review" J Natl Med Assoc., 86(2):129-135 (1994).
Rodriguez et al., "A bioavailability and pharmacokinetic study of oral and intravenous hydroxyurea." Blood 9 (5):1533-1541 (1998).
Rosenblum et al., "Peripheral blood erythroid progenitors from patients with sickle cell anemia: HPLC separation of hemoglobins and the effect of a HbF switching factor." Progress in Clinical and Biological Research 191:397-410 1985).
Saiki et al., "Human EVI9, a homologue of the mouse myeloid leukemia gene, is expressed in the hematopoietic progenitors and down-regulated during myeloid differentiation of HL60 cells." Genomics 70(3):387-391 (2000).
Sankaran et al., "Developmental and species-divergent globin switching are driven by BCL11A." Nature 460 (7259):1093-1097 (2009).
Sankaran et al., "Human fetal hemoglobin expression is regulated by the developmental stage-specific repressor BCL11A." Science 322(5909):1839-1843 (2008).
Sankaran et al., "Targeted therapeutic strategies for fetal hemoglobin induction." American Society of Hematology Education Program Book 2011(1):459-465 (2011).
Satterwhite et al., "The BCL11 gene family: involvement of BCL11A in lymphoid malignancies." Blood, 98 (12):3413-3420 (2001).
Schopman et al. "Optimization of shRNA inhibitors by variation of the terminal loop sequence." Antiviral Research 86 (2):204-211 (2010).
Sebastiani et al., "BCL11A enhancer haplotypes and fetal hemoglobin in sickle cell anemia." Blood Cells, Molecules, and Diseases 54(3):224-230 (2015).
Sedgewick et al., "BCL11A is a major HbF quantitative trail locus in three different populations with β hemoglobinopathies." Blood Cells, Molecules, and Diseases 41(3):255-258 (2008).
Shen et al., "Modifcation of globin gene expression by RNA targeting strategies." Experimental Hematology, 35 fB): 1209-1218 (2007).
Soneoka, Yuko, et al. "A transient three-plasmid expression system for the production of high titer retroviral vectors." Nucleic Acids Research (1995); 23.4: 628-633.
Takeuchi et al., "Redesign of extensive protein-DNA interfaces of meganucleases using iterative cycles of in vitro compartmentalization." PNAS 111(11):4061-4066 (2014).
Taymans et al., "Radiation hybrid mapping of chromosomal region 2p15-p16: integration of expressed and polymorphic sequences maps at the Carney complex (CNC) and Doyne honeycomb retinal dystrophy (DHRD) loci." Genomics 56(3):344-349 (1999).
Terasawa et al., "Synthetic pre-miRNA-based shRNA as potent RNAi triggers." Journal of Nucleic Acids (2011).
Thein "Genetic modifiers of the beta-haemoglobinopathies." British Journal of Hematology, 141(3):357-366 (2008).
Thein et al., "Discovering the genetics underlying foetal haemoglobin production in adults." British Journal of aematology 145(4):455-467 (2009).
Thompson "Structure, Function, and Molecular Defects of Factor IX." Blood 67(3):565-72 (1986).

(56) References Cited

OTHER PUBLICATIONS

Uda et al., "Genome-wide association study shows BCL11A associated with persistent fetal hemoglobin and amelioration of the phenotype of thalassemia." PNAS 105(5):1620-1625 (2008).
Wang et al. "Genetic screens in human cells using the CRISPR/Cas9 system." Science 343(6166):80-84 (2013).
Wang et al. "Supplementary Material: Genetic screens in human cells using the CRISPR/Cas9 system." Science 343 (6166):80-84 (2013).
Wang et al., "In Vivo Delivery Systems for Therapeutic Genome Editing" International Journal of Molecular Sciences 17(5):1-19 (2016).
Wang et al., "Selection of hyperfunctional siRNAs with improved potency and specificity." Nucleic Acids Research 37 (22):e152 (2009).
White et al., "Factor VIII Gene and Hemophili A." Blood 73(1):1-12 (1989).
World Health Organization. "Sickle-cell anaemia. Report A59/9. Provisional agenda item 11.4." 59th World Health Assembly. www.who.int/gb/ebwha/pdf_files/WHA59/A59_9-en.pdf (2006).
Xu et al., "Correction of sickle cell disease in adult mice by interference with fetal hemoglobin silencing", Science 334 (6058):993-996 (2011).
Xu et al., "Reactivation of silenced human HbF in adult mice by inactivation of BCL11A." Blood 116: Abstract 643 (2010).
Xu et al., "Transcriptional silencing of beta-globin by BCL11A involvs long-range interactions and cooperation with SOX6." Genes and Development 24(8):783-798 (2010).
Yin et al., "Bcl11a Causes p21 Cip1 Down-Regulation and Transplantable Leukemia in Nf1-Deficient Mice." Blood 110 (11):2657-2657 (2007) [Abstract Only].
Yu et al., "Bcl11a is essential for lymphoid development and negatively regulates p53," J. Exp. Med. 2012 vol. 209 No. 13 2467-2483.
Zennou, V. et al., "HIV-1 genome nuclear import is mediated by a central DNA flap", Cell (2000), 101(2): 173-185.
Zufferey, R. et al., "Woodchuck hepatitis virus posttranscriptional regulatory element enhances expression of transgenes delivered by retroviral vectors." J Virol. (1999); 73(4): 2886-2892.
Brendel et al., "Lineage-specific BCL11A knockdown circumvents toxicities and reverses sickle phenotype," The Journal of Clinical Investigation, vol. 126, No. 10, Oct. 3, 2016, pp. 3868-3878.
Extended European Search Report dated Jan. 12, 2021, for European Application No. 18775163.1, 11 pages.
Kitowski, "A Lentiviral Vector Conferring Coregulated, Erythroid-Specific Expression of [gamma]-Globin and shRNA Sequences to BCL11A for the Treatment of Sickle Cell Disease," Jan. 1, 2006, 105 pages.
Mahajan et al., "Control of Beta Globin Genes," Journal of Cellular Biochemistry 102:801-810 (2007).

\* cited by examiner

FIGURE 9

| | D14 VCN (cdg) | Vector positive colonies (%) |
|---|---|---|
| MOCK | < 0.05 | 0 |
| bb694 | 3.1 | 82.5 |

VECTORS AND COMPOSITIONS FOR TREATING HEMOGLOBINOPATHIES

CROSS REFERENCE TO RELATED APPLICATIONS

This application is the National Stage of International Application No. PCT/US2018/025165, filed Mar. 29, 2018, which claims the benefit under 35 U.S.C. § 119(e) of U.S. Provisional Application No. 62/489,149, filed Apr. 24, 2017, and U.S. Provisional Application No. 62/478,375, filed Mar. 29, 2017, each of which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BLBD_085_02WO_ST25.txt. The text file is 12 KB, was created on Mar. 28, 2018, and is being submitted electronically via EFS-Web, concurrent with the filing of the specification.

BACKGROUND

Technical Field

The present disclosure generally relates, in part, to improved gene therapy vectors, compositions and methods of making the same.

Description of the Related Art

Hemoglobinopathies are a diverse group of inherited monogenetic blood disorders that result from variations in the structure and/or synthesis of hemoglobin. The most common hemoglobinopathies are sickle cell disease (SCD), α-thalassemia, and β-thalassemia. Approximately 5% of the world's population carries a globin gene mutation. The World Health Organization estimates that more than 300,000 infants are born each year with major hemoglobin disorders. Hemoglobinopathies manifest highly variable clinical manifestations that range from mild hypochromic anemia to moderate hematological disease to severe, lifelong, transfusion-dependent anemia with multiorgan involvement.

The only potentially curative treatment available for hemoglobinopathies is allogeneic hematopoietic stem cell transplantation. However, it is estimated that HLA-compatible HSC transplants are available to less than 20% of affected individuals and long term toxicities are substantial. In addition, HSC transplants are also associated with significant mortality and morbidity in subjects that have SCD or severe thalassemias. The significant mortality and morbidity is due in part to pre-HSC transplantation transfusion-related iron overload, graft-versus-host disease (GVHD), and high doses of chemotherapy/radiation required for pre-transplant conditioning of the subject, among others.

Recent progress in the field of gene therapy has raised the hope that patients afflicted with hemoglobinopathies such as β-thalassemia and sickle cell anemia will benefit from novel therapeutic approaches. Cavazzana-Calvo et al., *Nature* 2010. Transplantation of hematopoietic cells (HSCs) modified with lentiviral vectors carrying the β-globin gene has resulted in long-term correction of several mouse models of hemoglobin disorders, e.g., Imren et al., *Proc Natl Acad Sci USA*. 2002; 99(22):14380-14385; Malik et al., *Ann NY Acad Sci*. 2005; 1054:238-249; May et al., *Nature*. 2000; 406 (6791):82-86; Pawliuk et al., *Science*. 2001; 294(5550): 2368-2371). However, the Food and Drug Administration (FDA) has not yet approved any human gene therapy product for sale. Current gene therapy is experimental and has had mixed results in clinical trials. Ginn et al., *J Gene Med* 2013 and Naldini et al., *Nature Review* 2015.

BRIEF SUMMARY

Improved gene therapy vectors, compositions and methods of using the same to treat, prevent, or ameliorate at least one symptom of a hemoglobinopathy are contemplated herein.

In various embodiments, an HIV-1 lentiviral vector comprising an erythroid specific promoter operably linked to a polynucleotide encoding a shmiR that comprises an antisense sequence that hybridizes to a human BCL11A mRNA is contemplated.

In various embodiments, an HIV-1 strain NL4-3 lentiviral vector comprising a 5' long terminal repeat (LTR), an erythroid specific promoter operably linked to a polynucleotide encoding a shmiR that comprises an antisense sequence that hybridizes to a human BCL11A mRNA, and an HIV-1 strain NL4-3 3' LTR is contemplated.

In particular embodiments, the lentiviral vector comprises from 5' to 3', a Psi (Ψ) packaging signal; a lentiviral central polypurine tract (cPPT)/FLAP element; an RNA export element; and an HIV-1 env splice acceptor sequence.

In particular embodiments, the lentiviral vector comprises from 5' to 3', a Psi (Ψ) packaging signal; an HIV-1 strain NL4-3 central polypurine tract (cPPT)/FLAP element; an RNA export element; and an HIV-1 env splice acceptor sequence.

In certain embodiments, the lentiviral vector comprises a modified 5' long terminal repeat (LTR) and an HIV-1 3' SIN LTR.

In some embodiments, the lentiviral vector comprises a modified 5' LTR, wherein the promoter of the modified 5' LTR is replaced with a CMV promoter; and an HIV-1 3' SIN LTR.

In various embodiments, a lentiviral vector comprising: an HIV-1 strain NL4-3 5' long terminal repeat (LTR); an HIV-1 strain NL4-3 Psi (Ψ) packaging signal; an HIV-1 strain NL4-3 central polypurine tract (cPPT)/FLAP element; an RNA export element; an HIV-1 strain NL4-3 env splice acceptor sequence; an erythroid specific promotor operably linked to a shmiR that encodes an antisense sequence that hybridizes to a human BCL11A mRNA; and an HIV-1 strain NL4-3 3' LTR is contemplated.

In various embodiments, a lentiviral vector comprising: an HIV-1 5' long terminal repeat (LTR); a Psi (Ψ) packaging signal; a lentiviral central polypurine tract (cPPT)/FLAP element; an RNA export element; an HIV-1 env splice acceptor sequence; an erythroid specific promoter operably linked to a shmiR that encodes an antisense sequence that hybridizes to a human BCL11A mRNA; and an HIV-1 3' LTR is contemplated.

In particular embodiments, the lentiviral vector comprises a modified 5' LTR, wherein the promoter of the modified 5' LTR is replaced with a CMV promoter; and an HIV-1 3' SIN LTR.

In particular embodiments, the lentiviral vector comprises an RRE RNA export element.

In particular embodiments, the lentiviral vector comprises an RRE RNA export element isolated from HIV-1 strain HXB3.

In additional embodiments, the erythroid specific promotor comprises a β-globin promoter.

In further embodiments, the erythroid specific promotor comprises a human β-globin promoter.

In some embodiments, the lentiviral vector comprises a β-globin LCR.

In certain embodiments, the lentiviral vector comprises a human β-globin LCR.

In various embodiments, a self-inactivating (SIN) lentiviral vector comprising: a modified HIV-1 strain NL4-3 5' long terminal repeat (LTR), wherein the promoter of the modified 5' LTR is replaced with a CMV promoter; an HIV-1 strain NL4-3 Psi (Ψ) packaging signal; an HIV-1 strain NL4-3 cPPT/FLAP element; an HIV-1 strain HXB3 RRE RNA export element; an HIV-1 strain NL4-3 env splice acceptor sequence; a β-globin promotor operably linked to a shmiR that encodes an antisense sequence that hybridizes to a human BCL11A mRNA; a β-globin LCR; and an HIV-1 strain NL4-3 3' SIN LTR is contemplated.

In various embodiments, a self-inactivating (SIN) lentiviral vector comprising: a modified 5' long terminal repeat (LTR), wherein the promoter of the modified 5' LTR is replaced with a CMV promoter; a Psi (Ψ) packaging signal; a lentiviral central polypurine tract (cPPT)/FLAP element; an RRE RNA export element; an HIV-1 env splice acceptor sequence; a β-globin promoter operably linked to a shmiR that encodes an antisense sequence that hybridizes to a human BCL11A mRNA; a β-globin LCR; and an HIV-1 3' SIN LTR is contemplated.

In particular embodiments, the lentiviral vector comprises a human β-globin LCR comprising HS3 and HS2 DNAse I hypersensitivity sites.

In some embodiments, the lentiviral vector comprises a human β-globin LCR comprising HS3 and HS2 DNAse I hypersensitivity sites, but lacking an HS4 DNAse I hypersensitivity site.

In certain embodiments, the lentiviral vector comprises a polynucleotide of about 459 nucleotides that encodes a gag protein.

In particular embodiments, the lentiviral vector comprises a polynucleotide encoding the gag protein comprises one or more mutated ATG sequences.

In additional embodiments, the lentiviral vector comprises an HIV-1 env splice acceptor sequence of about 176 nucleotides.

In further embodiments, the lentiviral vector comprises a cPPT/FLAP element of about 381 nucleotides.

In some embodiments, the lentiviral vector comprises an HS2 DNAse I hypersensitive site of about 638 nucleotides.

In particular embodiments, the lentiviral vector comprises an HS3 DNAse I hypersensitive site of about 847 nucleotides.

In particular embodiments, the lentiviral vector comprises a synthetic poly(A) sequence disposed between an HIV-1 env splice acceptor sequence and the shmiR.

In certain embodiments, the shmiR encodes the sequence set forth in SEQ ID NO: 1.

In further embodiments, the shmiR comprises the guide strand sequence set forth in SEQ ID NO: 2.

In particular embodiments, the shmiR comprises a guide strand sequence that hybridizes to the target sequence set forth in SEQ ID NO: 3.

In some embodiments, an expression cassette comprising the erythroid specific promoter and the polynucleotide encoding the shmiR are in the reverse orientation compared to the transcription of the lentiviral genomic RNA.

In various embodiments, a lentiviral transfer vector comprising the polynucleotide sequence set forth in SEQ ID NO: 4 is contemplated.

In various embodiments, a cell comprising a lentiviral vector contemplated herein is provided.

In certain embodiments, a cell comprising one or more polynucleotides encoding HIV-1 gag and pol, VSV-G, and a lentiviral vector contemplated herein is provided.

In particular embodiments, lentiviral vector particle produced from a cell comprising one or more polynucleotides encoding HIV-1 gag and pol, VSV-G, and a lentiviral vector contemplated herein is provided.

In various embodiments, a cell transduced with a lentiviral vector contemplated herein is provided.

In some embodiments, the cell is transduced in the presence of an effective amount of a poloxamer selected from the group consisting of poloxamer 288, poloxamer 335, poloxamer 338, and poloxamer 407 and $PGE_2$ receptor agonist.

In various embodiments, a cell transduced with the lentiviral vector particle contemplated herein is provided.

In certain embodiments, the cell is transduced in the presence of an effective amount of a poloxamer selected from the group consisting of poloxamer 288, poloxamer 335, poloxamer 338, and poloxamer 407 and a $PGE_2$ receptor agonist.

In particular embodiments, the cell is a hematopoietic stem cell or hematopoietic progenitor cell.

In certain embodiments, the cell is a hematopoietic stem or progenitor cell.

In further embodiments, the cell is $CD34^+$.

In certain embodiments, the cell is $CD133^+$.

In particular embodiments, the cell is $CD34^+$ $CD38^{L_o}CD90^+CD45RA^-$.

In additional embodiments, the cell comprises one of more mutated β-globin alleles associated with a hemoglobinopathy.

In some embodiments, the cell comprises one of more mutated β-globin alleles selected from the group consisting of: $\beta^E/\beta^0$, $\beta^C/\beta^0$, $\beta^0/\beta^0$, $\beta^E/\beta^E$, $\beta^C/\beta^+$, $\beta^E/\beta^+$, $\beta^0/\beta^+$, $\beta^+/\beta^+$, $\beta^C/\beta^C$, $\beta^E/\beta^S$, $\beta^0/\beta^S$, $\beta^C/\beta^S$, $\beta^+/\beta^S$ and $\beta^S/\beta^S$.

In certain embodiments, the cell comprises one of more mutated β-globin alleles selected from the group consisting of: $\beta^E/\beta^0$, $\beta^C/\beta^0$, $\beta^0/\beta^0$, $\beta^C/\beta^C$, $\beta^E/\beta^E$, $\beta^E/\beta^+$, $\beta^C/\beta^E$, $\beta^C/\beta^+$, $\beta^0/\beta^+$, and $\beta^S/\beta^S$.

In particular embodiments, the cell comprises one of more mutated β-globin alleles selected from the group consisting of: $\beta^E/\beta^S$, $\beta^0/\beta^S$, $\beta^C/\beta^S$, $\beta^+/\beta^S$ and $\beta^S/\beta^S$.

In various embodiments, a population of cells comprising a plurality of the cells contemplated herein is provided.

In various embodiments, a composition comprising a population of cells comprising a plurality of the cells contemplated herein is provided.

In various embodiments, a pharmaceutical composition comprising a pharmaceutically acceptable carrier and a population of cells comprising a plurality of the cells contemplated herein is provided.

In various embodiments, a method of transducing a population of hematopoietic cells comprising culturing the cells in a culture medium, in the presence of a lentiviral vector contemplated herein; a poloxamer; and a $PGE_2$ receptor agonist is provided.

In some embodiments, the poloxamer is selected from the group consisting of: poloxamer 288, poloxamer 335, poloxamer 338, and poloxamer 407.

In particular embodiments, the PGE$_2$ receptor agonist is selected from the group consisting of: 15d-PGJ$_2$; delta12-PGJ$_2$; 2-hydroxyheptadecatrienoic acid (HET); Thromboxane A2; Thromboxane B2; Iloprost; Treprostinil; Travoprost; Carboprost tromethamine; Tafluprost; Latanoprost; Bimatoprost; Unoprostone isopropyl; Cloprostenol; Oestrophan; Superphan; Misoprostol; Butaprost; Linoleic Acid; 13(s)-HODE; LY171883; Mead Acid; Eicosatrienoic Acid; Epoxyeicosatrienoic Acid; ONO-259; Cay1039; a PGE$_2$ receptor agonist; 16,16-dimethyl PGE$_2$; 19(R)-hydroxy PGE$_2$; 16,16-dimethyl PGE$_2$ p-(p-acetamidobenzamido) phenyl ester; 11-deoxy-16,16-dimethyl PGE$_2$; 9-deoxy-9-methylene-16,16-dimethyl PGE$_2$; 9-deoxy-9-methylene PGE$_2$; Sulprostone; PGE$_2$ serinol amide; PGE$_2$ methyl ester; 16-phenyl tetranor PGE$_2$; 15(S)-15-methyl PGE$_2$; and 15(R)-15-methyl PGE$_2$.

In further embodiments, the PGE$_2$ receptor agonist is PGE$_2$ or 16,16-dimethyl PGE$_2$.

In certain embodiments, the lentiviral vector is present at an MOI of about 10 to about 30 or at an MOI of about 10 to about 25.

In particular embodiments, the lentiviral vector is present at an MOI of about 10 to about 20.

In some embodiments, the lentiviral vector is present at an MOI of about 10, about 11, about 12, about 13, about 14, about 15, about 16, about 17, about 18, about 19, about 20, about 21, about 22, about 23, about 24, about 25, about 26, about 27, about 28, about 29 or about 30.

In various embodiments, a method of treating a hemoglobinopathy in a subject comprising administering the subject an effective amount of a population of cells, a composition, or a pharmaceutical composition contemplated herein is provided.

In various embodiments, a method of ameliorating at least one symptom, of a hemoglobinopathy in a subject comprising administering the subject an effective amount of a population of cells, a composition, or a pharmaceutical composition contemplated herein is provided.

In particular embodiments, the β-globin alleles of the subject are $β^C/β^C$, $β^C/β^C$, $β^C/β^C$, $β^E/β^E$, $β^C/β^+$, $β^E/β^+$, $β^0/β^+$, $β^+/β^+$, $β^C/β^C$, $β^E/β^S$, $β^0/β^S$, $β^C/β^S$, $β^+/β^S$, and $β^S/β^S$.

In various embodiments, a method of treating a thalassemia in a subject comprising administering the subject an effective amount of a population of cells, a composition, or a pharmaceutical composition contemplated herein is provided.

In additional embodiments, the thalassemia is an α-thalassemia.

In certain embodiments, the thalassemia is a β-thalassemia.

In certain embodiments, the β-globin alleles of the subject are $β^E/β^0$, $β^C/β^0$, $β^0/β^0$, $β^C/β^C$, $β^E/β^E$, $β^E/β^+$, $β^C/β^E$, $β^C/β^+$, $β^0/β^+$, and $β^+/β^+$.

In various embodiments, a method of treating sickle cell disease in a subject comprising administering the subject an effective amount of a population of cells, a composition, or a pharmaceutical composition contemplated herein is provided.

In some embodiments, the β-globin alleles of the subject are $β^E/β^S$, $β^0/β^S$, $β^C/β^S$, $β^+/β^S$, and $β^S/β^S$.

In various embodiments, a method of treating a β-thalassemia in a subject comprising administering the subject an effective amount of a population of cells, a composition, or a pharmaceutical composition contemplated herein is provided.

In particular embodiments, the β-globin alleles of the subject are $β^E/β^0$, $β^C/β^0$, $β^0/β^0$, $β^C/β^C$, $β^E/β^E$, $β^E/β^+$, $β^C/β^E$, $β^C/β^+$, $β^0/β^+$, and $β^+/β^+$.

In certain embodiments, the population of hematopoietic stem cells is administered an intravenous route, an intramedullary route, or an intraosseous route.

In particular embodiments, the population of hematopoietic stem cells is administered intravenously.

BRIEF DESCRIPTION OF SEVERAL VIEWS OF THE DRAWINGS

FIG. 5 also shows the HbF and HbS levels from SCD CD34$^+$ cells transduced under various conditions and after day 14 erythroid differentiation culture (right panels).

FIG. 9 shows VCN and % LVV positive colonies of erythroid colonies plucked from mock transduced hCD34$^+$ cells or hCD34$^+$ cells transduced with bb694 lentiviral vector.

BRIEF DESCRIPTION OF THE SEQUENCE IDENTIFIERS

Figure 1:
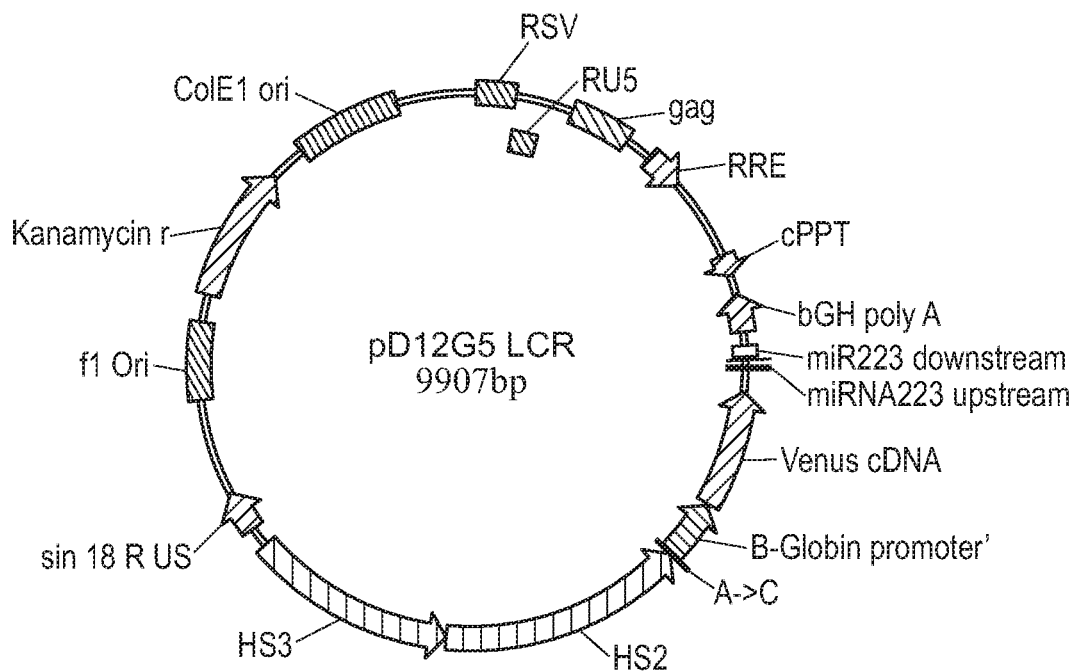
FIG. 1 shows vector maps of the D12G5 and BB694 lentiviral vectors.
Figure 1:
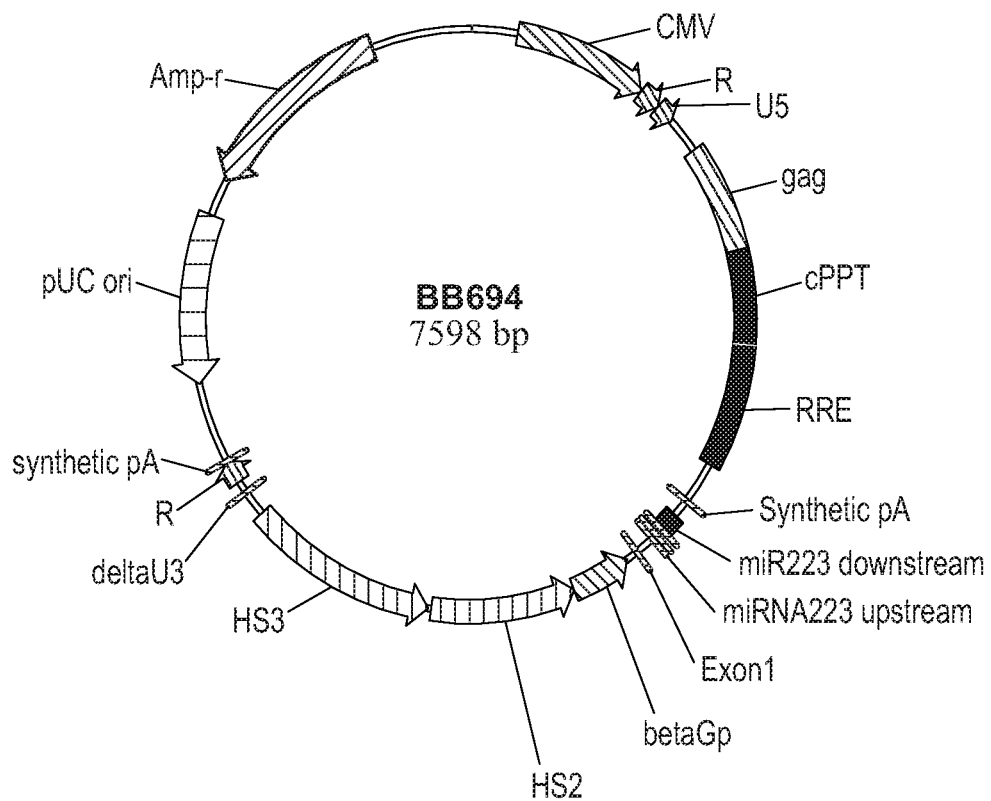

SEQ ID NO: 1 sets for the polynucleotide sequence of a shmirR.

SEQ ID NO: 2 sets for the polynucleotide sequence of a shmirR guide strand.

SEQ ID NO: 3 sets for the polynucleotide sequence of a shmirR target sequence.

SEQ ID NO: 4 sets for the polynucleotide sequence of the BB694 lentiviral vector.

DETAILED DESCRIPTION

A. Overview

The present disclosure generally relates to, in part, improved gene therapy vectors, compositions and methods of use for treating, preventing, or ameliorating at least one symptom of a hemoglobinopathy. Without wishing to be bound by any particular theory, the gene therapy compositions contemplated herein are used to increase the amount of fetal hemoglobin in a cell to treat, prevent, or ameliorates symptoms associated with various hemoglobinopathies. Thus, the compositions contemplated herein offer a potentially curative solution to subjects that have a hemoglobinopathy.

Normal adult hemoglobin comprises a tetrameric complex of two alpha-($\alpha$) globin proteins and two beta-($\beta$-) globin proteins. In development, the fetus produces fetal hemoglobin (HbF), which comprises two gamma-($\gamma$) globin proteins instead of the two $\beta$-globin proteins. At some point during perinatal development, a "globin switch" occurs; erythrocytes down-regulate $\gamma$-globin expression and switch to predominantly producing $\beta$-globin. This switch results primarily from decreased transcription of the $\gamma$-globin genes and increased transcription of $\beta$-globin genes. GATA binding protein-1 (GATA-1) is a transcription factor that influences globin switching. GATA-1 directly transactivates $\beta$-globin gene expression and indirectly represses or suppresses $\gamma$-globin gene expression through transactivation of B Cell CLL/Lymphoma 11A gene (BCL11A) expression. Pharmacologic or genetic manipulation of the switch represents an attractive therapeutic strategy for patients who suffer from $\beta$-thalassemia or sickle-cell disease due to mutations in the $\beta$-globin gene.

In various embodiments, the gene therapy vectors contemplated herein are improved lentiviral vectors encoding a polynucleotide that decreases BCL11A expression in erythroid cells. Without wishing to be bound by any particular theory, it is contemplated that reducing or eliminating BCL11A expression in erythroid cells would result in the reactivation or derepression of $\gamma$-globin gene expression and a decrease in $\beta$-globin gene expression, and thereby increase HbF expression to effectively treat and/or ameliorate one or more symptoms associated with subjects that have a hemoglobinopathy.

In various embodiments, gene therapy compositions comprise one or more cells comprising a lentiviral vector encoding an inhibitory RNA designed to bind and cleave a BCL11A mRNA. In particular embodiments, a lentiviral vector encodes an siRNA, an shRNA, a piRNA, a miRNA, or combination thereof. In preferred embodiments, a lentiviral vector encodes an shRNA embedded in a miRNA scaffold, i.e., a shmiR. In further preferred embodiments, a lentiviral vector comprises an shRNA directed against BCL11A that is embedded in a hsa-miR-223 scaffold. In particular embodiments, the lentiviral vector LTRs, cPPT/FLAP, and env S/A sequences are isolated from HIV-1 strain NL4-3. In particular embodiments, the lentiviral RNA export element is an RRE element isolated from HIV-1 strain HXB3.

In various other embodiments, a population of cells comprising one or more hematopoietic cells transduced with a lentiviral vector contemplated herein, is provided. In preferred embodiments, the cells comprise one or more mutated $\beta$-globin alleles associated with a hemoglobinopathy. Without wishing to be bound by any particular theory, it is contemplated that modified hematopoietic cells, comprising one or more mutated $\beta$-globin alleles associated with a hemoglobinopathy and further comprising a lentiviral vector contemplated herein, have decreased BCL11A expression, decreased defective $\beta$-globin expression, and increased $\gamma$-globin expression, thereby providing a therapeutic cellular composition.

In particular embodiments, methods for treating a subject diagnosed with, or having, a hemoglobinopathy are contemplated comprising administering to the subject an effective amount of cells modified with one or more lentiviral vectors contemplated herein.

Various embodiments contemplated herein will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); Short Protocols in Molecular Biology: A Compendium of Methods from *Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology*; as well as monographs in journals such as *Advances in Immunology*.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. As used herein, the terms "include" and "comprise" are used synonymously. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., lentiviral vectors.

As will be evident to one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The term "viral vector" may refer either to a virus or viral particle capable of transferring a nucleic acid into a cell or to the transferred nucleic acid itself. Viral vectors and transfer plasmids contain structural and/or functional genetic elements that are primarily derived from a virus. The term "lentiviral vector" refers to a retroviral vector or plasmid containing structural and functional genetic elements, or portions thereof, including LTRs that are primarily derived from a lentivirus.

The terms "lentiviral vector" and "lentiviral expression vector" may be used to refer to lentiviral transfer plasmids and/or infectious lentiviral particles in particular embodiments. Where reference is made herein to elements such as cloning sites, promoters, regulatory elements, heterologous nucleic acids, etc., it is to be understood that the sequences of these elements are present in RNA form in the lentiviral particles contemplated herein and are present in DNA form in the DNA plasmids contemplated herein.

The term "long terminal repeat (LTR)" refers to domains of base pairs located at the ends of retroviral DNAs which, in their natural sequence context, are direct repeats and contain U3, R and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R and U5. The U3 region contains the enhancer and promoter elements. The U5 region is the sequence between the primer binding site and the R region and contains the polyadenylation sequence. The R (repeat) region is flanked by the U3 and U5 regions. The LTR composed of U3, R and U5 regions and appears at both the 5' and 3' ends of the viral genome. Adjacent to the 5' LTR are sequences necessary for reverse transcription of the genome (the tRNA primer binding site) and for efficient packaging of viral RNA into particles (the Psi site). Proviral inserts comprise two copies of the 3' viral LTR, one copy that replaces the 5' viral LTR and the 3' viral LTR.

As used herein, the term "packaging signal" or "packaging sequence" refers to sequences located within the retroviral genome which are required for insertion of the viral RNA into the viral capsid or particle, see e.g., Clever et al., 1995. J. of Virology, Vol. 69, No. 4; pp. 2101-2109. Several retroviral vectors use the minimal packaging signal (also referred to as the psi [Ψ] or [Ψ+] sequence) needed for encapsidation of the viral genome. Thus, as used herein, the terms "packaging sequence," "packaging signal," "psi" and the symbol "Ψ," are used in reference to the non-coding sequence required for encapsidation of retroviral RNA strands during viral particle formation.

As used herein, the term "modified LTR" refers to one or more nucleotide additions, deletions or substitutions in the native HIV-1 5' LTR and/or 3' LTRs. The skilled artisan would be able to determine whether an LTR is modified by comparison to a reference LTR.

As used herein, the term "replication-defective" refers to a lentivirus comprising a modified 5' LTR and/or 3' LTR that improves the safety of lentiviral system by rendering the lentivirus replication-defective.

"Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication. Self-inactivation is preferably achieved through in the introduction of a deletion in the U3 region of the 3' LTR of the vector DNA, i.e., the DNA used to produce the vector RNA. Thus, during reverse transcription, this deletion is transferred to the 5' LTR of the proviral DNA. In the case of HIV based lentivectors, it has been discovered that such vectors tolerate significant U3 deletions, including the removal of the LTR TATA box (e.g., deletions from −418 to −18), without significant reductions in vector titers.

As used herein, the term "chimeric 5' LTR" refers to a 5' LTR wherein the U3 region has been replaced by a heterologous promoter, e.g., CMV promoter, to drive transcription of the viral genome during production of viral particles. The promoters are able to drive high levels of transcription in a Tat-independent manner. This replacement reduces the possibility of recombination to generate replication-competent virus because there is no complete U3 sequence in the virus production system.

The term "TAR" refers to the "trans-activation response" genetic element located in the R region of lentiviral (e.g., HIV) LTRs. This element interacts with the lentiviral trans-activator (tat) genetic element to enhance viral replication. However, this element is not required in embodiments wherein the U3 region of the 5' LTR is replaced by a heterologous promoter.

The "R region" refers to the region within retroviral LTRs beginning at the start of the capping group (i.e., the start of transcription) and ending immediately prior to the start of the poly A tract. The R region is also defined as being flanked by the U3 and U5 regions. The R region plays a role during reverse transcription in permitting the transfer of nascent DNA from one end of the genome to the other.

As used herein, the term "FLAP element" refers to a nucleic acid whose sequence includes the central polypurine tract and central termination sequences (cPPT and CTS) of a retrovirus, e.g., HIV-1 or HIV-2. In some embodiments, the terms "FLAP element" and "cPPT/FLAP" are used interchangeably to refer to the foregoing FLAP element. Suitable FLAP elements are described in U.S. Pat. No. 6,682,907 and in Zennou, et al., 2000, Cell, 101:173. During HIV-1 reverse transcription, central initiation of the plus-strand DNA at the central polypurine tract (cPPT) and central termination at the central termination sequence (CTS) lead to the formation of a three-stranded DNA structure: the HIV-1 central DNA flap. While not wishing to be bound by any theory, the DNA flap may act as a cis-active determinant of lentiviral genome nuclear import and/or may increase the titer of the virus. In one embodiment, a vector of the invention comprises a FLAP element isolated from HIV-1 strain NL4-3.

The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. J. Virol. 65: 1053; and Cullen et al., 1991. Cell 58: 423), and the hepatitis B virus post-transcriptional regulatory element (HPRE). Generally, the RNA export element is placed within the 3' UTR of a gene, and can be inserted as one or multiple copies.

As used herein, the terms "posttranscriptional regulatory element" or "PRE" refer to a cis-acting element that regulates expression at the mRNA level by, for example, regulating capping, splicing, poly(A) tail addition, and mRNA stability. Illustrative examples of PTE include, but are not limited to, woodchuck hepatitis virus posttranscriptional regulatory element (WPRE; Zufferey et al., 1999, J. Virol., 73:2886); the posttranscriptional regulatory element present in hepatitis B virus (HPRE) (Huang and Yen, 1995, Mol. Cell. Biol., 5:3864); and the like (Liu et al., 1995, Genes Dev., 9:1766).

The term "poly(A) site" or "poly(A) sequence" as used herein denotes a DNA sequence which directs both the termination and polyadenylation of the nascent RNA transcript by RNA polymerase II. Polyadenylation sequences can promote mRNA stability by addition of a poly(A) tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is a synthetic poly(A) sequence (e.g., AATAAA, ATTAAA, AGTAAA). Illustrative examples of poly(A) sequences include, but are not limited to an SV40 poly(A) sequence, a bovine growth hormone poly(A) sequence (BGHpA), a rabbit β-globin poly(A) sequence (rβgpA), or another suitable heterologous or endogenous poly(A) sequence known in the art.

"Transfection" refer to the process of introducing naked DNA into cells by non-viral methods.

"Infection" refers to the process of introducing foreign DNA into cells using a viral vector.

"Transduction" refers to the introduction of foreign DNA into a cell's genome using a viral vector.

"Vector copy number" or "VCN" refers to the number of copies of a vector, or portion thereof, in a cell's genome. The average VCN may be determined from a population of cells or from individual cell colonies. Exemplary methods for determining VCN include polymerase chain reaction (PCR) and flow cytometry.

"Transduction efficiency" refers to the percentage of cells transduced with at least one copy of a vector. For example if $1\times10^6$ cells are exposed to a virus and $0.5\times10^6$ cells are determined to have a least one copy of a virus in their genome, then the transduction efficiency is 50%. Exemplary methods for determining transduction efficiency include PCR and flow cytometry.

A "small molecule," "small organic molecule," or "small molecule compound" refers to a low molecular weight compound that has a molecular weight of less than about 5 kD, less than about 4 kD, less than about 3 kD, less than about 2 kD, less than about 1 kD, or less than about 0.5 kD. In particular embodiments, small molecules can include, nucleic acids, peptides, peptidomimetics, peptoids, other small organic compounds or drugs, and the like. Libraries of chemical and/or biological mixtures, such as fungal, bacterial, or algal extracts, are known in the art and can be screened with any of the assays of the invention. Examples of methods for the synthesis of molecular libraries can be found in: (Carell et al., 1994a; Carell et al., 1994b; Cho et al., 1993; DeWitt et al., 1993; Gallop et al., 1994; Zuckermann et al., 1994).

The term "analog" or "derivative" relates to a molecule that is similar to another chemical substance in structure and function, often differing structurally by a single element or group, but may differ by differ by modification of more than one group (e.g., 2, 3, or 4 groups) if it retains the same function as the parental chemical. Such modifications are routine to persons skilled in the art, and include, for example, additional or substituted chemical moieties, such as esters or amides of an acid, protecting groups such as a benzyl group for an alcohol or thiol, and tert-butoxylcarbonyl groups for an amine. Also included are modifications to alkyl side chains, such as alkyl substitutions (e.g., methyl, dimethyl, ethyl, etc.), modifications to the level of saturation or unsaturation of side chains, and the addition of modified groups such as substituted phenyl and phenoxy. Derivatives may also include conjugates, such as biotin or avidin moieties, enzymes such as horseradish peroxidase and the like, and including radio-labeled, bioluminescent, chemoluminescent, or fluorescent moieties. Also, moieties may be added to the agents described herein to alter their pharmacokinetic properties, such as to increase half-life in vivo or ex vivo, or to increase their cell penetration properties, among other desirable properties. Also included are prodrugs, which are known to enhance numerous desirable qualities of pharmaceuticals (e.g., solubility, bioavailability, manufacturing, etc.) (see, e.g., WO/2006/047476 for exemplary EP agonist prodrugs, which is incorporated by reference for its disclosure of such agonists).

As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), RNA, short interfering RNA (siRNA), short hairpin RNA (shRNA), microRNA (miRNA), shRNA embedded microRNA (shmiR) ribozymes, genomic RNA (gRNA), plus strand RNA (RNA(+)), minus strand RNA (RNA(−)), tracrRNA, crRNA, single guide RNA (sgRNA), synthetic RNA, synthetic mRNA, genomic DNA (gDNA), PCR amplified DNA, complementary DNA (cDNA), synthetic DNA, or recombinant DNA. Preferably, polynucleotides of the invention include polynucleotides or variants having at least about 50%, 55%, 60%, 65%, 70%, 75%, 80%, 85%, 90%, 95%, 96%, 97%, 98%, 99% or 100% sequence identity to any of the reference sequences described herein (see, e.g., SEQ ID NOs: 1-4), typically where the variant maintains at least one biological activity of the reference sequence. In various illustrative embodiments, viral vector and transfer plasmid polynucleotide sequences and compositions comprising the same are contemplated. In particular embodiments, polynucleotides encoding one or more therapeutic polypeptides and/or other genes of interest are contemplated. In particular embodiments, lentiviral vectors contemplated herein comprise an inhibitory RNA that hybridizes to a BCL11A mRNA, see e.g., SEQ ID NOs: 1-2.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms include polynucleotides in which one or more nucleotides have been added or deleted, or replaced with different nucleotides compared to a reference polynucleotide. In this regard, it is well understood in the art that certain alterations inclusive of mutations, additions, deletions and substitutions can be made to a reference polynucleotide whereby the altered polynucleotide retains the biological function or activity of the reference polynucleotide.

As used herein, the term "isolated" means material, e.g., a polynucleotide, a polypeptide, a cell, that is substantially or essentially free from components that normally accompany it in its native state. In particular embodiments, the term "obtained" or "derived" is used synonymously with isolated. For example, an "isolated polynucleotide," as used herein, refers to a polynucleotide that has been purified from the sequences which flank it in a naturally-occurring state, e.g., a DNA fragment that has been removed from the sequences that are normally adjacent to the fragment.

As used herein, the terms "shRNA" or "short hairpin RNA" refer to double-stranded structure that is formed by a single self-complementary RNA strand.

As used herein, the terms "miRNA" or "microRNA" refer to small non-coding RNAs of 20-22 nucleotides, typically excised from 70 nucleotide foldback RNA precursor structures known as pre-miRNAs. miRNAs negatively regulate their targets in one of two ways depending on the degree of complementarity between the miRNA and the target. First, miRNAs that bind with perfect or nearly perfect complementarity to protein-coding mRNA sequences induce the RNA-mediated interference (RNAi) pathway. miRNAs that exert their regulatory effects by binding to imperfect complementary sites within the 3' untranslated regions (UTRs) of their mRNA targets, repress target-gene expression post-transcriptionally, apparently at the level of translation, through a RISC complex that is similar to, or possibly identical with, the one that is used for the RNAi pathway. Consistent with translational control, miRNAs that use this mechanism reduce the protein levels of their target genes, but the mRNA levels of these genes are only minimally affected.

As used herein, the terms "shRNA embedded miRNA," "shmiR," and "schmir" are used interchangeably and refer to an shRNA whose sense and antisense strands are embedded into an miRNA scaffold, which retains the miRNA flanking regions and loop. For example, in one embodiment, the skilled artisan can design a short hairpin RNA expressed from a miR-223 primary transcript. This design adds a Drosha processing site to the shRNA construct and has been shown to greatly increase knockdown efficiency (Pusch et al., 2004). In particular embodiments, the hairpin stem of a shmir comprises 21-nt of dsRNA and a 15-nt loop from a human miRNA. Adding the miRNA loop and flanking sequences on either or both sides of the hairpin results in greater than 10-fold increase in Drosha and Dicer processing of the expressed hairpins when compared with conventional shRNA designs without microRNA. Increased Drosha and Dicer processing translates into greater siRNA/miRNA production and greater potency for expressed hairpins. In preferred embodiments, a shmir comprises a 21-nt guide strand, wherein about 17-nt correspond to an antisense RNA that binds a target mRNA and about 4-nt correspond to GC-rich sequences, e.g., GCGC, that improve 3'-end thermodynamic stability in the RNA duplex and promotes preferential RISC loading of the intended guide strand. See, e.g., SEQ ID NOs: 1-3. In one embodiment, the polynucleotide encodes a shmiR. In various other embodiments, a polynucleotide comprises a polynucleotide encoding a polypeptide a shmiR.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation.

The terms "complementary" and "complementarity" refer to polynucleotides (i.e., a sequence of nucleotides) related by the base-pairing rules. For example, the complementary strand of the DNA sequence 5' A G T C A T G 3' is 3' T C A G T A C 5'. The latter sequence is often written as the reverse complement with the 5' end on the left and the 3' end on the right, 5' C A T G A C T 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

The term "nucleic acid cassette" or "expression cassette" as used herein refers to genetic sequences within the vector which can express a polynucleotide. In one embodiment, the nucleic acid cassette contains a polynucleotide(s)-of-interest. In another embodiment, the nucleic acid cassette contains one or more expression control sequences, e.g., a promoter, enhancer, poly(A) sequence, and a polynucleotide(s)-of-interest. Vectors may comprise one, two, three, four, five or more nucleic acid cassettes. The nucleic acid cassette is positionally and sequentially oriented within the vector such that the nucleic acid in the cassette can be transcribed into RNA. Preferably, the cassette has its 3' and 5' ends adapted for ready insertion into a vector, e.g., it has restriction endonuclease sites at each end. In a preferred embodiment, the nucleic acid cassette one or more expression control sequences operably linked to a polynucleotide encoding a therapeutic RNA, e.g., a shmiR, and/or a polypeptide, that can be used to treat, prevent, or ameliorate a genetic disorder. The cassette can be removed and inserted into a plasmid or viral vector as a single unit.

As used herein, the term "polynucleotide(s)-of-interest" refers to one or more polynucleotides, e.g., a polynucleotide encoding a polypeptide (i.e., a polypeptide-of-interest), inserted into an expression vector that is desired to be expressed. In preferred embodiments, vectors and/or plasmids of the present invention comprise one or more polynucleotides-of-interest that encode one or more therapeutic RNAs, e.g., shRNAs, miRNAs, or shmiRs, and/or therapeutic polypeptides, e.g., a globin. In particular embodiments, the polynucleotide-of-interest is a transgene that encodes a BCL11A shmiR and a polypeptide that provides a therapeutic function for the treatment of a hemoglobinopathy, e.g., α-globin, β-globin or β-globinA-T87Q. Illustrative examples of globin polynucleotide sequences suitable for use in exemplary embodiments include, but are not limited to, polynucleotides encoding α-globin, β-globin, β-globinA-T87Q, anti-sickling globins, γ-globin, and δ globin.

The term "globin" as used herein refers to proteins or protein subunits that are capable of covalently or noncovalently binding a heme moiety, and can therefore transport or store oxygen. Subunits of vertebrate and invertebrate hemoglobins, vertebrate and invertebrate myoglobins or mutants thereof are included by the term globin. The term excludes hemocyanins. Examples of globins include α-globin or variant thereof, β-globin or variant thereof, a γ-globin or a variant thereof, and δ-globin or a variant thereof.

Polynucleotides, regardless of the length of the coding sequence itself, may be combined with other DNA sequences, such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, with the total length preferably being limited by the ease of preparation and use in the intended recombinant DNA protocol.

The term "expression control sequence" refers to a polynucleotide sequence that comprises one or more promoters, enhancers, or other transcriptional control elements or combinations thereof that are capable of directing, increasing, regulating, or controlling the transcription or expression of an operatively linked polynucleotide. In particular embodiments, vectors of the invention comprise one or more expression control sequences that are specific to particular erythroid cells, erythroid cell types, or erythroid cell lineages. In preferred embodiments, vectors comprise one or more expression control sequences specific to erythroid cells, e.g., an erythroid specific expression control sequence.

An "endogenous" expression control sequence is one which is naturally linked to a given gene in the genome. An "exogenous" expression control sequence is one which is placed in juxtaposition to a gene by means of genetic manipulation (i.e., molecular biological techniques) such that transcription of that gene is directed by the linked enhancer/promoter. A "heterologous" expression control sequence is an exogenous sequence that is from a different species than the cell being genetically manipulated. A "synthetic" expression control sequence may comprise elements of one more endogenous and/or exogenous sequences, and/or sequences determined in vitro or in silico that provide optimal promoter and/or enhancer activity for the particular gene therapy. In particular embodiments, a vector comprises exogenous, endogenous, or heterologous expression control sequences such as promoters and/or enhancers.

The term "promoter" as used herein refers to an expression control sequence that comprises a recognition site of a polynucleotide (DNA or RNA) to which an RNA polymerase binds. The term "enhancer" refers to an expression control sequence that comprises a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer or other expression control sequence) and a second polynucleotide sequence, e.g., a polynucleotide-of-interest, wherein the expression control sequence directs transcription of the nucleic acid corresponding to the second sequence.

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. Illustrative examples of polypeptides include, but are not limited to globin polypeptides, suitable for use in the compositions and methods of particular embodiments. Also, see, e.g., U.S. Pat. Nos. 6,051,402; 7,901,671; and 9,068,199, the full disclosure and claims of which are specifically incorporated herein by reference in their entireties.

Particular embodiments contemplated herein, also include polypeptide "variants." The recitation polypeptide "variant" refers to polypeptides that are distinguished from a reference polypeptide by the addition, deletion, truncations, modifications, and/or substitution of at least one amino acid residue, and that retain a biological activity. In certain embodiments, a polypeptide variant is distinguished from a reference polypeptide by one or more substitutions, which may be conservative or non-conservative, as known in the art. In certain embodiments, a variant polypeptide includes an amino acid sequence having at least about 50%, 55%, 60%, 65%, 70%, 75%, 80%, 85%, 90%, 91%, 92%, 93%, 94%, 95%, 96%, 97%, 98%, 99% or more sequence identity or similarity to a corresponding sequence of a reference polypeptide. In certain embodiments, amino acid additions or deletions occur at the C-terminal end and/or the N-terminal end of the reference polypeptide.

A "host cell" includes cells transfected, infected, or transduced in vivo, ex vivo, or in vitro with a recombinant vector or a polynucleotide contemplated herein. Host cells may include packaging cells, producer cells, and cells infected with viral vectors. In particular embodiments, host cells infected with viral vector of the invention are administered to a subject in need of therapy. In certain embodiments, the term "target cell" is used interchangeably with host cell and refers to transfected, infected, or transduced cells of a desired cell type. In preferred embodiments, the target cell is a stem cell or progenitor cell. In certain preferred embodiments, the target cell is a somatic cell, e.g., adult stem cell, progenitor cell, or differentiated cell. In particular preferred embodiments, the target cell is a hematopoietic cell, e.g., a hematopoietic stem or progenitor cell. Further therapeutic target cells are discussed, infra.

The term "primary cell" as used herein is known in the art to refer to a cell that has been isolated from a tissue and has been established for growth in vitro or ex vivo. Corresponding cells have undergone very few, if any, population doublings and are therefore more representative of the main functional component of the tissue from which they are derived in comparison to continuous cell lines, thus representing a more representative model to the in vivo state. Methods to obtain samples from various tissues and methods to establish primary cell lines are well-known in the art (see, e.g., Jones and Wise, *Methods Mol Biol*. 1997). Primary cells for use in the method of the invention are derived from, e.g., blood. In one embodiment, the primary cell is a hematopoietic stem or progenitor cell.

The term "stem cell" refers to a cell which is an undifferentiated cell capable of (1) long term self-renewal, or the ability to generate at least one identical copy of the original cell, (2) differentiation at the single cell level into multiple, and in some instance only one, specialized cell type and (3) of in vivo functional regeneration of tissues. Stem cells are subclassified according to their developmental potential as totipotent, pluripotent, multipotent and oligo/unipotent. "Self-renewal" refers a cell with a unique capacity to produce unaltered daughter cells and to generate specialized cell types (potency). Self-renewal can be achieved in two ways. Asymmetric cell division produces one daughter cell that is identical to the parental cell and one daughter cell that is different from the parental cell and is a progenitor or differentiated cell. Symmetric cell division produces two identical daughter cells. "Proliferation" or "expansion" of cells refers to symmetrically dividing cells.

As used herein, the term "progenitor" or "progenitor cells" refers to cells have the capacity to self-renew and to differentiate into more mature cells. Many progenitor cells differentiate along a single lineage, but may have quite extensive proliferative capacity.

The term "hematopoietic stem cell" or "HSC" refers to multipotent stem cells that give rise to the all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See Fei, R., et al., U.S. Pat. No. 5,635,387; McGlave, et al., U.S. Pat. No. 5,460,964; Simmons, P., et al., U.S. Pat. No. 5,677,136; Tsukamoto, et al., U.S. Pat. No. 5,750,397; Schwartz, et al., U.S. Pat. No. 5,759,793; DiGuisto, et al., U.S. Pat. No. 5,681,599; Tsukamoto, et al., U.S. Pat. No. 5,716,827). When transplanted into lethally irradiated animals or humans, hematopoietic stem and progenitor cells can repopulate the erythroid, neutrophil-macrophage, megakaryocyte and lymphoid hematopoietic cell pool.

By "enhance" or "promote," or "increase" or "expand" refers generally to the ability of the compositions and/or methods contemplated herein to elicit, cause, or produce increased HbF levels, increase γ-globin expression, and/or increased transduction efficiency compared to either vehicle or control compositions. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) a reference amount.

By "decrease" or "lower," or "lessen," or "reduce," or "abate" refers generally to compositions or methods that elicit, cause, or reduce abnormal globin levels, decrease β-globin gene expression levels, and/or decrease BCL11A gene expression levels. A "decreased" or "reduced" amount is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) a reference amount.

By "maintain," or "preserve," or "maintenance," or "no change," or "no substantial change," or "no substantial decrease" refers generally to a physiological response that is comparable to a response caused by either vehicle, a control molecule/composition, or the response in a particular cell. A comparable response is one that is not significantly different or measurable different from the reference response.

In the following description, certain specific details are set forth in order to provide a thorough understanding of various illustrative embodiments of the invention contemplated herein. However, one skilled in the art will understand that particular illustrative embodiments may be practiced without these details.

C. BCL11A ShmiR Lentiviral Vectors

The lentiviral vectors contemplated herein provide a much needed solution to the problem of efficiently transducing and expressing therapeutic RNAs in erythroid cells in order to treat, prevent, or ameliorate at least one symptom of a hemoglobinopathic disorder. The improved lentiviral vector architectures of the lentiviral vectors contemplated herein result in increased vector titer, increased transducibility, increased vector copy number, and increased transduction efficiency compared to existing lentiviral vector architectures.

In particular embodiments, the lentiviral vector comprises one or more erythroid cell expression control sequences operably linked to a polynucleotide encoding a BCL11A shmiR. The shmiR comprises an miRNA scaffold, which retains the miRNA flanking regions and loop, and optimized passenger and guide strands from an shRNA construct that targets BCL11A. Without wishing to be bound by any particular theory, the addition of GCGC to the 3' end of the guide strand is contemplated to increase 3'-end thermodynamic stability in the RNA duplex, which should promote preferential RISC loading of the intended guide strand.

In preferred embodiments, the lentiviral vector is an HIV-1 strain NL4-3 lentiviral vector wherein all native lentiviral vector sequences except the RRE are derived from the HIV-1 strain NL4-3. In particular embodiments, the lentiviral vectors contemplated herein comprise one or more differences compared to existing lentiviral vector architectures that encode BCL11A shmiRs. The one or more differences enable the lentiviral vectors contemplated herein to outperform the existing lentiviral vectors and yield an improved gene therapy product. Illustrative examples of the one or more differences include, but are not limited to: the lentiviral vector LTR, cPPT/FLAP, and env S/A sequences are isolated from the HIV-1 strain NL4-3; the RRE sequence is isolated from HIV-1 strain HXB3; the architecture of the lentiviral vector elements is 5' LTR-psi (Ψ) packaging signal-cPPT/FLAP-RRE-env splice acceptor (S/A) site; the lentiviral vector comprises a 5' LTR, wherein the endogenous promoter has been replaced with a CMV promoter; the lentiviral vector comprises a polynucleotide encoding a truncated gag protein of about 459 nucleotides and that has at least two mutated ATG codons; the lentiviral vector comprises an env splice acceptor (S/A) site of about 176 nucleotides; the lentiviral vector comprises a cPPT/FLAP sequence of about 381 nucleotides; the lentiviral vector comprises a β-globin LCR HS2 DNAse I hypersensitive site of about 638 nucleotides; the lentiviral vector comprises a β-globin LCR HS3 DNAse I hypersensitive site of about 847 nucleotides; and the lentiviral vector comprises a synthetic polyadenylation sequence at the 3' end of the shmiR expression cassette.

The lentiviral vectors contemplated in particular embodiments comprise an erythroid specific promoter selected from the group consisting of: a human β-globin promoter; a human β-globin LCR; and a human α-globin HS40 enhancer and an ankyrin-1 promoter, operably linked to a polynucleotide encoding a shmiR designed to hybridize and facilitate cleavage of a BCL11A mRNA, i.e., a BCL11A shmiR.

The lentiviral vector architecture of lentiviral vectors contemplated herein comprises from 5' to 3', a Psi (Ψ) packaging signal; a lentiviral central polypurine tract (cPPT)/FLAP element, optionally wherein the cPPT/FLAP element comprises a polynucleotide sequence of about 381 nucleotides in length and further comprises a cPPT element and a CTS sequence; an RNA export element, optionally wherein the RNA export element is a REV response element or RRE; and an HIV-1 env splice acceptor sequence.

Lentiviral vector safety is of paramount importance for any potential lentiviral gene therapy. The lentiviral vectors contemplated herein comprise one or more modifications, including but not limited to modifications to the one or more LTRs, to render the lentivirus replication-defective. In particular embodiments, the lentivirus comprises a modified 5' long terminal repeat (LTR), wherein the modification comprises replacing the endogenous promoter of the 5' LTR with a heterologous CMV promoter. In particular embodiments, the lentivirus comprises a modified 3' LTR, wherein the modification comprises deletion of the viral promoters and enhancers in the U3 region of the 3' LTR, optionally wherein the deletion is about 400 nucleotides in length.

In particular embodiments, a lentiviral vector contemplated herein comprises an HIV-1 strain NL4-3 5' LTR, wherein the U3 region has been replaced with a CMV promoter; a Psi (Ψ) packaging signal; an HIV-1 strain NL4-3 central polypurine tract (cPPT)/FLAP element comprising a cPPT element and a CTS sequence; an HIV-1 strain HXB3 RRE RNA export element, an HIV-1 strain NL4-3 env splice acceptor sequence; an erythroid specific promotor operably linked to a shmiR that encodes an RNA sequence that hybridizes to a human BCL11A mRNA; and an HIV-1 strain NL4-3 3' SIN LTR.

In particular embodiments, a lentiviral vector contemplated herein comprises an HIV-1 strain NL4-3 5' LTR, wherein the U3 region has been replaced with a CMV promoter; a Psi (Ψ) packaging signal; an HIV-1 strain NL4-3 central polypurine tract (cPPT)/FLAP element comprising a cPPT element and a CTS sequence; an HIV-1 strain HXB3 RRE RNA export element, an HIV-1 strain NL4-3 env splice acceptor sequence; a human β-globin LCR and human β-globin promoter operably linked to a shmiR that encodes an RNA sequence that hybridizes to a human BCL11A mRNA; and an HIV-1 strain NL4-3 3' SIN LTR.

In particular embodiments, a lentiviral vector contemplated herein comprises an HIV-1 strain NL4-3 5' LTR, wherein the U3 region has been replaced with a CMV promoter; a Psi (Ψ) packaging signal; an HIV-1 strain NL4-3 central polypurine tract (cPPT)/FLAP element comprising a cPPT element and a CTS sequence; an HIV-1 strain HXB3 RRE RNA export element, an HIV-1 strain NL4-3 env splice acceptor sequence; an HS3 and HS2 DNAseI hypersensitive sites from the human β-globin LCR and human β-globin promoter operably linked to a shmiR that encodes an RNA sequence that hybridizes to a human BCL11A mRNA; and an HIV-1 strain NL4-3 3' SIN LTR.

In particular embodiments, a lentiviral vector contemplated herein comprises an HIV-1 strain NL4-3 5' LTR, wherein the U3 region has been replaced with a CMV promoter; a Psi (Ψ) packaging signal; a polynucleotide encoding a truncated gag protein and comprising one or more one or more mutated ATG codons; an HIV-1 strain NL4-3 central polypurine tract (cPPT)/FLAP element comprising a cPPT element and a CTS sequence; an HIV-1 strain HXB3 RRE RNA export element, an HIV-1 strain NL4-3 env splice acceptor sequence; an HS3 and HS2 DNAseI hypersensitive sites from the human β-globin LCR and human β-globin promoter operably linked to a shmiR that encodes an RNA sequence that hybridizes to a human BCL11A mRNA, and a synthetic poly(A) signal; and an HIV-1 strain NL4-3 3' SIN LTR.

In particular embodiments, a lentiviral vector contemplated herein comprises an HIV-1 strain NL4-3 5' LTR, wherein the U3 region has been replaced with a CMV promoter; a Psi (Ψ) packaging signal; a polynucleotide encoding a truncated gag protein and comprising one or more one or more mutated ATG codons; an HIV-1 strain NL4-3 central polypurine tract (cPPT)/FLAP element of about 381 nucleotides in length and comprising a cPPT element and a CTS sequence; an HIV-1 strain HXB3 RRE RNA export element, an HIV-1 strain NL4-3 env splice acceptor sequence; an HS3 DNAseI hypersensitive site from the human β-globin LCR of about 847 nucleotides in length, an HS2 DNAseI hypersensitive site from the human β-globin LCR of about 638 nucleotides in length and human β-globin promotor operably linked to a shmiR expression cassette comprising a sequence set forth in SEQ ID NO: 1, and a synthetic poly(A) signal; and an HIV-1 strain NL4-3 3' SIN LTR.

In particular embodiments, a lentiviral vector contemplated herein comprises an HIV-1 strain NL4-3 5' LTR, wherein the U3 region has been replaced with a CMV promoter; a Psi (Ψ) packaging signal; a polynucleotide of about 459 nucleotides in length encoding a truncated gag protein and comprising one or more one or more mutated ATG codons; an HIV-1 strain NL4-3 central polypurine tract (cPPT)/FLAP element of about 381 nucleotides in length and comprising a cPPT element and a CTS sequence; an HIV-1 strain HXB3 RRE RNA export element, an HIV-1 strain NL4-3 env splice acceptor sequence; an HS3 DNAseI hypersensitive site from the human β-globin LCR of about 847 nucleotides in length, an HS2 DNAseI hypersensitive site from the human β-globin LCR of about 638 nucleotides in length and human β-globin promotor operably linked to a shmiR expression cassette comprising a sequence set forth in SEQ ID NO: 1, and a synthetic poly(A) signal; and an HIV-1 strain NL4-3 3' SIN LTR.

In particular embodiments, a lentiviral vector contemplated herein comprises an HIV-1 strain NL4-3 5' LTR, wherein the U3 region has been replaced with a CMV promoter; a Psi (Ψ) packaging signal; a polynucleotide of about 459 nucleotides in length encoding a truncated gag protein and comprising one or more one or more mutated ATG codons; an HIV-1 strain NL4-3 central polypurine tract (cPPT)/FLAP element of about 381 nucleotides in length and comprising a cPPT element and a CTS sequence; an HIV-1 strain HXB3 RRE RNA export element, an HIV-1 strain NL4-3 env splice acceptor sequence; an HS3 DNAseI hypersensitive site from the human β-globin LCR of about 847 nucleotides in length, an HS2 DNAseI hypersensitive site from the human β-globin LCR of about 638 nucleotides in length and human β-globin promotor operably linked to a shmiR expression cassette that comprises a guide strand that hybridizes to the sequence set forth in SEQ ID NO: 3, and a synthetic poly(A) signal; and an HIV-1 strain NL4-3 3' SIN LTR.

In preferred embodiments, the orientation of the shmiR expression cassette (one or more expression control sequences operably linked to a shmiR and a poly(A) signal) is opposite to the orientation of the genomic lentiviral RNA mediated by the 5' LTR.

Large scale viral particle production is often necessary to achieve a reasonable viral titer. Viral particles are produced by transfecting a transfer vector into a packaging cell line that comprises viral structural and/or accessory genes, e.g., gag, pol, env, tat, rev, vif, vpr, vpu, vpx, or nef genes or other viral genes.

As used herein, the term "packaging vector" refers to an expression vector or viral vector that lacks a packaging signal and comprises a polynucleotide encoding one, two, three, four or more viral structural and/or accessory genes. Typically, the packaging vectors are included in a packaging cell, and are introduced into the cell via transfection, transduction or infection. Methods for transfection, transduction or infection are well known by those of skill in the art. A lentiviral transfer vector contemplated in particular embodiments can be introduced into a packaging cell line, via transfection, transduction or infection, to generate a producer cell or cell line Viral envelope proteins (env) determine the range of host cells which can ultimately be infected and transformed by recombinant retroviruses generated from the cell lines. In one preferred embodiment, the lentivirus contemplated herein is pseudotyped with the VSV-G glycoprotein. The terms "pseudotype" or "pseudotyping" as used herein, refer to a virus whose viral envelope proteins have been substituted with those of another virus possessing preferable characteristics.

As used herein, the term "packaging cell lines" is used in reference to cell lines that do not contain a packaging signal, but do stably or transiently express viral structural proteins and replication enzymes (e.g., gag, pol and env) which are necessary for the correct packaging of viral particles. In particular embodiments, suitable cell line can be employed to prepare packaging cells of the invention. Generally, the cells are mammalian cells. In a particular embodiment, the cells used to produce the packaging cell line are human cells. Suitable cell lines which can be used include, for example, CHO cells, BHK cells, MDCK cells, C3H 10T1/2 cells, FLY cells, Psi-2 cells, BOSC 23 cells, PA317 cells, WEHI cells, COS cells, BSC 1 cells, BSC 40 cells, BMT 10 cells, VERO cells, W138 cells, MRCS cells, A549 cells, HT1080 cells, 293 cells, 293T cells, B-50 cells, 3T3 cells, NIH3T3 cells, HepG2 cells, Saos-2 cells, Huh7 cells, HeLa cells, W163 cells, 211 cells, and 211A cells. In preferred embodiments, the packaging cells are 293 cells, 293T cells, 293F cells, or A549 cells.

As used herein, the term "producer cell line" refers to a cell line which is capable of producing recombinant retroviral particles, comprising a packaging cell line and a transfer vector construct comprising a packaging signal. The production of infectious viral particles and viral stock solutions may be carried out using conventional techniques. Methods of preparing viral stock solutions are known in the art and are illustrated by, e.g., Y. Soneoka et al. (1995) *Nucl. Acids Res.* 23:628-633, and N. R. Landau et al. (1992) *J. Virol.* 66:5110-5113. Infectious virus particles may be collected from the packaging cells using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art, e.g., Kutner et al., *BMC Biotechnol.* 2009; 9:10. doi: 10.1186/1472-6750-9-10; Kutner et al. *Nat. Protoc.* 2009; 4(4):495-505. doi: 10.1038/nprot.2009.22.

D. Compositions and Formulations

The formulations and compositions contemplated herein may comprise a combination of any number of transduced or non-transduced cells or a combination thereof, viral vectors, polypeptides, polynucleotides, and one or more agents that increase transduction efficiency and/or VCN, e.g., poloxamers, and agents that increase prostaglandin signaling, as described herein, formulated in pharmaceutically-acceptable or physiologically-acceptable solutions (e.g., culture medium) for administration to a cell, tissue, organ, or an animal, either alone, or in combination with one or more other modalities of therapy.

Particular ex vivo and in vitro formulations and compositions contemplated herein may comprise a population of human CD34$^+$ cells, transduced with a lentiviral vector comprising one or more erythroid cell expression control sequences operably linked to a polynucleotide encoding a BCL11A shmiR, formulated in pharmaceutically-acceptable or physiologically-acceptable solutions (e.g., culture medium) for administration to a cell, tissue, organ, or an animal, either alone, or in combination with one or more other modalities of therapy.

Particular in vivo formulations and compositions contemplated herein may comprise a combination of viral vectors, and one or more agents that increase transduction efficiency and/or VCN, e.g., poloxamers and agents that increase prostaglandin signaling, as described herein, formulated in pharmaceutically-acceptable or physiologically-acceptable solutions (e.g., culture medium) for administration to a cell, tissue, organ, or an animal, either alone, or in combination with one or more other modalities of therapy.

In certain embodiments, compositions contemplated herein comprise a population of cells comprising a therapeutically-effective amount of hematopoietic stem or progenitor cells, e.g., CD34$^+$ cells, transduced with a lentiviral vector comprising one or more erythroid cell expression control sequences operably linked to a polynucleotide encoding a BCL11A shmiR, formulated together with one or more pharmaceutically acceptable carriers (additives) and/or diluents (e.g., pharmaceutically acceptable cell culture medium).

In particular embodiments, compositions comprise a population of cells comprising stem or progenitor cells, a lentiviral vector comprising one or more erythroid cell expression control sequences operably linked to a polynucleotide encoding a BCL11A shmir, and one or more agents that increase transduction efficiency and/or VCN, e.g., poloxamers and agents that increase prostaglandin signaling, as described herein, formulated together with one or more pharmaceutically acceptable carriers (additives) and/or diluents (e.g., pharmaceutically acceptable cell culture medium). In a related embodiment, the population of cells comprises hematopoietic stem and progenitor cells. In one embodiment, the population of cells comprises CD34$^+$ cells. In one embodiment, the population of cells comprises CD133$^+$ cells. In one embodiment, the population of cells are CD34$^+$ selected cells.

In preferred embodiments, the population of cells comprises CD34$^+$ cells that have one of the following β-globin alleles: $β^E/β^0$, $β^C/β^0$, $β^0/β^0$, $β^E/β^E$, $β^C/β^+$, $β^E/β^+$, $β^0/β^+$, $β^+/β^+$, $β^C/β^C$, $β^E/β^S$, $β^0/β^S$, $β^C/β^S$, $β^+/β^S$ or $β^S/β^S$.

In preferred embodiments, the population of cells comprises CD34$^+$ cells that have one of the following β-globin alleles: $β^E/β^0$, $β^C/β^0$, $β^0/β^0$, $β^C/β^C$, $β^E/β^E$, $β^E/β^+$, $β^C/β^E$, $β^C/β^+$, $β^0/β^+$, or $β^+/β^+$.

In preferred embodiments, the population of cells comprises CD34$^+$ cells that have one of the following β-globin alleles: $β^E/β^S$, $β^0/β^S$, $β^C/β^S$, $β^+/β^S$ or $β^S/β^S$.

Pharmaceutical compositions contemplated in particular embodiments herein comprise transduced cells produced according to methods described herein and a pharmaceutically acceptable carrier.

In other embodiments, pharmaceutical compositions comprise a lentiviral vector comprising one or more erythroid cell expression control sequences operably linked to a polynucleotide encoding a BCL11A shmiR and one or more agents that increase transduction efficiency and/or VCN, including but not limited to poloxamers and agents that increase prostaglandin signaling.

The phrase "pharmaceutically acceptable" refers to molecular entities and compositions that do not produce an allergic or similar untoward reaction when administered to a human. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the therapeutic cells are administered. Illustrative examples of pharmaceutical carriers can be sterile liquids, such as cell culture media, water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients in particular embodiments, include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Except insofar as any conventional media or agent is incompatible with the active ingredient, its use in the therapeutic compositions is contemplated. Supplementary active ingredients can also be incorporated into the compositions.

In one embodiment, a composition comprising a carrier is suitable for parenteral administration, e.g., intravascular (intravenous or intraarterial), intraperitoneal or intramuscular administration. Pharmaceutically acceptable carriers include sterile aqueous solutions, cell culture media, or dispersions. The use of such media and agents for pharmaceutically active substances is well known in the art. Except insofar as any conventional media or agent is incompatible with the transduced cells, use thereof in the pharmaceutical compositions is contemplated.

In particular embodiments, compositions contemplated herein comprise genetically modified hematopoietic stem and/or progenitor cells and a pharmaceutically acceptable carrier, e.g., pharmaceutically acceptable cell culture medium. A composition comprising a cell-based composition contemplated herein can be administered separately by enteral or parenteral administration methods or in combination with other suitable compounds to effect the desired treatment goals The pharmaceutically acceptable carrier must be of sufficiently high purity and of sufficiently low toxicity to render it suitable for administration to the human subject being treated. It further should maintain or increase the stability of the composition. The pharmaceutically acceptable carrier can be liquid or solid and is selected, with the planned manner of administration in mind, to provide for the desired bulk, consistency, etc., when combined with other components of the composition. For example, the pharmaceutically acceptable carrier can be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions contemplated herein include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like.

Such carrier solutions also can contain buffers, diluents and other suitable additives. The term "buffer" as used herein refers to a solution or liquid whose chemical makeup neutralizes acids or bases without a significant change in pH. Examples of buffers contemplated herein include, but are not limited to, Dulbecco's phosphate buffered saline (PB S), Ringer's solution, 5% dextrose in water (D5W), normal/physiologic saline (0.9% NaCl).

The pharmaceutically acceptable carriers and/or diluents may be present in amounts sufficient to maintain a pH of the therapeutic composition of about 7. Alternatively, the therapeutic composition has a pH in a range from about 6.8 to about 7.4, e.g., 6.8, 6.9, 7.0, 7.1, 7.2, 7.3, and 7.4. In still another embodiment, the therapeutic composition has a pH of about 7.4.

Compositions contemplated herein may comprise a non-toxic pharmaceutically acceptable medium. The compositions may be a suspension. The term "suspension" as used herein refers to non-adherent conditions in which cells are not attached to a solid support. For example, cells maintained as a suspension may be stirred or agitated and are not adhered to a support, such as a culture dish.

In particular embodiments, compositions contemplated herein are formulated in a suspension, where the hematopoietic stem and/or progenitor cells are dispersed within an acceptable liquid medium or solution, e.g., saline or serum-free medium, in an intravenous (IV) bag or the like. Acceptable diluents include, but are not limited to water, PlasmaLyte, Ringer's solution, isotonic sodium chloride (saline) solution, serum-free cell culture medium, and medium suitable for cryogenic storage, e.g., Cryostor® medium.

In certain embodiments, a pharmaceutically acceptable carrier is substantially free of natural proteins of human or animal origin, and suitable for storing a composition comprising a population of cells, e.g., hematopoietic stem and progenitor cells. The therapeutic composition is intended to be administered into a human patient, and thus is substantially free of cell culture components such as bovine serum albumin, horse serum, and fetal bovine serum.

In some embodiments, compositions are formulated in a pharmaceutically acceptable cell culture medium. Such compositions are suitable for administration to human subjects. In particular embodiments, the pharmaceutically acceptable cell culture medium is a serum free medium.

Serum-free medium has several advantages over serum containing medium, including a simplified and better defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

Illustrative examples of serum-free media used in particular compositions includes, but is not limited to QB SF-60 (Quality Biological, Inc.), StemPro-34 (Life Technologies), and X-VIVO 10.

In a preferred embodiment, the compositions comprising hematopoietic stem and/or progenitor cells are formulated in PlasmaLyte.

In various embodiments, compositions comprising hematopoietic stem and/or progenitor cells are formulated in a cryopreservation medium. For example, cryopreservation media with cryopreservation agents may be used to maintain a high cell viability outcome post-thaw. Illustrative examples of cryopreservation media used in particular compositions includes, but is not limited to, CryoStor CS10, CryoStor CS5, and CryoStor CS2.

In particular embodiments, the composition is substantially free of *mycoplasma*, endotoxin, and microbial contamination. By "substantially free" with respect to endotoxin is meant that there is less endotoxin per dose of cells than is allowed by the FDA for a biologic, which is a total endotoxin of 5 EU/kg body weight per day, which for an average 70 kg person is 350 EU per total dose of cells. In particular embodiments, compositions comprising hematopoietic stem or progenitor cells transduced with a retroviral vector contemplated herein contains about 0.5 EU/mL to about 5.0 EU/mL, or about 0.5 EU/mL, 1.0 EU/mL, 1.5 EU/mL, 2.0 EU/mL, 2.5 EU/mL, 3.0 EU/mL, 3.5 EU/mL, 4.0 EU/mL, 4.5 EU/mL, or 5.0 EU/mL.

In certain embodiments, compositions and formulations suitable for the delivery of viral vector systems (i.e., viral-mediated transduction) are contemplated including, but not limited to, retroviral (e.g., lentiviral) vectors.

Exemplary formulations for ex vivo delivery may also include the use of various transfection agents known in the art, such as calcium phosphate, electroporation, heat shock and various liposome formulations (i.e., lipid-mediated transfection). Liposomes, as described in greater detail below, are lipid bilayers entrapping a fraction of aqueous fluid. DNA spontaneously associates to the external surface of cationic liposomes (by virtue of its charge) and these liposomes will interact with the cell membrane.

In particular embodiments, formulation of pharmaceutically-acceptable excipients and carrier solutions is well-known to those of skill in the art, as is the development of suitable dosing and treatment regimens for using the particular compositions described herein in a variety of treatment regimens, including e.g., enteral and parenteral, e.g., intravascular, intravenous, intrarterial, intraosseously, and intramedullary administration and formulation. It would be understood by the skilled artisan that particular embodiments contemplated herein may comprise other formulations, such as those that are well known in the pharmaceutical art, and are described, for example, in Remington: The Science and Practice of Pharmacy, 20th Edition. Baltimore, Md.: Lippincott Williams & Wilkins, 2005, which is incorporated by reference herein, in its entirety.

E. Cell Culture Compositions

As discussed herein throughout, in particular embodiments, compositions and methods contemplated herein are useful for ex vivo and in vivo cell-based gene therapies. In particular embodiments, compositions may comprise cells in culture, i.e., a cell culture composition. A cell culture composition may comprise a population of cells comprising hematopoietic stem or progenitor cells, a suitable cell culture medium, one or more poloxamers, one or more agents that increase prostaglandin signaling.

In particular embodiments, cultured cells are hematopoietic stem or progenitor cells or CD34+ cells transduced with a lentiviral vector comprising one or more erythroid cell expression control sequences operably linked to a polynucleotide encoding a BCL11A shmiR, wherein the cells have the following β-globin alleles: $\beta^E/\beta^0$, $\beta^C/\beta^0$, $\beta^0/\beta^0$, $\beta^E/\beta^E$, $\beta^C/\beta^+$, $\beta^E/\beta^+$, $\beta^0/\beta^+$, $\beta^+/\beta^+$, $\beta^C/\beta^C$, $\beta^E/\beta^S$, $\beta^0/\beta^S$, $\beta^C/\beta^S$, $\beta^+/\beta^S$ or $\beta^S/\beta^S$.

In particular embodiments, cultured cells are hematopoietic stem or progenitor cells or CD34+ cells transduced with a lentiviral vector comprising one or more erythroid cell expression control sequences operably linked to a polynucleotide encoding a BCL11A shmiR, wherein the cells have the following β-globin alleles: $\beta^E/\beta^S$, $\beta^0/\beta^S$, $\beta^C/\beta^S$, $\beta^+/\beta^S$ or $\beta^S/\beta^S$.

In particular embodiments, cultured cells are hematopoietic stem or progenitor cells or CD34+ cells transduced with a lentiviral vector comprising one or more erythroid cell expression control sequences operably linked to a polynucleotide encoding a BCL11A shmiR, wherein the cells have the following β-globin alleles: $\beta^E/\beta^S$, $\beta^0/\beta^S$, $\beta^C/\beta^S$, $\beta^+/\beta^S$ or $\beta^S/\beta^S$.

In one embodiment, a cell culture composition comprises a population of cells comprising hematopoietic stem or progenitor cells, a cell culture medium suitable for human administration, cells transduced with a lentiviral vector comprising one or more erythroid cell expression control sequences operably linked to a polynucleotide encoding a BCL11A shmiR, a poloxamer and an agent that increases prostaglandin signaling.

In some embodiments, the cell culture medium is a pharmaceutically acceptable cell culture medium.

Cell culture compositions contemplated herein, that comprise transduced hematopoietic stem or progenitor cells, can be administered systemically or by directed injection to a subject in need thereof in order to effect the desired gene therapy.

F. Transduction Methods

The compositions and methods contemplated herein in particular embodiments increase the VCN and transduce significantly more cells with significantly less virus, thereby minimizing the risk of genomic alteration and/or insertional activation of proto-oncogenes in the genome of the therapeutic cell, while simultaneously increasing the therapeutic efficacy of the drug product produced. Thus, the compositions and methods contemplated herein not only lead to production of a safer gene therapy, but to a more robust and therapeutically efficacious drug product.

The delivery of a gene(s) or other polynucleotide sequences using a lentiviral vector by means of viral infection rather than by transfection is referred to as transduction. In one embodiment, lentiviral vectors are transduced into a cell through infection and provirus integration. In certain embodiments, a cell, e.g., a target cell, is transduced if it comprises a gene or other polynucleotide sequence delivered to the cell by infection using a lentiviral vector. In particular embodiments, a transduced cell comprises one or more genes or other polynucleotide sequences delivered by a lentiviral vector in its cellular genome.

In particular embodiments, host cells or target cells transduced with a viral vector \ and are administered to a subject to treat and/or prevent a hemoglobinopathy or at least one symptom of a hemoglobinopathy.

The production of infectious viral particles and viral stock solutions may be carried out using conventional techniques. Methods of preparing viral stock solutions are known in the art and are illustrated by, e.g., Y. Soneoka et al. (1995) *Nucl. Acids Res.* 23:628-633, and N. R. Landau et al. (1992) *J. Virol.* 66:5110-5113.

In particular embodiments, HIV type 1 (HIV-1) based viral particles may be generated by co-expressing the virion packaging elements and the transfer vector in a producer cell. These cells may be transiently transfected with a number of plasmids. Typically, from three to five plasmids are employed, but the number may be greater depending upon the degree to which the lentiviral components are broken up into separate units. For example, one plasmid may encode the core and enzymatic components of the virion, derived from HIV-1. This plasmid is termed the packaging plasmid. Another plasmid typically encodes the envelope protein(s), most commonly the G protein of vesicular stomatitis virus (VSV G) because of its high stability and broad tropism. This plasmid may be termed the envelope expression plasmid. Yet another plasmid encodes the genome to be transferred to the target cell, that is, the vector itself, and is called the transfer vector. The packaging plasmids can be introduced into human cell lines by known techniques, including calcium phosphate transfection, lipofection or electroporation. Recombinant viruses with titers of several millions of transducing units per milliliter (TU/mL) can be generated by this technique and variants thereof. After ultracentrifugation concentrated stocks of about $10^8$ TU/mL, $10^9$ TU/mL, $10^{10}$ TU/mL, $10^{11}$ TU/mL, $10^{12}$ TU/mL, or about $10^{13}$ TU/mL can be obtained.

Infectious virus particles may be collected from the packaging cells using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art, e.g., Kutner et al., *BMC Biotechnol.* 2009; 9:10. doi: 10.1186/1472-6750-9-10; Kutner et al. *Nat. Protoc.* 2009; 4(4):495-505. doi: 10.1038/nprot.2009.22.

Viruses may be used to infect cells in vivo, ex vivo, or in vitro using techniques well known in the art. For example, when cells, for instance mobilized peripheral blood cells, bone marrow cells, CD34+ cells, or hematopoietic stem or progenitor cells are transduced ex vivo, the vector particles may be incubated with the cells using a dose generally in the order of between 1 to 50 multiplicities of infection (MOI) which also corresponds to $1 \times 10^5$ to $50 \times 10^5$ transducing units of the viral vector per $10^5$ cells. This, of course, includes amount of vector corresponding to 1, 2, 3, 4, 5, 6, 7, 8, 9, 10, 15, 20, 25, 30, 35, 40, 45, and 50 MOI and all integer values in between.

Viruses may also be delivered to a subject in vivo, by direct injection to the cell, tissue, or organ in need of therapy. Direct injection requires on the order of between 1 to 100 multiplicities of infection (MOI) which also corresponds to $1 \times 10^5$ to $100 \times 10^5$ transducing units of the viral vector per $10^5$ cells. This, of course, includes amount of vector corresponding to 1, 2, 3, 4, 5, 6, 7, 8, 9, 10, 15, 20, 25, 30, 35, 40, 45, 50, 55, 50, 65, 70, 75, 80, 85, 90, 95, and 100 MOI and all integer values in between.

Viruses may also be delivered according to viral titer (TU/mL), which can be measured, for example, by using a commercially available p24 titer assay, which is an ELISA against the p24 viral coat protein. The following formula can be used to calculate the pg/mL of p24: there are approximately 2000 molecules of p24 per physical particle (PP) of lentivirus: $(2 \times 10^3) \times (24 \times 10^3$ Da of p24 per PP), $48 \times 10^6$/Avogadro=$(48 \times 10^6)/(6 \times 10^{23})$=$8 \times 10^{-17}$ g of p24 per PP, approximately 1 PP per $1 \times 10^{-16}$ g of p24, $1 \times 10^4$ PP per pg of p24. A reasonably well packaged, VSV-G pseudotyped lentiviral vector will have an infectivity index in the range of 1 TU per 1000 physical particles (PP) to 1 TU per 100 PP (or less). Thus, the range is approximately 10 to 100 TU/pg of p24. It is through this conversion that TU/mL is obtained.

Based on previous experience, the amount of lentivirus directly injected is determined by total TU and can vary based on both the volume that could be feasibly injected to the site and the type of tissue to be injected. For example, a bone marrow injection site may only allow for a very small volume of virus to be injected, so a high titer prep would be preferred, a TU of about $1 \times 10^6$ to $1 \times 10^7$, about $1 \times 10^6$ to $1 \times 10^8$, $1 \times 10^6$ to $1 \times 10^9$, about $1 \times 10^7$ to $1 \times 10^{10}$, $1 \times 10^8$ to $1 \times 10^{11}$, about $1 \times 10^8$ to $1 \times 10^{12}$, or about $1 \times 10^{10}$ to $1 \times 10^{12}$ or more per injection could be used. However, a systemic delivery could accommodate a much larger TU, a load of $1 \times 10^8$, $1 \times 10^9$, $1 \times 10^{10}$, $1 \times 10^{11}$, $1 \times 10^{12}$, $1 \times 10^{13}$, $1 \times 10^{14}$, or $1 \times 10^{15}$, could be delivered.

Compositions and methods contemplated herein provide high transduction efficiency and VCN of hematopoietic cells in vitro, ex vivo, and in vivo, using lower viral titers than those disclosed above to achieve comparable transduction efficiencies in the absence of the compositions and methods provided herein.

Certain embodiments contemplated herein arise from the unexpected finding that particular lentiviral vector architectures compared to lentiviral architectures that exist in the art result in higher transduction efficiencies and/or VCNs in hematopoietic cells, in vitro, ex vivo, or in vivo, when the cells are transduced in the presence of the lentiviral vectors contemplated in particular embodiments herein and a poloxamer and one or more agents that stimulate the prostaglandin EP receptor signaling pathway (see e.g., WO 2007/112084 and WO2010/108028).

In particular embodiments, transduction efficiency is increased in a population of cells comprising hematopoietic stem or progenitor cells by culturing the cells in the presence of a lentiviral vector contemplated herein comprising one or more erythroid cell expression control sequences operably linked to a polynucleotide encoding a BCL11A shmiR in the presence of a poloxamer and one or more agents that stimulate the prostaglandin EP receptor signaling pathway. As used herein, the term "poloxamer" refers to a non-ionic triblock copolymer composed of a central hydrophobic chain of polyoxypropylene flanked by two hydrophilic chains of polyoxyethylene. Poloxamers are also known by the trade name of "Pluronics" or "Synperonics" (BASF). The block copolymer can be represented by the following formula: $HO(C_2H_4O)_x(C_3H_6O)_y(C_2H_4O)_zH$.

The lengths of the polymer blocks can be customized; as a result many different poloxamers exist. Poloxamers suitable for use in particular embodiments have an average molecular weight of at least about 10 kDa, at least about 11.4 kDa, at least about 12.6 kDa, at least about 13 kDa, at least about 14.6 kDa, or at least about 15 kDa. In particular embodiments, y can be in the range of about 39 to about 70.

As synthesis of block copolymers cannot be accurate, the above given values may not exactly be achievable upon synthesis and the average value will differ to a certain extent. Thus, the term "poloxamer" as used herein can be used interchangeably with the term "poloxamers" (representing an entity of several poloxamers, also referred to as mixture of poloxamers) if not explicitly stated otherwise. The term "average" in relation to the number of monomer units or molecular weight of (a) poloxamer(s) as used herein is a consequence of the technical inability to produce poloxamers all having the identical composition and thus the identical molecular weight. Poloxamers produced according to state of the art methods will be present as a mixture of poloxamers each showing a variability as regards their molecular weight, but the mixture as a whole averaging the molecular weight specified herein. BASF and Sigma Aldrich are suitable sources of poloxamers for use in particular embodiments contemplated herein.

In one embodiment, a poloxamer suitable for use in particular embodiments contemplated herein is selected from the group consisting of: poloxamer 288, poloxamer 335, poloxamer 338, and poloxamer 407.

In one embodiment, the poloxamer is poloxamer 288.
In one embodiment, the poloxamer is poloxamer 335.
In one embodiment, the poloxamer is poloxamer 338.
In one embodiment, the poloxamer is poloxamer 407.

In one embodiment, poloxamer 288 (F98; $HO(C_2H_4O)_x(C_3H_6O)_y(C_2H_4O)_zH$; x+y=236.36, z=44.83; average molecular weight of 13 kDa) is used to increase transduction efficiency and/or VCN in a population of hematopoietic cells comprising hematopoietic stem or progenitor cells. F98 can be used alone, or in combination with an agent that stimulates the prostaglandin EP receptor signaling pathway or staurosporine to increase transduction efficiency and/or VCN.

In one embodiment, poloxamer 335 (P105; $HO(C_2H_4O)_x(C_3H_6O)_y(C_2H_4O)_zH$; x+y=73.86, z=56.03; average molecular weight of 6.5 kDa) is used to increase transduction efficiency and/or VCN in a population of hematopoietic cells comprising hematopoietic stem or progenitor cells. P105 can be used alone, or in combination with an agent that stimulates the prostaglandin EP receptor signaling pathway or staurosporine to increase transduction efficiency and/or VCN.

In one embodiment, poloxamer 338 (F108; $HO(C_2H_4O)_x(C_3H_6O)_y(C_2H_4O)_zH$; x+y=265.45, z=50.34; average molecular weight of 14.6 kDa) is used to increase transduction efficiency and/or VCN in a population of hematopoietic cells comprising hematopoietic stem or progenitor cells. F108 can be used alone, or in combination with an agent that stimulates the prostaglandin EP receptor signaling pathway or staurosporine to increase transduction efficiency and/or VCN.

In one embodiment, poloxamer 407 (F127; $HO(C_2H_4O)_x(C_3H_6O)_y(C_2H_4O)_zH$; x+y=200.45, z=65.17; average molecular weight of 12.6 kDa) is used to increase transduction efficiency and/or VCN in a population of hematopoietic cells comprising hematopoietic stem or progenitor cells. F127 can be used alone, or in combination with an agent that stimulates the prostaglandin EP receptor signaling pathway or staurosporine to increase transduction efficiency and/or VCN.

Illustrative final poloxamer concentrations used to transduced hematopoietic cells include, but are not limited to about 10 μg/mL to about 5000 μg/mL, about 10 μg/mL to about 2500 μg/mL, about 10 μg/mL to about 1000 μg/mL, about 50 μg/mL to about 1000 μg/mL, about 100 μg/mL to about 1000 µg/mL, about 200 µg/mL to about 1000 µg/mL, about 200 µg/mL to about 500 µg/mL, or about 10 µg/mL, about 20 µg/mL, about 30 µg/mL, about 40 µg/mL, about 50 µg/mL, about 60 µg/mL, about 70 µg/mL, about 80 µg/mL, about 90 µg/mL, about 100 µg/mL, about 200 µg/mL, about 300 µg/mL, about 400 µg/mL, about 500 µg/mL, about 600 µg/mL, about 700 µg/mL, about 800 µg/mL, about 900 µg/mL, about 1000 µg/mL, about 1250 µg/mL, about 1500 µg/mL, about 1750 µg/mL, about 2000 µg/mL, about 2500 µg/mL, or about 5000 µg/mL or more, and any intervening concentration thereof.

Surprisingly, the present inventors have discovered that transduction efficiency and/or VCN of populations of cells comprising hematopoietic stem and progenitor cells with a lentiviral vector contemplated herein comprising one or more erythroid cell expression control sequences operably linked to a polynucleotide encoding a BCL11A shmiR can be increased by transducing the cells in the presence of a poloxamer and one or more agents that stimulate the prostaglandin EP receptor signaling pathway.

As used herein, the terms "stimulate the prostaglandin EP receptor signaling," "activate the prostaglandin EP receptor signaling," or "increase the prostaglandin EP receptor signaling" generally refers to the ability of an agent to increase the cell signaling activity downstream of a prostaglandin EP receptor in the cell contacted with the one or more agents compared to the cell signaling activity downstream of the prostaglandin EP receptor in the absence of the one or more agents. Agents that stimulate the prostaglandin EP receptor signaling include, but are not limited to small molecules, or those compounds disclosed in WO 2007/112084 and WO2010/108028, each of which is herein incorporated by reference in its entirety. Assays that can be used to measure activation or stimulation of the prostaglandin EP receptor signaling pathway are known in the art, and are described in, for example, WO2010/108028, which is herein incorporated by reference in its entirety.

Illustrative examples of agents that stimulate the prostaglandin EP receptor signaling pathway include, but are not limited to, small molecules, e.g., small organic molecules, prostaglandins, Wnt pathway agonists, cAMP/PI3K/AKT pathway agonists, $Ca^{2+}$ second messenger pathway agonists, nitric oxide (NO)/angiotensin signaling agonists, and other compounds known to stimulate the prostaglandin signaling pathway selected from the group consisting of: Mebeverine, Flurandrenolide, Atenolol, Pindolol, Gaboxadol, Kynurenic Acid, Hydralazine, Thiabendazole, Bicuclline, Vesamicol, Peruvoside, Imipramine, Chlorpropamide, 1,5-Pentamethylenetetrazole, 4-Aminopyridine, Diazoxide, Benfotiamine, 12-Methoxydodecenoic acid, N-Formyl-Met-Leu-Phe, Gallamine, IAA 94, Chlorotrianisene, and derivatives of these compounds.

In particular embodiments, the agent that stimulates the prostaglandin pathway is a naturally-occurring or synthetic chemical molecule or polypeptide that binds to and/or interacts with an EP receptor, typically to activate or increase one or more of the downstream signaling pathways associated with a prostaglandin EP receptor.

In one embodiment, the agent that stimulates the prostaglandin pathway is selected from the group consisting of: $PGA_2$; $PGB_2$; $PGD_2$; $PGE_1$ (Alprostadil); $PGE_2$; $PGF_2$; $PGI_2$ (Epoprostenol); $PGH_2$; $PGJ_2$; and derivatives and analogues thereof.

Additional illustrative agents that stimulate the prostaglandin pathway include, but are not limited to 15d-$PGJ_2$; delta12-$PGJ_2$; 2-hydroxyheptadecatrienoic acid (HET); Thromboxane ($TXA_2$ and $TXB_2$); $PGI_2$ analogs, e.g., Iloprost and Treprostinil; $PGF_2$ analogs, e.g., Travoprost, Carboprost tromethamine, Tafluprost, Latanoprost, Bimatoprost, Unoprostone isopropyl, Cloprostenol, Oestrophan, and Superphan; $PGE_1$ analogs, e.g., 11-deoxy $PGE_1$, Misoprostol and Butaprost; and Corey alcohol-A [[3aα,4α,5β,6aα]-(–)-[Hexahydro-4-(hydroxymetyl)-2-oxo-2H-cyclopenta/b/furan-5-yl][1,1'-bifenyl]-4-carboxylate]; Corey alcohol-B [2H-Cyclopenta[b]furan-2-on,5-(benzoyloxy) hexahydro-4-(hydroxymethyl)[3aR-(3aα,4α,5β,6aα)]]; and Corey diol ((3aR,4S,5R,6aS)-hexahydro-5-hydroxy-4-(hydroxymethyl)-2H-cyclopenta[b]furan-2-one).

In one embodiment, the agent is a prostaglandin EP receptor ligand including, but not limited to, prostaglandin $E_2$ ($PGE_2$), as well as "analogs" or "derivatives" thereof.

Illustrative examples of $PGE_2$ "analogs" or "derivatives" include, but are not limited to, 16,16-dimethyl $PGE_2$, 16-16 dimethyl $PGE_2$ p-(p-acetamidobenzamido) phenyl ester, 11-deoxy-16,16-dimethyl $PGE_2$, 9-deoxy-9-methylene-16,16-dimethyl $PGE_2$, 9-deoxy-9-methylene $PGE_2$, 9-keto Fluprostenol, 5-trans $PGE_2$, 17-phenyl-omega-trinor $PGE_2$, $PGE_2$ serinol amide, $PGE_2$ methyl ester, 16-phenyl tetranor $PGE_2$, 15(S)-15-methyl $PGE_2$, 15 (R)-15-methyl $PGE_2$, 8-iso-15-keto $PGE_2$, 8-iso $PGE_2$ isopropyl ester, 20-hydroxy $PGE_2$, nocloprost, sulprostone, butaprost, 15-keto $PGE_2$, and 19 (R) hydroxyy $PGE_2$.

In a particular embodiment, a method of improving transduction efficiency comprises culturing a population of cells with a lentiviral vector contemplated herein comprising one or more erythroid cell expression control sequences operably linked to a polynucleotide encoding a BCL11A shmiR and a poloxamer and one or more agents that are ligands of a prostaglandin EP receptor selected from the group consisting of: $PGE_2$, 16,16-dimethyl $PGE_2$, 16-16 dimethyl $PGE_2$ p-(p-acetamidobenzamido) phenyl ester, 11-deoxy-16,16-dimethyl $PGE_2$, 9-deoxy-9-methylene-16, 16-dimethyl $PGE_2$, 9-deoxy-9-methylene $PGE_2$, 9-keto Fluprostenol, 5-trans $PGE_2$, 17-phenyl-omega-trinor $PGE_2$, $PGE_2$ serinol amide, $PGE_2$ methyl ester, 16-phenyl tetranor $PGE_2$, 15(S)-15-methyl $PGE_2$, 15 (R)-15-methyl $PGE_2$, 8-iso-15-keto $PGE_2$, 8-iso $PGE_2$ isopropyl ester, 20-hydroxy $PGE_2$, nocloprost, sulprostone, butaprost, 15-keto $PGE_2$, and 19 (R) hydroxyy $PGE_2$.

In particular embodiments, the agent that stimulates a prostaglandin EP receptor pathway is $PGE_2$ or 16,16-dimethyl $PGE_2$.

In one embodiment, the agent that stimulates a prostaglandin EP receptor pathway is $PGE_2$.

In various embodiments, a population of cells is transduced in the presence of a lentiviral vector contemplated herein comprising one or more erythroid cell expression control sequences operably linked to a polynucleotide encoding a BCL11A shmiR, a poloxamer selected from the group consisting of: poloxamer 288, poloxamer 335, poloxamer 338, and poloxamer 407, and one or more agents that are ligands of a prostaglandin EP receptor selected from the group consisting of: $PGE_2$, 16,16-dimethyl $PGE_2$, 16-16 dimethyl $PGE_2$ p-(p-acetamidobenzamido) phenyl ester, 11-deoxy-16,16-dimethyl $PGE_2$, 9-deoxy-9-methylene-16,16-dimethyl $PGE_2$, 9-deoxy-9-methylene $PGE_2$, 9-keto Fluprostenol, 5-trans $PGE_2$, 17-phenyl-omega-trinor $PGE_2$, $PGE_2$ serinol amide, $PGE_2$ methyl ester, 16-phenyl tetranor $PGE_2$, 15(S)-15-methyl $PGE_2$, 15 (R)-15-methyl $PGE_2$, 8-iso-15-keto $PGE_2$, 8-iso $PGE_2$ isopropyl ester, 20-hydroxy $PGE_2$, nocloprost, sulprostone, butaprost, 15-keto $PGE_2$, and 19 (R) hydroxyy $PGE_2$.

Illustrative final prostaglandin EP receptor signaling pathway agonist concentrations used to transduced hematopoietic cells include, but are not limited to about 10 μM to about 200 μM, about 10 μM to about 100 μM, about 50 μM to about 100 μM, or about 10 μM, about 20 μM, about 30 μM, about 40 μM, about 50 μM, about 60 μM, about 70 μM, about 80 μM, about 90 μM, or about 100 μM or more, and any intervening concentration thereof.

In various embodiments, a population of cells is transduced in the presence of a lentiviral vector contemplated herein comprising one or more erythroid cell expression control sequences operably linked to a polynucleotide encoding a BCL11A shmiR, a poloxamer selected from the group consisting of: poloxamer 288, poloxamer 335, poloxamer 338, and poloxamer 407, and $PGE_2$.

In various embodiments, a population of cells is transduced in the presence of a lentiviral vector contemplated herein comprising one or more erythroid cell expression control sequences operably linked to a polynucleotide encoding a BCL11A shmiR, a poloxamer selected from the group consisting of: poloxamer 288, poloxamer 335, poloxamer 338, and poloxamer 407, and 16,16-dimethyl $PGE_2$ In particular embodiments, hematopoietic cells may be cultured in the presence of a lentivirus may be exposed to (contacted with) a poloxamer and one or more agents that stimulates the prostaglandin EP receptor signaling pathway, for a duration of about 10 minutes, about 30 minutes, about 1 hour, about 2 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 48 hours, or about 72 hours, or any intervening duration of time.

In various embodiments, the lentiviral vector architectures, compositions and methods contemplated herein increase transduction efficiency to at least about 30%, at least about 40%, at least about 50%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, including any intervening percentages.

In various embodiments, the lentiviral vector architectures, the compositions and methods contemplated herein increase average VCN to at least about 0.5 to at least about 5.0, at least about 0.5 to at least about 3, at least about 0.5 to at least about 1.0, at least about 1.0 to at least about 5.0, at least about 1.0 to at least about 3.0, or at least about 0.5, at least about 1.0, at least about 1.5, at least about 2.0, at least about 2.5, at least about 3.0, at least about 3.5, at least about 4.0, at least about 4.5, or at least about 5.0.

In various embodiments, hematopoietic cells transduced with the lentiviral vector architectures, the compositions and methods contemplated herein have a transduction efficiency of at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% and an average VCN of at least about 0.5, at least about 1.0, at least about 1.5, at least about 2.0, or at least about 2.5.

Certain embodiments contemplate isolation and transduction of a population of cells. As used herein, the term "population of cells" refers to a plurality of cells that may be made up of any number and/or combination of homogenous or heterogeneous cell types, as described elsewhere herein.

For example, for transduction of hematopoietic stem or progenitor cells, a population of cells may be isolated or obtained from umbilical cord blood, placental blood, bone marrow, or peripheral blood. A population of cells may comprise about 10%, about 20%, about 30%, about 40%, about 50%, about 60%, about 70%, about 80%, about 90%, or about 100% of the target cell type to be transduced. In certain embodiments, hematopoietic stem or progenitor cells may be isolated or purified from a population of heterogeneous cells using methods known in the art.

Preferred target cell types transduced with the compositions and methods contemplated herein include, hematopoietic cells, e.g., human hematopoietic cells.

Illustrative sources to obtain hematopoietic cells transduced with the methods and compositions contemplated herein include, but are not limited to: cord blood, bone marrow or mobilized peripheral blood.

Illustrative examples of hematopoietic cells include $CD34^+$ cells. The term "$CD34^+$ cell," as used herein refers to a cell expressing the CD34 protein on its cell surface. "CD34," as used herein refers to a cell surface glycoprotein (e.g., sialomucin protein) that often acts as a cell-cell adhesion factor. $CD34^+$ is a cell surface marker of both hematopoietic stem and progenitor cells.

Additional illustrative examples of hematopoietic stem or progenitor cells include hematopoietic cells that are $CD34^+$ $CD38^{Lo}CD90^+CD45^{RA-}$, hematopoietic cells that are $CD34^+$, $CD59^+$, $Thy1/CD90^+$, $CD38^{Lo/-}$, $C$-kit/$CD117^+$, and Lin-, and hematopoietic cells that are $CD133^+$.

In particular embodiments, $CD34^+$ cells that are transduced with a lentiviral vector comprising one or more erythroid cell expression control sequences operably linked to a polynucleotide encoding a BCL11A shmiR and compositions contemplated herein have the following β-globin alleles: $\beta^E/\beta^0$, $\beta^C/\beta^0$, $\beta^0/\beta^0$, $\beta^E/\beta^E$, $\beta^C/\beta^+$, $\beta^E/\beta^+$, $\beta^0/\beta^+$, $\beta^+/\beta^+$, $\beta^C/\beta^C$, $\beta^E/\beta^S$, $\beta^0/\beta^S$, $\beta^C/\beta^S$, $\beta^+/\beta^S$ or $\beta^S/\beta^S$.

In particular embodiments, $CD34^+$ cells that are transduced with a lentiviral vector comprising one or more erythroid cell expression control sequences operably linked to a polynucleotide encoding a BCL11A shmiR and compositions contemplated herein have the following β-globin alleles: $\beta^E/\beta^0$, $\beta^C/\beta^0$, $\beta^0/\beta^0$, $\beta^C/\beta^C$, $\beta^E/\beta^E$, $\beta^E/\beta^+$, $\beta^C/\beta^+$, $\beta^0/\beta^+$, or $\beta^+/\beta^+$.

In particular embodiments, $CD34^+$ cells that are transduced with a lentiviral vector comprising one or more erythroid cell expression control sequences operably linked to a polynucleotide encoding a BCL11A shmiR and compositions contemplated herein have the following β-globin alleles: $\beta^E/\beta^S$, $\beta^0/\beta^S$, $\beta^C/\beta^S$, $\beta^+/\beta^S$ or $\beta^S/\beta^S$.

G. Gene Therapy Methods

Drug products comprising a higher proportion of hematopoietic cells comprising a lentiviral vector comprising one or more erythroid cell expression control sequences operably linked to a polynucleotide encoding a BCL11A shmiR, wherein the vector copy number of in each cell is also higher provides for more therapeutically efficacious gene therapies. As used herein, the term "drug product" refers to genetically modified cells produced using the compositions and methods contemplated herein. In particular embodiments, the drug product comprises genetically modified hematopoietic stem or progenitor cells, e.g., $CD34^+$ cells. Without wishing to be bound to any particular theory, increasing the amount of a therapeutic in a drug product may allow treatment of subjects having no or minimal expression of the corresponding gene in vivo, thereby significantly expanding the opportunity to bring gene therapy to subjects for which gene therapy was not previously a viable treatment option.

The transduced cells and corresponding lentiviral vectors contemplated herein provide improved methods of gene therapy. As used herein, the term "gene therapy" refers to the introduction of a gene into a cell's genome. In various embodiments a lentiviral vector comprising one or more erythroid cell expression control sequences operably linked to a polynucleotide encoding a BCL11A shmiR that provides curative, preventative, or ameliorative benefits to a subject diagnosed with or that is suspected of having a hemoglobinopathy or hemoglobinopathic condition.

As used herein, the terms "hemoglobinopathy" or "hemoglobinopathic condition" refer to a diverse group of inherited blood disorders that involve the presence of abnormal hemoglobin molecules resulting from alterations in the structure and/or synthesis of hemoglobin. Normally, hemoglobin consists of four protein subunits: two subunits of β-globin and two subunits of α-globin. Each of these protein subunits is attached (bound) to an iron-containing molecule called heme; each heme contains an iron molecule in its center that can bind to one oxygen molecule. Hemoglobin within red blood cells binds to oxygen molecules in the lungs. These cells then travel through the bloodstream and deliver oxygen to tissues throughout the body.

Hemoglobin A (HbA) is the designation for the normal hemoglobin that exists after birth. Hemoglobin A is a tetramer with two alpha chains and two beta chains ($\alpha_2\beta_2$). Hemoglobin A2 is a minor component of the hemoglobin found in red cells after birth and consists of two alpha chains and two delta chains ($\alpha_2\delta_2$). Hemoglobin A2 generally comprises less than 3% of the total red cell hemoglobin. Hemoglobin F is the predominant hemoglobin during fetal development. The molecule is a tetramer of two alpha chains and two gamma chains ($\alpha_2\gamma_2$).

The most common hemoglobinopathies include sickle cell disease, β-thalassemia, and α-thalassemia.

In particular embodiments, the compositions and methods contemplated herein provide gene therapy for subjects having a sickle cell disease. The term "sickle cell anemia" or "sickle cell disease" is defined herein to include any symptomatic anemic condition which results from sickling of red blood cells. Sickle cell anemia $\beta^S/\beta^S$, a common form of sickle cell disease (SCD), is caused by Hemoglobin S (HbS). HbS is generated by replacement of glutamic acid (E) with valine (V) at position 6 in β-globin, noted as Glu6Val or E6V. Replacing glutamic acid with valine causes the abnormal HbS subunits to stick together and form long, rigid molecules that bend red blood cells into a sickle (crescent) shape. The sickle-shaped cells die prematurely, which can lead to a shortage of red blood cells (anemia). In addition, the sickle-shaped cells are rigid and can block small blood vessels, causing severe pain and organ damage. Without wishing to be bound by any particular theory, the lentiviral vectors contemplated herein reduce or eliminate BCL11A expression in erythroid cells and result in the reactivation or derepression of γ-globin gene expression and a decrease in $\beta^S$-globin gene expression, and thereby increase HbF expression to effectively treat and/or ameliorate one or more symptoms associated with subjects that have a hemoglobinopathy.

Additional mutations in the β-globin gene can also cause other abnormalities in β-globin, leading to other types of sickle cell disease. These abnormal forms of β-globin are often designated by letters of the alphabet or sometimes by a name. In these other types of sickle cell disease, one β-globin subunit is replaced with HbS and the other β-globin subunit is replaced with a different abnormal variant, such as hemoglobin C (HbC; β-globin allele noted as $\beta^C$) or hemoglobin E (HbE; β-globin allele noted as $\beta^E$).

In hemoglobin SC (HbSC) disease, the β-globin subunits are replaced by HbS and HbC. HbC results from a mutation in the β-globin gene and is the predominant hemoglobin found in people with HbC disease ($\alpha_2\beta^C_2$). HbC results when the amino acid lysine replaces the amino acid glutamic acid at position 6 in β-globin, noted as Glu6Lys or E6K. HbC disease is relatively benign, producing a mild hemolytic anemia and splenomegaly. The severity of HbSC disease is variable, but it can be as severe as sickle cell anemia.

HbE is caused when the amino acid glutamic acid is replaced with the amino acid lysine at position 26 in β-globin, noted as Glu26Lys or E26K. People with HbE disease have a mild hemolytic anemia and mild splenomegaly. HbE is extremely common in Southeast Asia and in some areas equals hemoglobin A in frequency. In some cases, the HbE mutation is present with HbS. In these cases, a person may have more severe signs and symptoms associated with sickle cell anemia, such as episodes of pain, anemia, and abnormal spleen function.

Other conditions, known as hemoglobin sickle-β-thalassemias (HbSBetaThal), are caused when mutations that produce hemoglobin S and β-thalassemia occur together. Mutations that combine sickle cell disease with beta-zero ($\beta^0$; gene mutations that prevent β-globin production) thalassemia lead to severe disease, while sickle cell disease combined with beta-plus ($\beta^+$; gene mutations that decrease β-globin production) thalassemia is milder.

As used herein, "thalassemia" refers to a hereditary disorder characterized by defective production of hemoglobin. Examples of thalassemias include α- and β-thalassemia.

In particular embodiments, the compositions and methods contemplated herein provide gene therapy for subjects having a β-thalassemia. β-thalassemias are caused by a mutation in the β-globin chain, and can occur in a major or minor form. Nearly 400 mutations in the β-globin gene have been found to cause β-thalassemia. Most of the mutations involve a change in a single DNA building block (nucleotide) within or near the β-globin gene. Other mutations insert or delete a small number of nucleotides in the β-globin gene. As noted above, β-globin gene mutations that decrease β-globin production result in a type of the condition called beta-plus ($\beta^+$) thalassemia. Mutations that prevent cells from producing any beta-globin result in beta-zero) ($\beta^0$) thalassemia. In the major form of β-thalassemia, children are normal at birth, but develop anemia during the first year of life. The minor form of β-thalassemia produces small red blood cells. Thalassemia minor occurs if you receive the defective gene from only one parent. Persons with this form of the disorder are carriers of the disease and usually do not have symptoms. Without wishing to be bound by any particular theory, the lentiviral vectors contemplated herein reduce or eliminate BCL11A expression in erythroid cells and result in the reactivation or derepression of γ-globin gene expression and a decrease in β-thalassemic globin gene expression, and thereby increase HbF expression to effectively treat and/or ameliorate one or more symptoms associated with subjects that have a β-thalassemia.

HbE/β-thalassemia results from combination of HbE and β-thalassemia ($\beta^E/\beta^0$, $\beta^E/\beta^+$) and produces a condition more severe than is seen with either HbE trait or β-thalassemia trait. The disorder manifests as a moderately severe thalassemia that falls into the category of thalassemia intermedia. HbE/β-thalassemia is most common in people of Southeast Asian background.

In particular embodiments, the compositions and methods contemplated herein provide gene therapy for subjects having an α-thalassemia. α-thalassemia is a fairly common blood disorder worldwide. Thousands of infants with Hb Bart syndrome and HbH disease are born each year, particularly in Southeast Asia. A-thalassemia also occurs frequently in people from Mediterranean countries, North Africa, the Middle East, India, and Central Asia. α-thalassemia typically results from deletions involving the HBA1 and HBA2 genes. Both of these genes provide instructions for making a protein called α-globin, which is a component (subunit) of hemoglobin. People have two copies of the HBA1 gene and two copies of the HBA2 gene in each cell. The different types of α-thalassemia result from the loss of some or all of the HBA1 and HBA2 alleles.

Hb Bart syndrome, the most severe form of α-thalassemia, results from the loss of all four alpha-globin alleles. HbH disease is caused by a loss of three of the four α-globin alleles. In these two conditions, a shortage of α-globin prevents cells from making normal hemoglobin. Instead, cells produce abnormal forms of hemoglobin called hemoglobin Bart (Hb Bart) or hemoglobin H (HbH). These abnormal hemoglobin molecules cannot effectively carry oxygen to the body's tissues. The substitution of Hb Bart or HbH for normal hemoglobin causes anemia and the other serious health problems associated with α-thalassemia.

Two additional variants of α-thalassemia are related to a reduced amount of α-globin. Because cells still produce some normal hemoglobin, these variants tend to cause few or no health problems. A loss of two of the four α-globin alleles results in α-thalassemia trait. People with α-thalassemia trait may have unusually small, pale red blood cells and mild anemia. A loss of one α-globin allele is found in α-thalassemia silent carriers. These individuals typically have no thalassemia-related signs or symptoms.

In a preferred embodiment, gene therapy methods contemplated herein are used to treat, prevent, or ameliorate a hemoglobinopathy is selected from the group consisting of: hemoglobin C disease, hemoglobin E disease, sickle cell anemia, sickle cell disease (SCD), thalassemia, β-thalassemia, thalassemia major, thalassemia intermedia, α-thalassemia, hemoglobin Bart syndrome and hemoglobin H disease. Without wishing to be bound by any particular theory, the lentiviral vectors contemplated herein reduce or eliminate BCL11A expression in erythroid cells and result in the reactivation or derepression of γ-globin gene expression and a decrease defective β-globin gene expression, and thereby increase HbF expression to effectively treat and/or ameliorate one or more symptoms associated with subjects that have the hemoglobinopathy.

In a preferred embodiment, gene therapy methods contemplated herein are used to treat, prevent, or ameliorate a hemoglobinopathy in a subject having a β-globin genotype selected from the group consisting of: $\beta^E/\beta^0$, $\beta^C/\beta^0$, $\beta^0/\beta^0$, $\beta^E/\beta^E$, $\beta^C/\beta^+$, $\beta^E/\beta^+$, $\beta^0/\beta^+$, $\beta^+/\beta^+$, $\beta^C/\beta^C$, $\beta^E/\beta^S$, $\beta^0/\beta^S$, $\beta^C/\beta^S$, $\beta^+/\beta^S$ or $\beta^S/\beta^S$.

In various embodiments, the retroviral vectors are administered by direct injection to a cell, tissue, or organ of a subject in need of gene therapy, in vivo. In various other embodiments, cells are transduced in vitro or ex vivo with vectors of the invention, and optionally expanded ex vivo. The transduced cells are then administered to a subject in need of gene therapy.

Cells suitable for transduction and administration in the gene therapy methods contemplated herein include, but are not limited to stem cells, progenitor cells, and differentiated cells as described elsewhere herein. In certain embodiments, the transduced cells are hematopoietic stem or progenitor cells as described elsewhere herein.

Preferred cells for use in the gene therapy compositions and methods contemplated herein include autologous/autogeneic ("self") cells.

In particular embodiments, the cells used as the source for gene therapy have the following β-globin alleles: $\beta^E/\beta^0$, $\beta^C/\beta^0$, $\beta^0/\beta^0$, $\beta^E/\beta^E$, $\beta^C/\beta^+$, $\beta^E/\beta^+$, $\beta^0/\beta^+$, $\beta^+/\beta^+$, $\beta^C/\beta^C$, $\beta^E/\beta^S$, $\beta^0/\beta^S$, $\beta^C/\beta^S$, $\beta^+/\beta^S$ or $\beta^S/\beta^S$.

In particular embodiments, the cells used as the source for gene therapy have the following β-globin alleles: $\beta^E/\beta^0$, $\beta^C/\beta^0$, $\beta^0/\beta^0$, $\beta^C/\beta^C$, $\beta^E/\beta^E$, $\beta^E/\beta^+$, $\beta^C/\beta^E$, $\beta^C/\beta^+$, $\beta^0/\beta^+$, or $\beta^+/\beta^+$.

In particular embodiments, the cells used as the source for gene therapy have the following β-globin alleles: $\beta^E/\beta^S$, $\beta^0/\beta^S$, $\beta^C/\beta^S$, $\beta^+/\beta^S$ or $\beta^S/\beta^S$.

A "subject," as used herein, includes any animal that exhibits a symptom of a monogenic disease, disorder, or condition that can be treated with the gene therapy vectors, cell-based therapeutics, and methods disclosed elsewhere herein. In preferred embodiments, a subject includes any animal that exhibits symptoms of a disease, disorder, or condition of the hematopoietic system, e.g., a hemoglobinopathy, that can be treated with the gene therapy vectors, cell-based therapeutics, and methods disclosed elsewhere herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include animals that exhibit aberrant amounts (lower or higher amounts than a "normal" or "healthy" subject) of one or more physiological activities that can be modulated by gene therapy.

As used herein "treatment" or "treating," includes any beneficial or desirable effect on the symptoms or pathology of a disease or pathological condition, and may include even minimal reductions in one or more measurable markers of the disease or condition being treated. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, the term "amount" refers to "an amount effective" or "an effective amount" of a virus or transduced therapeutic cell to achieve a beneficial or desired prophylactic or therapeutic result, including clinical results.

A "prophylactically effective amount" refers to an amount of a virus or transduced therapeutic cell effective to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of a virus or transduced therapeutic cell may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject (e.g., a patient).

Without wishing to be bound to any particular theory, an important advantage provided by the vectors, compositions, and methods of the present invention is the high efficacy of gene therapy that can be achieved by administering populations of cells comprising high percentages of transduced cells compared to existing methods.

The transduced cells may be administered as part of a bone marrow or cord blood transplant in an individual that has or has not undergone bone marrow ablative therapy. In one embodiment, transduced cells of the invention are administered in a bone marrow transplant to an individual that has undergone chemoablative or radioablative bone marrow therapy.

In one embodiment, a dose of transduced cells is delivered to a subject intravenously. In preferred embodiments, transduced hematopoietic stem cells are intravenously administered to a subject.

In one illustrative embodiment, the effective amount of transduced cells provided to a subject is at least $2 \times 10^6$ cells/kg, at least $3 \times 10^6$ cells/kg, at least $4 \times 10^6$ cells/kg, at least $5 \times 10^6$ cells/kg, at least $6 \times 10^6$ cells/kg, at least $7 \times 10^6$ cells/kg, at least $8 \times 10^6$ cells/kg, at least $9 \times 10^6$ cells/kg, or at least $10 \times 10^6$ cells/kg, or more cells/kg, including all intervening doses of cells.

In another illustrative embodiment, the effective amount of transduced cells provided to a subject is about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, or about $10 \times 10^6$ cells/kg, or more cells/kg, including all intervening doses of cells.

In another illustrative embodiment, the effective amount of transduced cells provided to a subject is from about $2 \times 10^6$ cells/kg to about $10 \times 10^6$ cells/kg, about $3 \times 10^6$ cells/kg to about $10 \times 10^6$ cells/kg, about $4 \times 10^6$ cells/kg to about $10 \times 10^6$ cells/kg, about $5 \times 10^6$ cells/kg to about $10 \times 10^6$ cells/kg, $2 \times 10^6$ cells/kg to about $6 \times 10^6$ cells/kg, $2 \times 10^6$ cells/kg to about $7 \times 10^6$ cells/kg, $2 \times 10^6$ cells/kg to about $8 \times 10^6$ cells/kg, $3 \times 10^6$ cells/kg to about $6 \times 10^6$ cells/kg, $3 \times 10^6$ cells/kg to about $7 \times 10^6$ cells/kg, $3 \times 10^6$ cells/kg to about $8 \times 10^6$ cells/kg, $4 \times 10^6$ cells/kg to about $6 \times 10^6$ cells/kg, $4 \times 10^6$ cells/kg to about $7 \times 10^6$ cells/kg, $4 \times 10^6$ cells/kg to about $8 \times 10^6$ cells/kg, $5 \times 10^6$ cells/kg to about $6 \times 10^6$ cells/kg, $5 \times 10^6$ cells/kg to about $7 \times 10^6$ cells/kg, $5 \times 10^6$ cells/kg to about $8 \times 10^6$ cells/kg, or $6 \times 10^6$ cells/kg to about $8 \times 10^6$ cells/kg, including all intervening doses of cells.

Some variation in dosage will necessarily occur depending on the condition of the subject being treated. The person responsible for administration will, in any event, determine the appropriate dose for the individual subject.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

BB694 Lentiviral Vector

A shmiR BCL11A cassette (SEQ ID NO: 1) was cloned from a pD12G5 lentiviral vector into another lentiviral vector backbone to improve shmir expression. The new vector is referred to as BB694. FIG. 1.

The BB694 lentiviral vector differs from the pD12G5 lentiviral vector in at least the following aspects: the BB694 lentiviral vector backbone was derived from the HIV-1 NL43strain, whereas the pD12G5 lentiviral vector backbone is based on the HIV-1 HXB2 strain; the architecture of the lentiviral vector elements in BB694 is 5' LTR-psi (T) packaging signal-cPPT/FLAP-RRE-env splice acceptor (S/A) site, whereas the architecture of the lentiviral vector elements in BB694 is 5' LTR-psi (T) packaging signal-RRE-env S/A-cPPT/FLAP; the BB694 lentiviral vector comprises a polynucleotide encoding a truncated gag protein of about 459 nucleotides and that has at least two mutated ATG codons, whereas the pD12G5 lentiviral vector comprises a polynucleotide encoding a truncated gag protein of about 339 nucleotides and that has no mutated ATG codons; the BB694 lentiviral vector comprises an env splice acceptor (S/A) site of about 176 nucleotides, whereas the D12G5 lentiviral vector comprises an env S/A of about 334 nucleotides; the BB694 lentiviral vector comprises a cPPT/FLAP sequence of about 381 nucleotides, whereas the D12G5 lentiviral vector comprises a cPPT/FLAP sequence of about 118 nucleotides; the BB694 lentiviral vector comprises an HS2 DNAse I hypersensitive site of about 638 nucleotides, whereas the D12G5 lentiviral vector comprises an HS2 DNAse I hypersensitive site of about 1435 nucleotides; the BB694 lentiviral vector comprises an HS3 DNAse I hypersensitive site of about 847 nucleotides, whereas the D12G5 lentiviral vector comprises an HS3 DNAse I hypersensitive site of about 1202 nucleotides; and the BB694 lentiviral vector comprises a synthetic polyadenylation sequence, whereas the D12G5 lentiviral vector comprises a polyadenylation sequence from the bovine growth hormone gene.

The aspects of the BB694 vector and their positions are set forth in Table 1 and SEQ ID NO: 4.

TABLE 1

| bb694. | |
| --- | --- |
| Nucleotides | Identity |
| 1-185 | pUC19 plasmid backbone |
| 185-202 | Linker |
| 203-800 | CMV |
| 801-1136 | R, U5, PBS, and packaging sequences |
| 1137-1139 | Gag start codon (ATG) changed to stop codon (TAG) |
| 1140-1240 | HIV-1 gag sequence |
| 1241-1243 | HIV-1 gag sequence changed to a second stop codon |

TABLE 1-continued bb694.

| Nucleotides | Identity |
| --- | --- |
| 1244-1595 | HIV-1 gag sequence |
| 1596-1992 | HIV-1 pol; cPPT/CTS |
| 1993-2517 | HIV-1, isolate HXB3 env region (RRE) |
| 2518-2693 | HIV-1 env S/A sequences |
| 2694-2699 | Linker |
| 2700-2747 | Synthetic PolyA signal |
| 2748-2775 | Linker |
| 2776-2859 | miR223 |
| 2860-2916 | D12 hairpin |
| 2917-2968 | miR223 |
| 2969-3004 | Linker |
| 3005-3321 | b-globin exon1 containing 5' UTR and promoter |
| 3322-3960 | HS2 |
| 3961-3973 | Linker |
| 3974-4820 | HS3 |
| 4821-4859 | Linker |
| 4860-4965 | HIV-1 ppt and part of U3 |
| 4966-5082 | HIV-1 part of U3 (399 bp deletion) and R |
| 5083-5106 | Synthetic poly(A) |
| 5107-5124 | Linker |
| 5125-7294 | pUC19 backbone, contains Amp R |
| 7295-7297 | Linker |
| 7298-7499 | SV40 ori |
| 7500-7547 | Linker |
| 7548-7598 | pUC19 backbone |

Example 2

BB694 Lentiviral Vector Induces Fetal Hemoglobin in Normal Erythroid Cells and in Erythroid Cells Containing a Sickle Cell Disease Mutation Background The characteristics of pD12G5 and BB694 lentiviral vectors were compared. Both vectors comprise a shmiR directed against BCL11A mRNA. BCL11A is transcription factor that regulates γ-globin gene expression to therefore contributes to regulation of fetal hemoglobin levels (HbF) (Bauer et al., *Science* 2013). Diminished BCL11A expression correlates with elevated HbF. However, reduced BCL11A expression also causes apoptosis in early B cells and CLPs and completely abolishes the lymphoid development potential of HSCs to B, T, and NK cells (Yu et al., *JEM* 2012). In addition, BCL11A-deficiency leads to hematopoietic stem cell defects with an aging-like phenotype (Luc et al., *Cell Rep* 2016). Use of an erythroid specific promoter/enhancer driving expression of the BCL11A shmir allows BCL11A to properly function during development.

Lentiviral vector was prepared for D12G5 and BB694. Four liters of D12G5 were harvested with a titer of $2.03 \times 10^6$ TU/mL (qPCR titer on HOS cells) and concentrated to a final volume of 23 mL with a titer of $1.25 \times 10^8$ TU/mL. Two liters of BB694 were harvested with a titer of $13.7 \times 10^6$ TU/mL (qPCR titer on HOS cells) and concentrated to a final volume of 30 mL with a titer of $5.65 \times 10^8$ TU/mL. Overall, the yield of BB694 was much greater (59%) than it was for D12G5 (35%).

Transduction of CD34+ Cells

Human (h) CD34+ cells were isolated from normal donors or from subjects have sickle cell disease and prestimulated at $1 \times 10^6$ cells/mL for 48 h in CellGro® Serum-free Media (CellGenix) supplemented with hSCF, hTPO, and hFlt-3L in a standard humidified tissue culture incubator (5% $CO_2$). Then cells were enumerated, distributed into 21 wells (3 replicates per condition) and transduced at $4 \times 10^6$ cells/mL for 24 h according to the experimental design summarized in Table 2.

TABLE 2

Experimental Design Summary

| Transduction Conditions | Wells # |
| --- | --- |
| Normal hCD34+ cells, MOCK transduction | 1, 2, 3 |
| Normal hCD34+ cells transduced with BB694 (MOI 25) + protamine sulfate | 4, 5, 6 |
| Normal hCD34+ cells transduced with BB694 (MOI 25) + F108 + PGE$_2$ | 7, 8, 9 |
| Normal hCD34+ cells transduced with BB694 (MOI 50) + protamine sulfate | 10, 11, 12 |
| Normal hCD34+ cells transduced with BB694 (MOI 50) + F108 + PGE$_2$ | 13, 14, 15 |
| Normal hCD34+ cells transduced with D12G5 (MOI 25) + protamine sulfate | 16, 17, 18 |
| Normal hCD34+ cells transduced with D12G5 (MOI 25) + F108 + PGE$_2$ | 19, 20, 21 |
| SCD hCD34+ cells, MOCK transduction | 22, 23, 24 |
| SCD hCD34+ cells transduced with BB694 (MOI 25) + protamine sulfate | 25, 26, 27 |
| SCD hCD34+ cells transduced with BB694 (MOI 25) + F108 + PGE$_2$ | 28, 29, 30 |
| SCD hCD34+ cells transduced with BB694 (MOI 50) + protamine sulfate | 31, 32, 33 |
| SCD hCD34+ cells transduced with BB694 (MOI 50) + F108 + PGE$_2$ | 34, 35, 36 |
| SCD hCD34+ cells transduced with D12G5 (MOI 25) + protamine sulfate | 37, 38, 39 |
| SCD hCD34+ cells transduced with D12G5 (MOI 25) + F108 + PGE$_2$ | 40, 41, 42 |

Protamine sulfate was used at 8 µg/mL, F108 at 200 µg/mL, PGE$_2$ at 10 µM

After the transduction, cells were washed with phosphate buffered saline (PBS). 500 cells per condition were used for clonogenic culture (MethoCult, H4434, StemCell Technologies) and the remaining cells were divided equally between liquid culture in SCGM for day 6 (D6) VCN assessment and erythroid differentiation in liquid culture for hemoglobin analysis.

Liquid Culture in SCGM for D6 VCN Assessment

Figure 2:
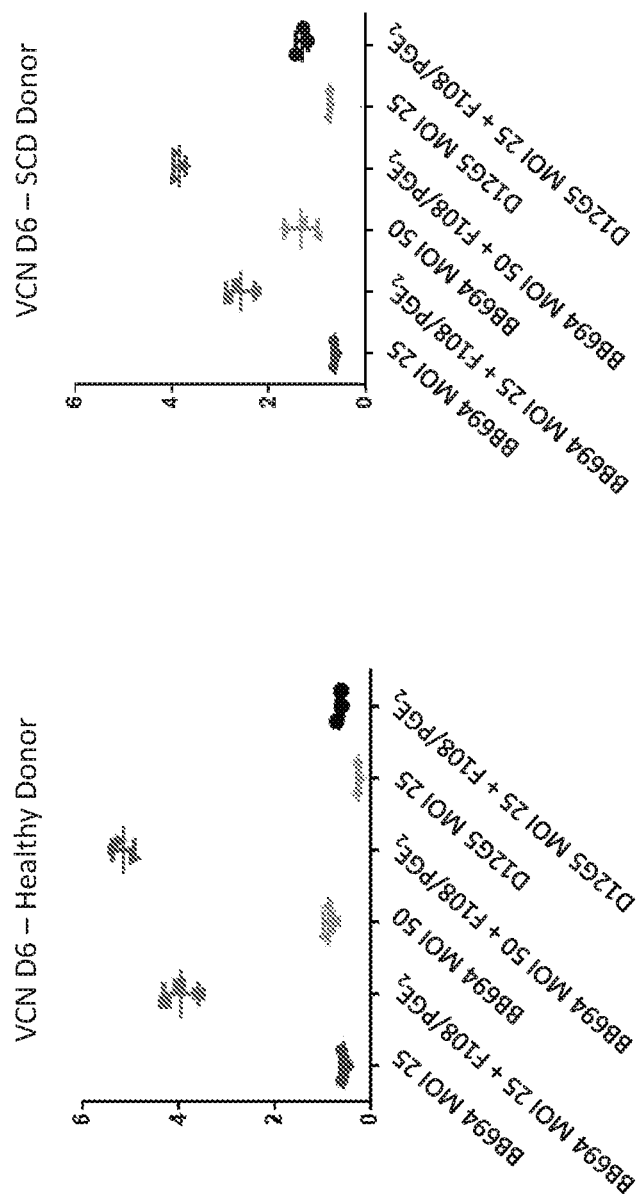
FIG. 2 shows representative VCNs from normal healthy donor and SCD CD34$^+$ cells transduced under various conditions and after 6 days in liquid culture.

Transduced hCD34+ cells were cultured in SCGM for VCN assessment in CellGro® Serum-free Media (CellGenix) supplemented with hSCF, hTPO, hFlt-3L, and IL-3 for 6 days in a standard humidified tissue culture incubator (5% $CO_2$). The cells were harvested, genomic DNA extraction was extracted, and the average vector copy number per diploid genome was determined by qPCR. The D6 VCNs for the transduction conditions in Table 2 are shown in FIG. 2.

Figure 3A:
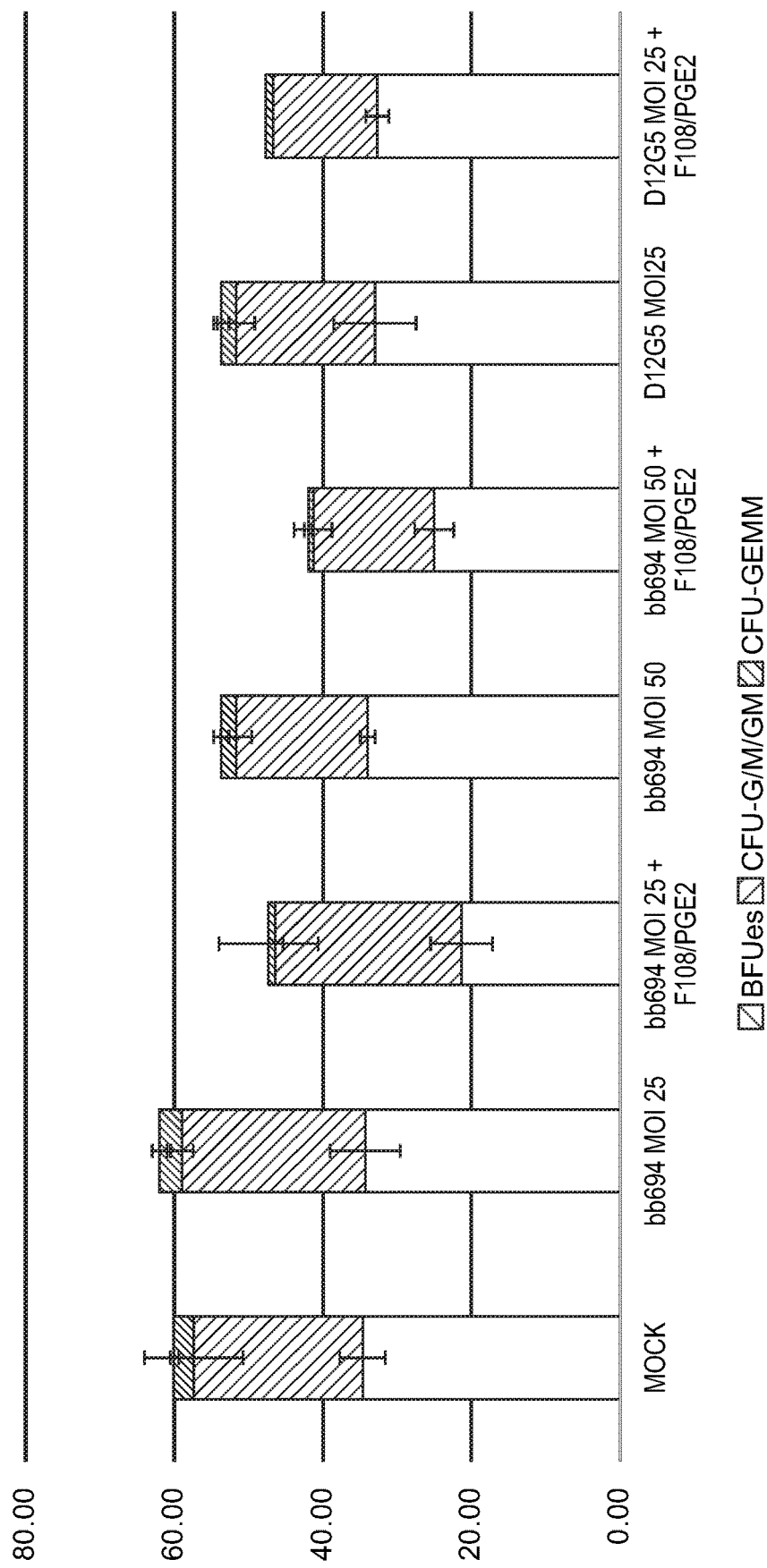
FIG. 3A shows clonogenic analysis of normal healthy donor CD34$^+$ cells transduced under various conditions and after 14 days in methylcellulose culture.
Figure 3B:
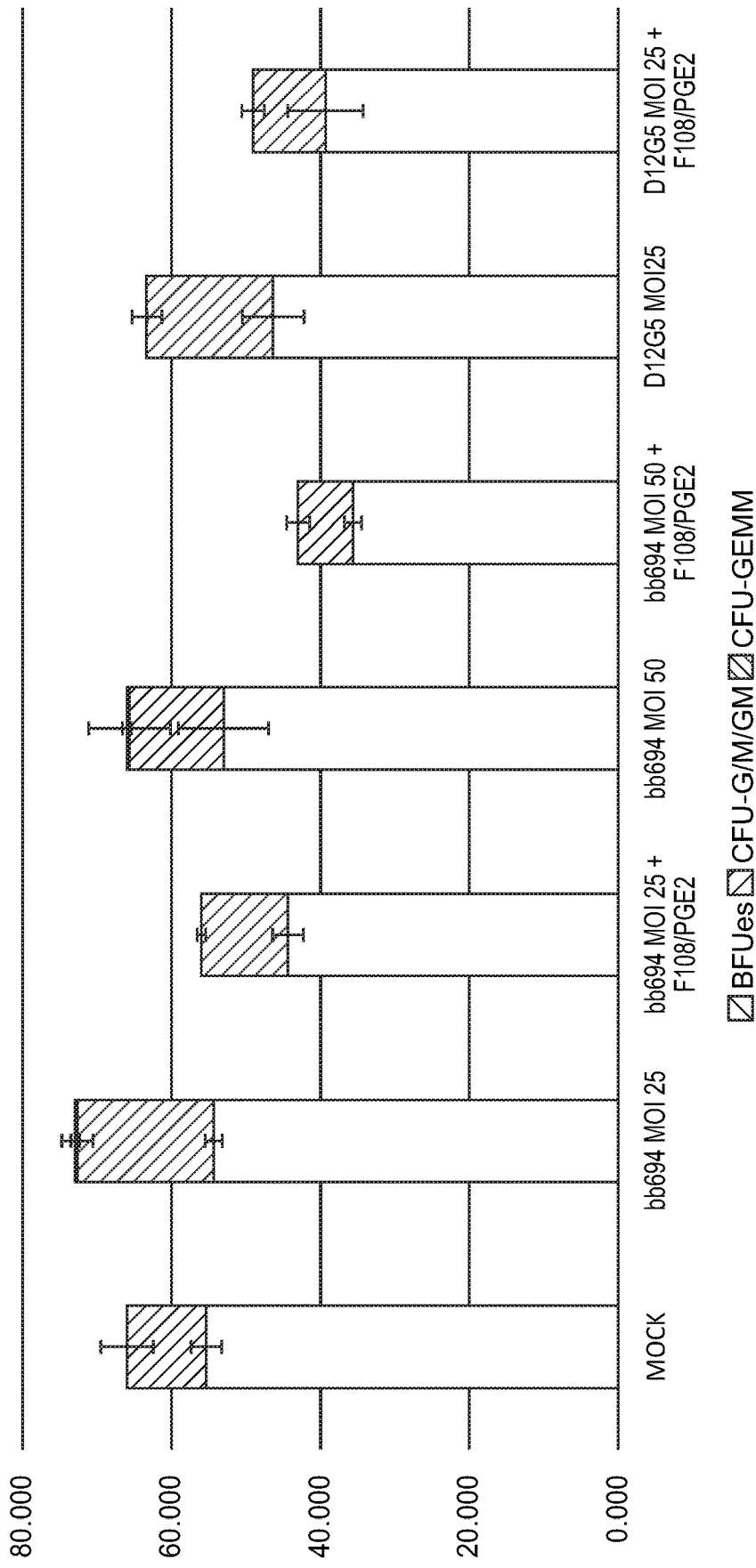
FIG. 3B shows clonogenic analysis of SCD CD34$^+$ cells transduced under various conditions and after 14 days in methylcellulose culture.

Clonogenic Assay 500 cells from each transduction condition were washed and transferred to 3 mL aliquots of cytokine-supplemented methylcellulose (for example, Methocult M4434 Classic). 1.1 mL was then transferred to parallel 35-mm tissue culture dishes using a blunt 16-gauge needle. Dishes were maintained in a standard humidified tissue culture incubator for 14-16 days at 37° C. and 5% $CO_2$ and colonies were scored for size, morphology, and cellular composition. The transduction conditions did not lead to unexpected differences in clonogenic frequency or increase toxicity. FIGS. 3A-3B.

Figure 4:
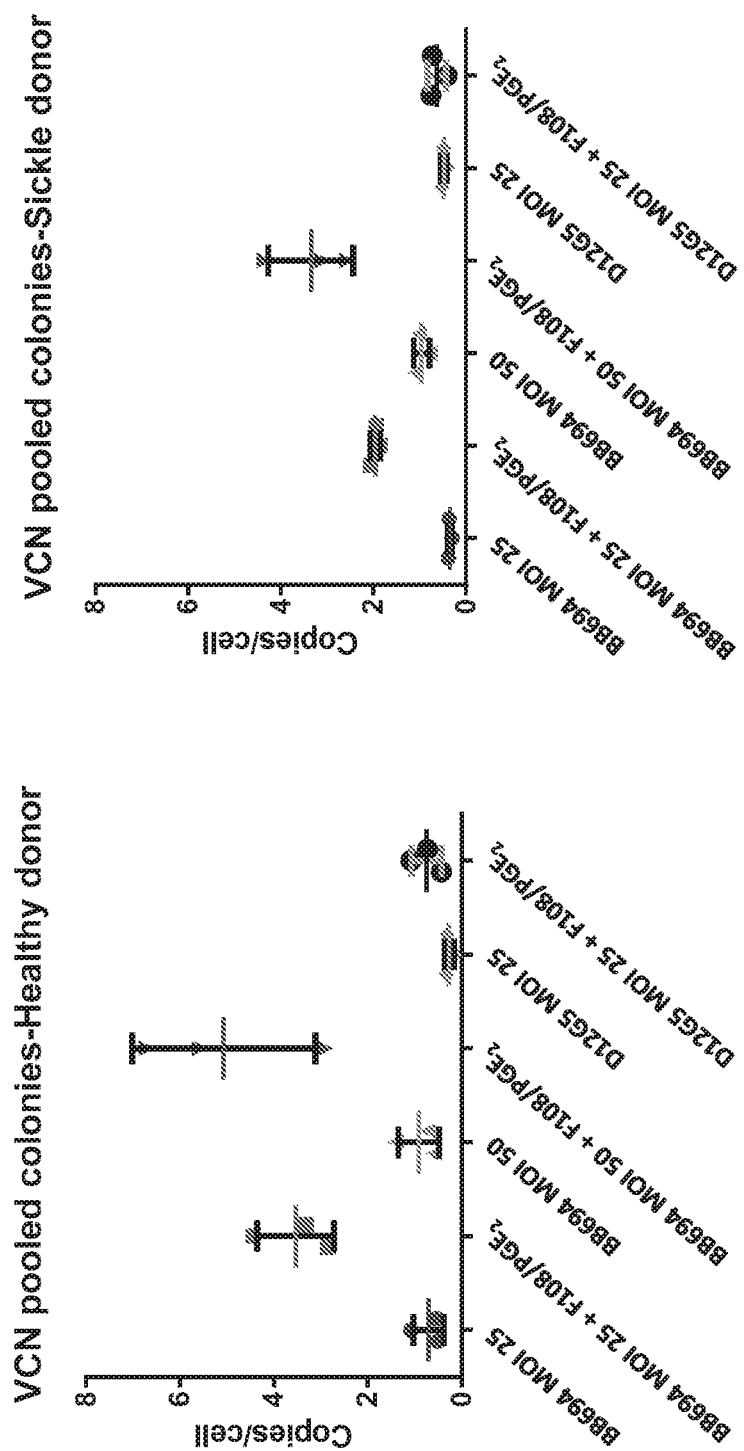
FIG. 4 shows the VCN of pooled colonies from normal healthy donor and SCD CD34$^+$ cells transduced under various conditions and after 14 days in methylcellulose culture.

Individual colonies were pooled and subjected to VCN analysis. FIG. 4.

Erythroid Differentiation in Liquid Culture

About half of the transduced cells were cultured in erythroid differentiation media in a standard humidified tissue culture incubator for 14-16 days at 37° C. and 5% $CO_2$. The erythroid differentiation media (HF media) comprises IMDM supplemented with Pen/Strep, hSCF, hIL-3, erythropoietin (R&D #287-TC), and 20% heat-inactivated FBS (Lot 1658396). After 14 days, cells were centrifuged (~300 g 10 min), washed in PBS and lysed in HPLC grade water. After high speed centrifugation (20 000 g 30 min 4° C.), hemoglobin content in the supernatant was analyzed by ion-exchange high-performance liquid chromatography (HPLC).

Hemoglobin Analysis by HPLC

Hemoglobins were analyzed with a Prominence chromatograph (Shimadzu): DGU-20A 3R degassing unit, two LC-20AD mobile phase delivery units (pumps), in series with a CBM-20A system controller, a SIL-20AC HT autosampler, a CTO-20AC column oven and a SPO-20A dual wavelength UV-vis detector. Automated sample injections were performed with SIL-20AC HT autosampler.

One to thirty microliters of the supernatant was injected onto a 100×2.1 mm, 5 μm diameter particle size with 1000-angstrom pores, PolyCAT A column (PolyLC, Columbia, Md.). Hemoglobins were eluted with a gradient of two Tris buffers (buffer A: Tris 40 mM, KCN 3 mM, and adjusted at pH 6.5 with acetic acid; buffer B: Tris 40 mM, KCN 3 mM, NaCl 200 mM, adjusted at pH 6.5 with acetic acid) of different ionic strength at a flow rate of 0.3 ml/minute. The gradients used were 0-2 minutes, 2% B; 2-6 minutes, 20% B; 8-12 minutes, 60% B; 12-12:30 minutes 100% B; and 13 minutes, 2% B. The column oven was set at 30° C. The detection wavelength was 418 nm. Data acquisition and date analysis were performed with the software LC Solution from Shimadzu. Hemoglobins were identified thanks to their retention time and a reference standard run in the same batch. The proportion of the different hemoglobins was assessed with the peak area of each peak at 418 nm.

Figure 5:
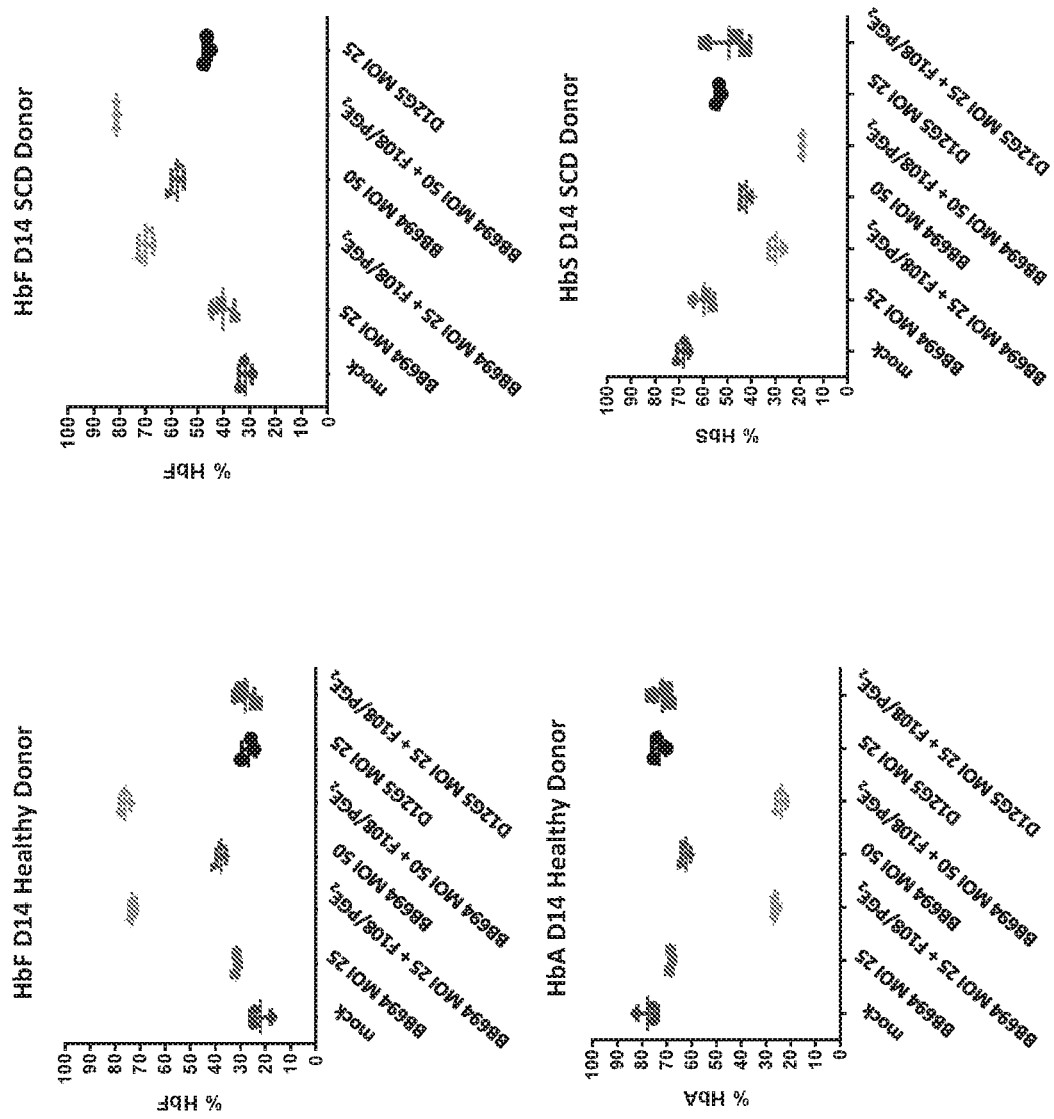
FIG. 5 shows the HbF and HbA levels from normal healthy donor CD34$^+$ cells transduced under various conditions and after day 14 erythroid differentiation culture (left panels).

FIG. 5 shows the relative fetal hemoglobin, normal hemoglobin, and sickled hemoglobin levels produced by erythroid cells derived from the healthy (left panel) and SCD (right panel) CD34$^+$ donor cells transduced under the conditions in Table 2.

Vector Positive Colonies and HbF Production

Erythroid colonies were plucked individually under a microscope. The colonies were washed in PBS (~300 g 10 min) and resuspended in 100 μL of HPLC grade water. 20 μL was used for VCN assessment by qPCR and 80 μL was used for hemoglobin analysis by Ion-Exchange HPLC.

Figure 6:
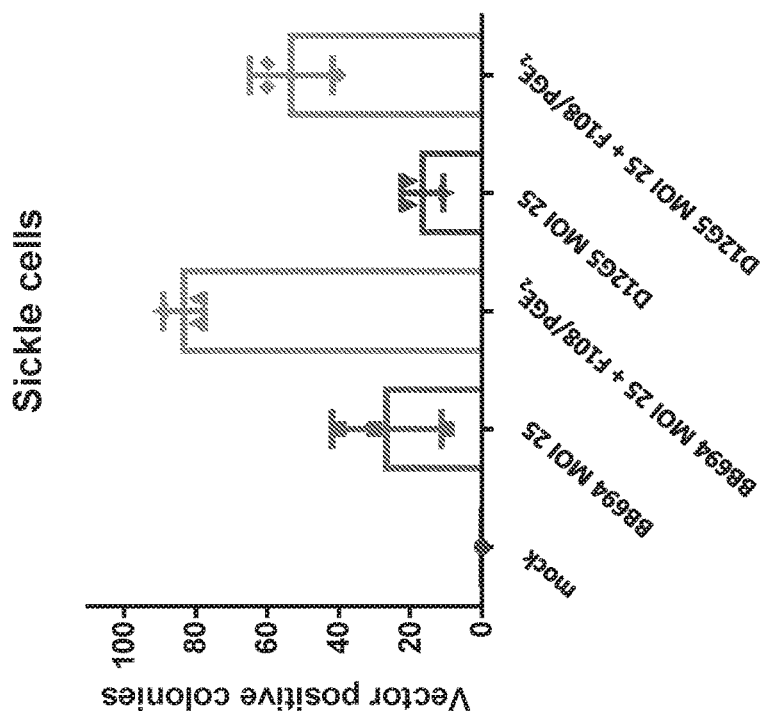
FIG. 6 shows percent vector positive erythroid colonies from day 14 erythroid differentiation cultures from normal healthy donor and sickle cell CD34$^+$ cells transduced under various conditions.
Figure 6:
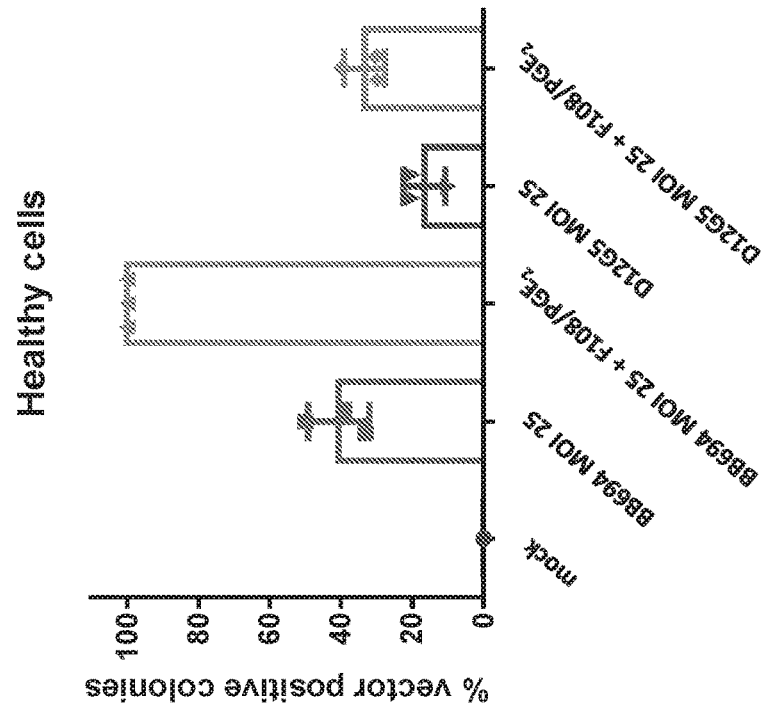

The percent vector positive colonies are shown in FIG. 6. Transduction in the presence of bb694, F108, and PGE$_2$ resulted in greater than 80% transduced cells in both normal human donor cells and SCD cells.

Figure 7:
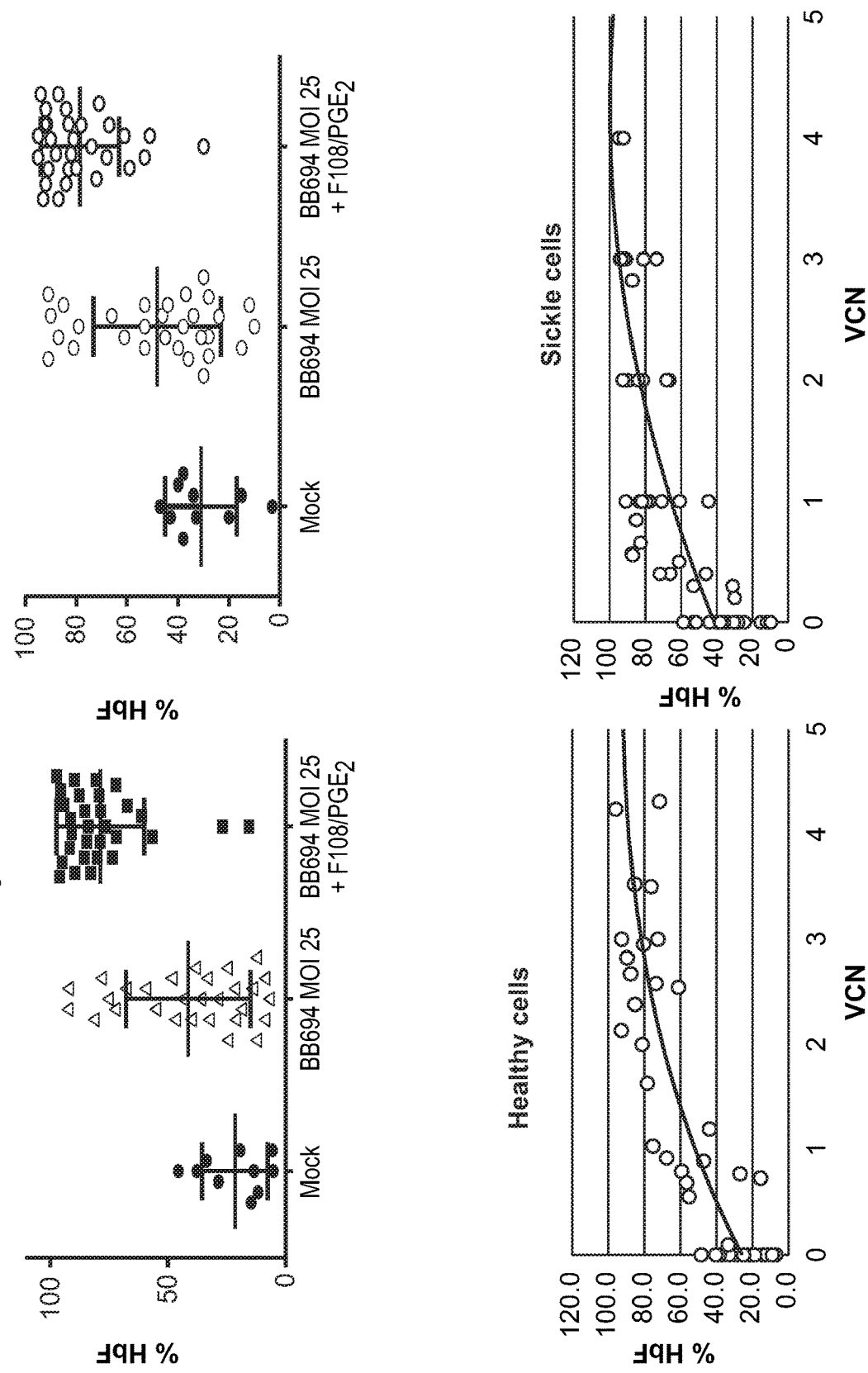
FIG. 7 shows the percent HbF induction from individual BFUe colonies from normal healthy donor and sickle cell CD34$^+$ cells transduced under various conditions.

As expected, HbF background is high (up to 50%) in colonies. However, none of MOCK colonies has HbF >50%, and more than 93% of colonies produced by transduction with bb694, F108, and PGE$_2$ have HbF >50%. FIG. 7. The percentage of HbF increases when the VCN is increased and plateaus between 80% and 100% when the average vector copy number per diploid genome is higher than 5.

Conclusion

The bb694 lentiviral vector was superior to the D12G5 vector under all conditions tested. bb694 lentiviral vector was produced at high titer (>1.10$^8$ TU/mL), it was able to transduce around 40% of erythroid progenitors at MOI 25 and more than 80% of erythroid progenitors at MOI of 25 in the presence of F108 and PGE$_2$. Under the latter conditions, the percentage of HbF was higher than 70%.

Example 3

Engraftment Potential of HCD34$^+$ Cells Transduced with BB694 Lentiviral Vector Administered to NSG Mice The engraftment potential of hCD34$^+$ cells transduced with bb694 lentiviral vector was evaluated in an NSG mouse model.

hCD34$^+$ cells were prestimulated at 1×10$^6$ cells/mL for 48 h in serum-free media supplemented with hSCF, hTPO, and hFlt-3L in a standard humidified tissue culture incubator (5% CO$_2$). After prestimulation, cells were transduced at 2-4×10$^6$ cells/mL for 24 h in SCGM hSCF 100 ng/mL, hTPO 100 ng/mL, hFlt-3L 100 ng/mL with bb694 (6E+8 TU/mL) at a MOI of 30 and in presence of F108 and PGE$_2$.

Female NOD-Cg-PrkdcscidIl2rgtm 1 Wjl/Sz (NSG) mice were conditioned with 40 mg/kg busulfan and transplanted by single intravenous administration with human CD34$^+$ cell transduced with bb694 lentiviral vector or mock transduced cells.

Figure 8:
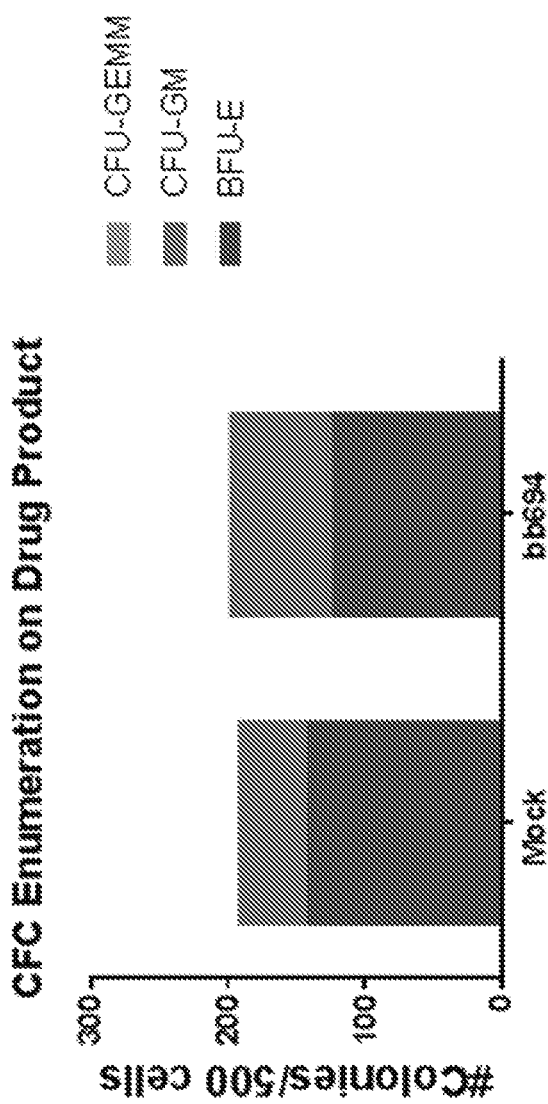
FIG. 8 shows the clonogenic analysis of mock transduced normal healthy donor CD34$^+$ cells or CD34$^+$ cells transduced with bb694 after 14-16 days in methylcellulose culture.

For each condition, 500 washed cells were transferred to 3 mL aliquots of cytokine-supplemented methylcellulose (for example, Methocult M4434 Classic). 1.1 mL was then transferred to a 35-mm tissue culture dish a cultured for 14-16 days at 37° C. and 5% CO$_2$. Colonies were scored for size, morphology, and cellular composition. Individual colonies were picked for subsequent Vector Copy Number analysis or the contents of an entire 35-mm dish were pooled and then subjected to Vector Copy Number analysis. The number of colonies for 500 cells plated in methyl cellulose are shown in FIG. 8. No statically significant difference between the two groups was observed.

Erythroid colonies were plucked individually under a microscope. Each colony was then analyzed by individual colony qPCR for VCN and % LVV positive colonies. FIG. 9.

Figure 10:
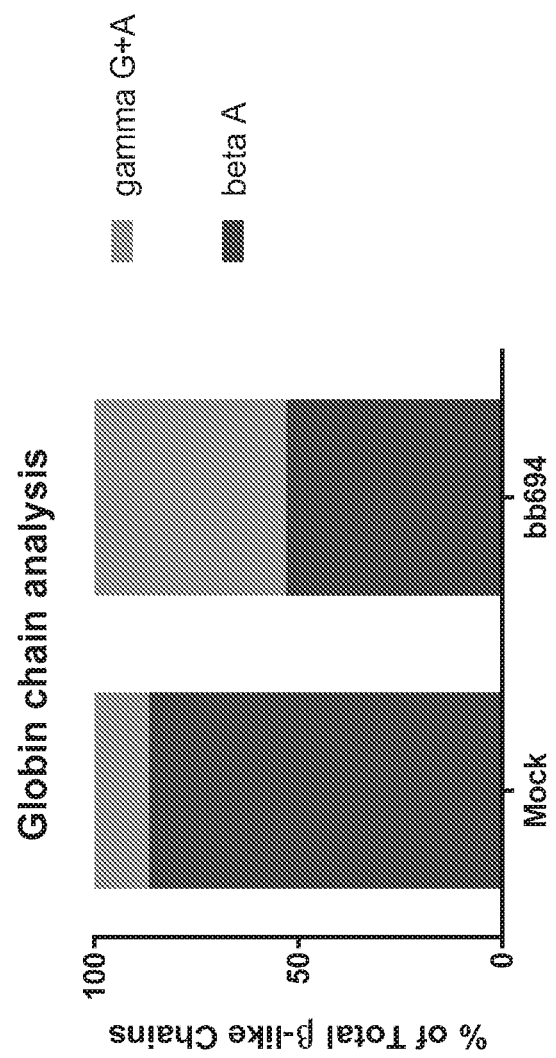
FIG. 10 shows the globin chain analysis of erythroid cells differentiated from mock transduced hCD34$^+$ cells or hCD34$^+$ cells transduced with BB694 lentiviral vector.

About half of the transduced cells was cultured in erythroid differentiation media in a standard humidified tissue culture incubator for 14-16 days at 37° C. and 5% CO$_2$. The erythroid differentiation media. After 14 days, the cells were centrifuged (~300 g 10 min), washed in PBS and lysed in HPLC grade water. After high speed centrifugation (20,000 g 30 min 4° C.), supernatant was used to analyze globin chains by Reverse Phase HPLC. FIG. 10.

Figure 11:
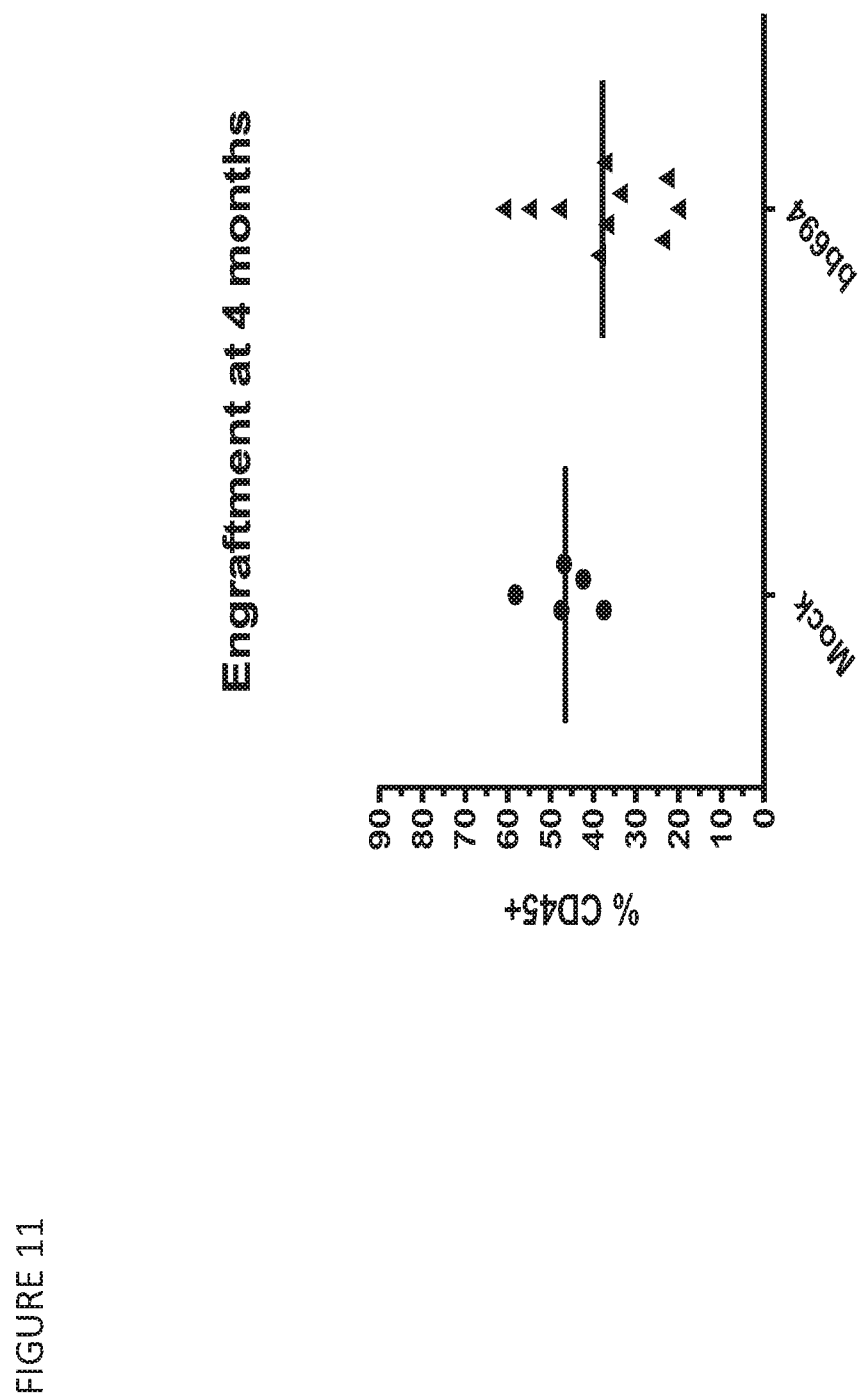
FIG. 11 shows the percentage of hCD45$^+$ cells from the bone marrow of NSG mice transplanted with mock transduced hCD34$^+$ cells or hCD34$^+$ cells transduced with BB694 lentiviral vector.
Figure 12:
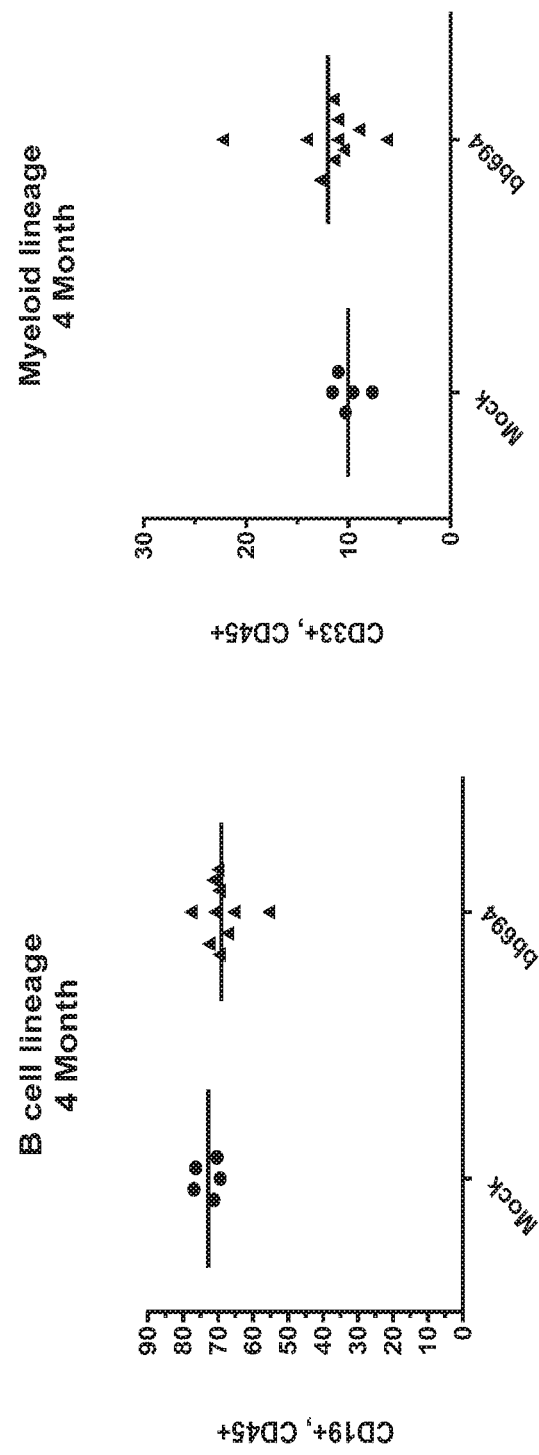
FIG. 12 shows the percentage of CD19$^+$CD45$^+$ cells and the percentage of CD33$^+$CD45$^+$ cells from the bone marrow of NSG mice transplanted with mock transduced hCD34$^+$ cells or hCD34$^+$ cells transduced with BB694 lentiviral vector.

Bone marrow cells from transplanted NSG mice were analyzed by flow cytometric using the following antibodies: CD3 (#560835), CD19 (#560353), CD33 (#555450), CD45 (#561864) and BD flow cytometer. The percentage of hCD45$^+$ cells was assessed to evaluate the engraftment of transduced hCD34$^+$ cells. No statistically significant difference between the mock- and bb694-transduced cells was observed. FIG. 11. The percentage of CD19$^+$CD45$^+$ cells and the percentage of CD33$^+$CD45$^+$ cells were assessed to analyze the balance between B cells and myeloid cells. No statically significant difference between the two groups was observed. FIG. 12.

Figure 13:
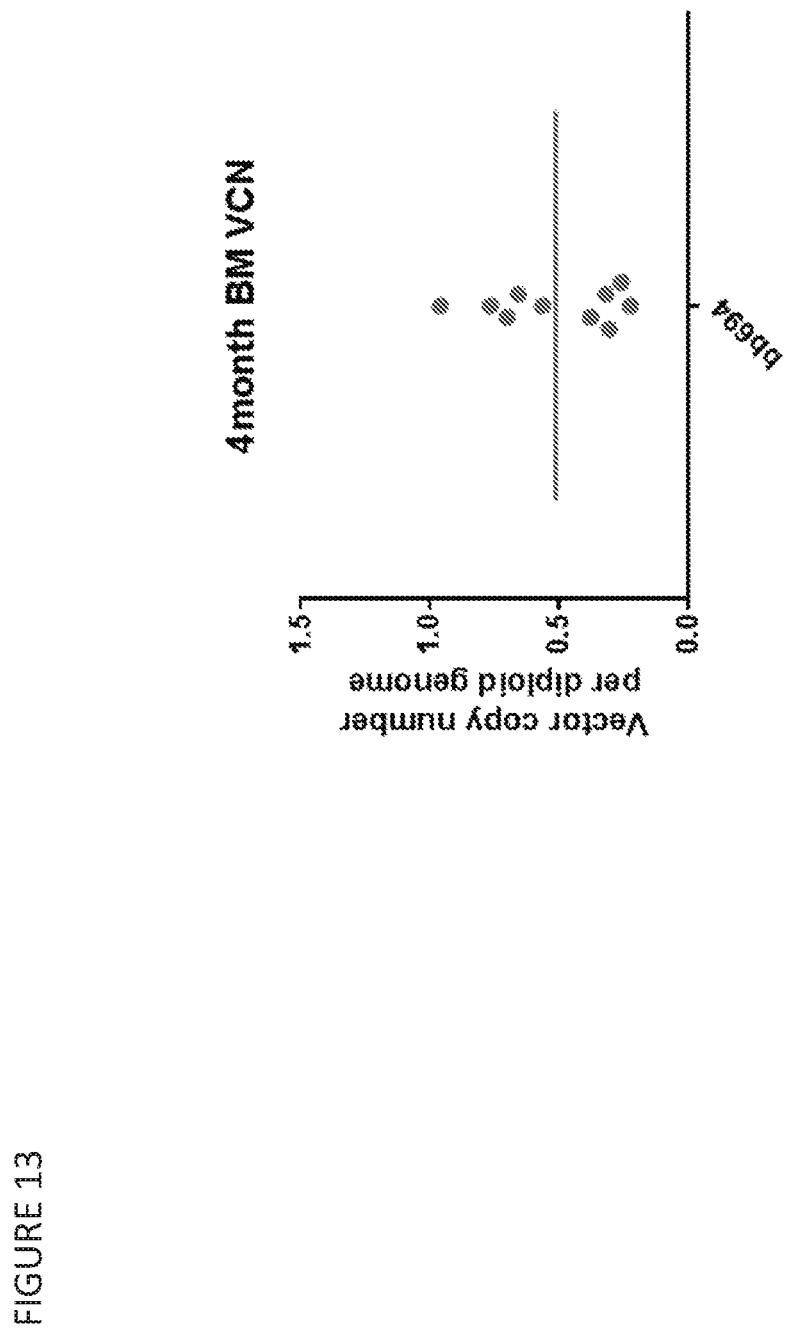
FIG. 13 shows quantitative PCR (qPCR) assessment of genomic DNA harvested from bone marrow cells four months after transplantation.

Four months after transplantation, bone marrow cells were harvested, genomic DNA was extracted and the average vector copy number per diploid genome was assessed by quantitative PCR (qPCR). FIG. 13.

Human CD34$^+$ cells were efficiently transduced with bb694 (3.1 cpd on pooled colonies) and a 3.5-fold induction of hemoglobin F was observed after erythroid differentiation in liquid culture (gamma chains proportion of 13.5% with Mock and 47% with bb694). The frequency of colonies assessed on cells post-transduction was similar for the two groups. The level of engraftment of human CD45$^+$ cells was in the expected range and was not statistically different between the two groups. No lineage skewing was observed. There was no statically significant difference between groups for the percentage of CD19$^+$CD45$^+$ cells or the percentage of CD33$^+$CD45$^+$ cells.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A self-inactivating (SIN) lentiviral vector comprising:
(a) an HIV-1 strain NL4-3 5' long terminal repeat (LTR) modified by replacement of the endogenous 5' LTR promoter with a CMV promoter;
(b) a Psi (Ψ) packaging signal;
(c) an HIV-1 strain NL4-3 central polypurine tract (cPPT)/FLAP element;
(d) an HIV-1 strain HXB3 RRE RNA export element;
(e) an HIV-1 strain NL4-3 env splice acceptor sequence;

a human β-globin promoter operably linked to a polynucleotide encoding a shmiR that comprises an antisense sequence that hybridizes to a human BCL11A mRNA, wherein the shmiR comprises the sequence set forth in SEQ ID NO: 1;

(g) a human β-globin LCR comprising a HS2 DNAse I hypersensitive site comprising about 638 nucleotides, and a HS3 DNAse I hypersensitive site comprising about 847 nucleotides; and (h) an HIV-1 strain NL4-3 3' SIN LTR.

2. The lentiviral vector of claim 1, wherein the lentiviral vector does not comprise an HS4 DNAse I hypersensitivity site.

3. The lentiviral vector of claim 1, further comprising:
(a) a polynucleotide of about 459 nucleotides that encodes a gag protein; comprising one or more mutated ATG start codons and/or
(b) a synthetic poly(A) sequence disposed between an HIV-1 env splice acceptor sequence and the shmiR.

4. The lentiviral vector of claim 1, wherein:
(a) the HIV-1 env splice acceptor sequence comprises about 176 nucleotides; and/or
(b) the cPPT/FLAP element comprises about 381 nucleotides.

5. The lentiviral vector of claim 1, wherein the vector comprises an expression cassette comprising the erythroid specific promoter and the polynucleotide encoding the shmiR are in the reverse orientation compared to the transcription of the lentiviral genomic RNA.

6. A lentiviral transfer vector comprising the polynucleotide sequence set forth in SEQ ID NO: 4.

7. A cell comprising the lentiviral transfer vector of claim 6.

8. A lentiviral vector particle produced from the cell of claim 7.

9. A cell transduced with the lentiviral vector particle of claim 8.

10. The cell of claim 9, wherein the cell is a hematopoietic stem cell or hematopoietic progenitor cell.

11. A composition comprising a population of cells comprising a plurality of the cells according to claim 9.

12. A method of transducing a population of hematopoietic cells comprising culturing the cells in a culture medium, in the presence of a lentiviral vector according to claim 1.

13. A method of treating a hemoglobinopathy in a subject comprising administering the subject an effective amount of a composition according to claim 11.

* * * * *

SEQUENCE LISTING

<160> NUMBER OF SEQ ID NOS: 4

<210> SEQ ID NO 1
<211> LENGTH: 193
<212> TYPE: DNA
<213> ORGANISM: Artificial Sequence
<220> FEATURE:
<223> OTHER INFORMATION: Made in Lab - shmirR BCL11A cassette

<400> SEQUENCE: 1

```
gatctcactt ccccacagaa gctcttggcc tggcctcctg cagtgccacg ctgcgcgatc    60
gagtgttgaa taactccatg tggtagagtt attcaacact cgatcgcgca gtgcggcaca   120
tgcttaccag ctctaggcca gggcagatgg gatatgacga atggactgcc agctggatac   180
aaggatgctc acc                                                      193
```

<210> SEQ ID NO 2
<211> LENGTH: 21
<212> TYPE: DNA
<213> ORGANISM: Artificial Sequence
<220> FEATURE:
<223> OTHER INFORMATION: Made in Lab - shmirR guide strand

<400> SEQUENCE: 2

```
ttattcaaca ctcgatcgcg c                                              21
```

<210> SEQ ID NO 3
<211> LENGTH: 17
<212> TYPE: DNA
<213> ORGANISM: Unknown
<220> FEATURE:
<223> OTHER INFORMATION: Target sequence that hybridizes to shmiR guide
      strand

<400> SEQUENCE: 3

```
gatcgagtgt tgaataa                                                   17
```

<210> SEQ ID NO 4
<211> LENGTH: 7598
<212> TYPE: DNA
<213> ORGANISM: Artificial Sequence
<220> FEATURE:
<223> OTHER INFORMATION: Made in Lab - lentiviral transfer vector
      construct BB694

<400> SEQUENCE: 4

```
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg   120 ttggcgggtg tcggggctgg cttaactatg cggcatcaga gcagattgta ctgagagtgc   180
accatcatat gccagcctat ggtgacattg attattgact agttattaat agtaatcaat   240
tacggggtca ttagttcata gcccatatat ggagttccgc gttacataac ttacggtaaa   300
tggcccgcct ggctgaccgc ccaacgaccc ccgcccattg acgtcaataa tgacgtatgt   360
tcccatagta acgccaatag ggactttcca ttgacgtcaa tgggtggagt atttacggta   420
aactgcccac ttggcagtac atcaagtgta tcatatgcca agtacgcccc ctattgacgt   480
caatgacggt aaatggcccg cctggcatta tgcccagtac atgaccttat gggactttcc   540
tacttggcag tacatctacg tattagtcat cgctattacc atggtgatgc ggttttggca   600
gtacatcaat gggcgtggat agcggtttga ctcacgggga tttccaagtc tccaccccat   660
tgacgtcaat gggagtttgt tttggcacca aaatcaacgg gactttccaa aatgtcgtaa   720
```

```
caactccgcc ccattgacgc aaatgggcgg taggcgtgta cggtgggagg tctatataag    780
cagagctcgt ttagtgaacc gggtctctct ggttagacca gatctgagcc tgggagctct    840
ctggctaact agggaaccca ctgcttaagc ctcaataaag cttgccttga gtgctcaaag    900
tagtgtgtgc ccgtctgttg tgtgactctg gtaactagag atccctcaga ccctttttagt   960 cagtgtggaa aatctctagc agtggcgccc gaacagggac ttgaaagcga agtaaagcc    1020 agaggagatc tctcgacgca ggactcggct tgctgaagcg cgcacggcaa gaggcgaggg   1080
gcggcgactg gtgagtacgc caaaaatttt gactagcgga ggctagaagg agagagtagg   1140
gtgcgagagc gtcggtatta agcgggggag aattagataa atgggaaaaa attcggttaa   1200
ggccaggggg aaagaaacaa tataaactaa acatatagt tagggcaagc agggagctag   1260
aacgattcgc agttaatcct ggccttttag agacatcaga aggctgtaga caaatactgg   1320
gacagctaca accatcccctt cagacaggat cagaagaact tagatcatta tataatacaa   1380
tagcagtcct ctattgtgtg catcaaagga tagatgtaaa agacaccaag gaagccttag   1440
ataagataga ggaagagcaa aacaaaagta agaaaaaggc acagcaagca gcagctgaca   1500
caggaaacaa cagccaggtc agccaaaatt accctatagt gcagaacctc caggggcaaa   1560
tggtacatca ggccatatca cctagaactt taaattaaga cagcagtaca aatggcagta   1620
ttcatccaca atttttaaaag aaagggggg attgggggt acagtgcagg ggaaagaata   1680
gtagacataa tagcaacaga catacaaact aaagaattac aaaaacaaat tacaaaaatt   1740 caaaatttc gggtttatta cagggacagc agagatccag tttggaaagg accagcaaag   1800
ctcctctgga aaggtgaagg ggcagtagta atacaagata atagtgacat aaaagtagtg   1860
ccaagaagaa aagcaaagat catcagggat tatggaaaac agatggcagg tgatgattgt   1920
gtggcaagta gacaggatga ggattaacac atggaaaaga ttagtaaaac accatagctc   1980
tagagcgatc ccgatcttca gacctggagg aggagatatg agggacaatt ggagaagtga   2040
attatataaa tataaagtag taaaaattga accattagga gtagcaccca ccaaggcaaa   2100
gagaagagtg gtgcagagag aaaaaagagc agtgggaata ggagctttgt tccttgggtt   2160
cttgggagca gcaggaagca ctatgggcgc agcgtcaatg acgctgacgg tacaggccag   2220
acaattattg tctggtatag tgcagcagca gaacaatttg ctgagggcta ttgaggcgca   2280
acagcatctg ttgcaactca cagtctgggg catcaagcag ctccaggcaa gaatcctggc   2340
tgtggaaaga tacctaaagg atcaacagct cctggggatt tggggttgct ctggaaaact   2400
catttgcacc actgctgtgc cttggaatgc tagttggagt aataaatctc tggaacagat   2460
ttggaatcac acgacctgga tggagtggga cagagaaatt aacaattaca caagcttggt   2520
aggtttaaga atagtttttg ctgtactttc tatagtgaat agagttaggc agggatattc   2580
accattatcg tttcagaccc acctcccaac cccgagggga cccgacaggc ccgaaggaat   2640
agaagaagaa ggtggagaga gagacagaga cagatccatt cgattagtga acggatcctc   2700
acacaaaaaa ccaacacaca gatgtctagt agctctgatc ttttattcta gcggccgcta   2760
aggcgcgtcg acgtcggtga gcatccttgt atccagctgg cagtccattc gtcatatccc   2820
atctgccctg gcctagagct ggtaagcatg tgccgcactg cgcgatcgag tgttgaataa   2880
ctctaccaca tggagttatt caacactcga tcgcgcagcg tggcactgca ggaggccagg   2940
ccaagagctt ctgtggggaa gtgagatccc ccggggaat tcgatatcaa gcttatcgct   3000
agctatggtg tctgtttgag gttgctagtg aacacagttg tgtcagaagc aaatgtaagc   3060
```

```
aatagatggc tctgccctga cttttatgcc cagccctggc tcctgccctc cctgctcctg   3120
ggagtagatt ggccaaccct agggtgtggc tccacagggt gaggtctaag tgatgacagc   3180
cgtacctgtc cttggctctt ctggcactgg cttaggagtt ggacttcaaa ccctcagccc   3240
tccctctaag atatatctct tggccccata ccatcagtac aaattgctac taaaaacatc   3300
ctcctttgca agtgtattta ctagaatatg tcacattctg tctcaggcat ccattttctt   3360
tatgatgccg tttgaggtgg agttttagtc aggtggtcag cttctccttt ttttgccat    3420 ctgccctgta agcatcctgc tggggaccca gataggagtc atcactctag gctgagaaca   3480
tctgggcaca caccctaagc ctcagcatga ctcatcatga ctcagcattg ctgtgcttga   3540
gccagaaggt ttgcttagaa ggttacacag aaccagaagg cgggggtggg gcactgaccc   3600 cgacagggc  ctggccagaa ctgctcatgc ttggactatg ggaggtcact aatggagaca   3660
cacagaaatg taacaggaac taaggaaaaa ctgaagctta tttaatcaga gatgaggatg   3720
ctggaaggga tagagggagc tgagcttgta aaaagtatag taatcattca gcaaatggtt   3780
ttgaagcacc tgctggatgc taaacactat tttcagtgct tgaatcataa ataagaataa   3840 acatgtatc  ttattcccca caagagtcca agtaaaaaat aacagttaat tataatgtgc   3900
tctgtccccc aggctggagt gcagtggcac gatctcagct cactgcaacc tccgcctccc   3960
gactagtctc gaggctggtt agaaggttct actggaggag ggtcccagcc cattgctaaa   4020
ttaacatcag gctctgagac tggcagtata tctctaacag tggttgatgc tatcttctgg   4080
aacttgcctg ctacattgag accactgacc catacatagg aagcccatag ctctgtcctg   4140
aactgttagg ccactggtcc agagagtgtg catctccttt gatcctcata ataaccctat   4200
gagatagaca caattattac tcttacttta tagatgatga tcctgaaaac ataggagtca   4260
aggcacttgc ccctagctgg gggtataggg gagcagtccc atgtagtagt agaatgaaaa   4320
atgctgctat gctgtgcctc ccccacctt  cccatgtctg ccctctactc atggtctatc   4380
tctcctggct cctgggagtc atggactcca cccagcacca ccaacctgac ctaaccacct   4440
atctgagcct gccagcctat aacccatctg ggccctgata gctggtggcc agccctgacc   4500
ccaccccacc ctccctggaa cctctgatag acacatctgg cacaccagct cgcaaagtca   4560
ccgtgagggt cttgtgtttg ctgagtcaaa attccttgaa atccaagtcc ttagagactc   4620
ctgctcccaa atttacagtc atagacttct tcatggctgt ctcctttatc cacagaatga   4680
ttcctttgct tcattgcccc atccatctga tcctcctcat cagtgcagca cagggcccat   4740
gagcagtagc tgcagagtct cacataggtc tggcactgcc tctgacatgt ccgaccttag   4800
gcaaatgctt gactcttctg cctcgagaag cttatcgatg cggccgcgat atcgtcgagg   4860
gtacctttaa gaccaatgac ttacaaggca gctgtagatc ttagccactt tttaaaagaa   4920 aagggggggac tggaagggct aattcactcc caaagaagac aagatctgct ttttgcctgt   4980
actgggtctc tctggttaga ccagatctga gcctgggagc tctctggcta actagggaac   5040
ccactgctta agcctcaata aagcttgcct tgagtgcttc aatgtgtgtg ttggtttttt   5100
gtgtgtcgaa attctagcga ttctagcttg gcgtaatcat ggtcatagct gtttcctgtg   5160
tgaaattgtt atccgctcac aattccacac aacatacgag ccggaagcat aaagtgtaaa   5220
gcctggggtg cctaatgagt gagctaactc acattaattg cgttgcgctc actgcccgct   5280
ttccagtcgg gaaacctgtc gtgccagctg cattaatgaa tcggccaacg cgcggggaga   5340
ggcggtttgc gtattgggcg ctcttccgct tcctcgctca ctgactcgct gcgctcggtc   5400
gttcggctgc ggcgagcggt atcagctcac tcaaaggcgg taatacggtt atccacagaa   5460
```

```
tcaggggata acgcaggaaa gaacatgtga gcaaaaggcc agcaaaaggc caggaaccgt    5520
aaaaaggccg cgttgctggc gttttttccat aggctccgcc cccctgacga gcatcacaaa   5580
aatcgacgct caagtcagag gtggcgaaac ccgacaggac tataaagata ccaggcgttt   5640
cccctggaa gctccctcgt gcgctctcct gttccgaccc tgccgcttac cggatacctg    5700
tccgcctttc tcccttcggg aagcgtggcg ctttctcata gctcacgctg taggtatctc    5760
agttcggtgt aggtcgttcg ctccaagctg ggctgtgtgc acgaaccccc cgttcagccc    5820
gaccgctgcg ccttatccgg taactatcgt cttgagtcca acccggtaag acacgactta    5880
tcgccactgg cagcagccac tggtaacagg attagcagag cgaggtatgt aggcggtgct    5940
acagagttct tgaagtggtg gcctaactac ggctacacta agaacagt atttggtatc     6000
tgcgctctgc tgaagccagt taccttcgga aaaagagttg gtagctcttg atccggcaaa    6060
caaaccaccg ctggtagcgg tggtttttt gtttgcaagc agcagattac gcgcagaaaa    6120
aaaggatctc aagaagatcc tttgatcttt tctacggggt ctgacgctca gtggaacgaa    6180
aactcacgtt aagggatttt ggtcatgaga ttatcaaaaa ggatcttcac ctagatcctt    6240
ttaaattaaa aatgaagttt taaatcaatc taaagtatat atgagtaaac ttggtctgac    6300
agttaccaat gcttaatcag tgaggcacct atctcagcga tctgtctatt tcgttcatcc    6360
atagttgcct gactccccgt cgtgtagata actacgatac ggagggctt accatctggc    6420
cccagtgctg caatgatacc gcgagaccca cgctcaccgg ctccagattt atcagcaata    6480
aaccagccag ccggaagggc cgagcgcaga agtggtcctg caactttatc cgcctccatc    6540
cagtctatta attgttgccg ggaagctaga gtaagtagtt cgccagttaa tagtttgcgc    6600
aacgttgttg ccattgctac aggcatcgtg gtgtcacgct cgtcgtttgg tatggcttca    6660
ttcagctccg gttcccaacg atcaaggcga gttacatgat cccccatgtt gtgcaaaaaa    6720
gcggttagct ccttcggtcc tccgatcgtt gtcagaagta agttggccgc agtgttatca    6780
ctcatggtta tggcagcact gcataattct cttactgtca tgccatccgt aagatgcttt    6840
tctgtgactg gtgagtactc aaccaagtca ttctgagaat agtgtatgcg gcgaccgagt    6900
tgctcttgcc cggcgtcaat acgggataat accgcgccac atagcagaac tttaaaagtg    6960
ctcatcattg gaaaacgttc ttcggggcga aaactctcaa ggatcttacc gctgttgaga    7020
tccagttcga tgtaacccac tcgtgcaccc aactgatctt cagcatcttt tactttcacc    7080
agcgtttctg ggtgagcaaa aacaggaagg caaaatgccg caaaaaaggg aataagggcg    7140
acacggaaat gttgaatact catactcttc ctttttcaat attattgaag catttatcag    7200
ggttattgtc tcatgagcgg atacatattt gaatgtattt agaaaaataa acaaataggg    7260
gttccgcgca catttccccg aaaagtgcca cctgggacta ctttttgca aaagcctagg    7320
cctccaaaaa agcctcctca ctacttctgg aatagctcag aggccgaggc ggcctcggcc    7380
tctgcataaa taaaaaaaat tagtcagcca tggggcggag aatgggcgga actgggcgga    7440
gttaggggcg ggatgggcgg agttagggc gggactatgg ttgctgacta attgagatga    7500
gcttgcatgc cgacattgat tattgactag tccctaagaa accattctta tcatgacatt    7560
aacctataaa aataggcgta tcacgaggcc ctttcgtc                           7598
```